US006855688B2

(12) United States Patent
McKerracher

(10) Patent No.: US 6,855,688 B2
(45) Date of Patent: Feb. 15, 2005

(54) **ADP-RIBOSYL TRANSFERASE FUSION PROTEINS, PHARMACEUTICAL COMPOSITIONS, AND MET

OTHER PUBLICATIONS

Keino–Masu, et al., Cell. 87:175–185 (1996).
Matsui, et al., EMBO J. 15:2208–2216 (1996).
Matsui, et al., J. Cell Biol. 140:647–657 (1998).
Ishizaki, FEBS Lett. 404:118–124 (1997).
Miyata et al (2000) 20: 2351–8.
Robertson et al (2000) 131: 5–9.
Chitaley et al (2001) 7: 119–22.
Han et al (2001) J. Mol. Biol. 305: 95.
Uehata, et al., Nature 389:990–994 (1997).
Rojas (1998) 16: 370–375.
Vives (1997) 272: 16010–16017.
Wender et al 2000, PNAS 24: 13003–13008.
Derossi (1996) 271: 18188–18193.
Frankel (1998) A.D. et al Cell., 55: 1189–1193.
Aullo, et al. (1993) 12: 921–31.
Fawell (1994) 91: 664–668.
Bloch–Gallego (1993) 120; 485–492.
Schwarze et al (1999) 285: 1569–72.
Diekmann and Hall, in Methods in Enzymology vol. 256 part B 207–215 (1995).
David et al (1995) 42: 594–602.
Janknecht, et al., Proc. Natl. Acad. Sci. USA 88, 8972 (1981).
Ridley and Hall, Cell. 70:389–399 (1992).
Somlyo (1997) 389: 908–911.
Studier et al., 1990. Meth. Enzymol. 185: 60–89.
Greene A and Tischeler, A S PNAS 73: 2424 (1976).
Kazmierczak B I et al, cell. Microbiology England (2001) vol. 3, No. 2: pp. 85–98.
Winton MJ et al., Society for neuroscience, vol. 27, No. 2, (2001) p. 2120.

* cited by examiner

ADP-RIBOSYL TRANSFERASE FUSION PROTEINS, PHARMACEUTICAL COMPOSITIONS, AND METHODS OF USE

FIELD OF THE INVENTION

The present invention relates to conjugate or fusion type proteins (polypeptides) comprising, for example, C3 (see below) (i.e., C3-like protein, C3 chimeric proteins). Although, in the following, fusion-type proteins of the present invention, will be particularly discussed in relation to the use to facilitate regeneration of axons and neuroprotection, it is to be understood that the fusion proteins may be exploited in other contexts.

The present invention in particular pertains to the field of mammalian nervous system repair (e.g. repair of a central nervous system (CNS) lesion site or a peripheral nervous system (PNS) lesion site), axon regeneration and axon sprouting, neurite growth and protection from neurodegeneration and ischemic damage.

The Rho family GTPases regulates axon growth and regeneration. Inactivation of Rho with *Clostridium botulinum* C3 exotransferase (hereinafter simply referred to as C3) can stimulate regeneration and sprouting of injured axons; C3 is a toxin purified from *Clostridium botulinum* (see Saito et al., 1995, FEBS Lett 371:105–109; Wilde et al 2000. J. Biol. Chem. 275:16478). Compounds of the C3 family from *Clostridium botulinum* inactivate Rho by ADP-ribosylation and thus act as antagonists of Rho effect or function (Rho antagonists).

The present invention in particular relates to a means of intracellular delivery of C3 protein (e.g. C3 itself or other active analogues such as C3-like transferases—see below) or other Rho antagonists to repair damage in the nervous system, to prevent ischemic cell death, and to treat various disease where the inactivation of Rho is required. The means of delivery may take the form of chimeric (i.e. conjugate) C3-like Rho antagonists. These conjugate antagonists provide a significant improvement over C3 compounds (alone) because they are 3 to 4 orders of magnitude more potent with respect to the stimulation of axon growth on inhibitory substrates than recombinant C3 alone. Examples of these Rho antagonists have been made as recombinant proteins created to facilitate penetration of the cell membrane (i.e. to enhance cell uptake of the antagonists), improve dose-response when applied to neurons to stimulate growth on growth inhibitory substrates, and to inactivate Rho. Examples of these conjugate Rho antagonists are described below in relation to the designations C3APL, C3APLT, C3APS, C3-TL, C3-TS, C3Basic1, C3Basic2 and C3Basic3.

BACKGROUND OF THE INVENTION

Traumatic injury of the spinal cord results in permanent functional impairment. Most of the deficits associated with spinal cord injury result from the loss of axons that are damaged in the central nervous system (CNS). Similarly, other diseases of the CNS are associated with axonal loss and retraction, such as stroke, human immunodeficiency virus (HIV) dementia, prion diseases, Parkinson's disease, Alzheimer's disease, multiple sclerosis and glaucoma. Common to all of these diseases is the loss of axonal connections with their targets, and cell death. The ability to stimulate growth of axons from the affected or diseased neuronal population would improve recovery of lost neurological functions, and protection from cell death can limit the extent of damage. For example, following a white matter stroke, axons are damaged and lost, even though the neuronal cell bodies are alive, and stroke in grey matter kills many neurons and non-neuronal (glial) cells. Treatments that are effective in eliciting sprouting from injured axons are equally effective in treating some types of stroke (Boston life sciences, Sep. 6, 2000 Press release). Neuroprotective agents often tested as potential compounds that can limit damage after stroke. Compounds which show both growth-promotion and neuroprotection are especially good candidates for treatment of stroke and neurodegenerative diseases. Similarly, although the following discussion will generally relate to delivery of Rho antagonists, etc. to a traumatically damaged nervous system, this invention may also be applied to damage from unknown causes, such as during stroke, multiple sclerosis, HIV dementia, Parkinson's disease, Alzheimer's disease, prion diseases or other diseases of the CNS were axons are damaged in the CNS environment. Also, Rho is an important target for treatment of cancer and metastasis (Clark et al (2000) Nature 406:532–535), and hypertension (Uehata et al. (1997) Nature 389:990) and RhoA is reported to have a cardioprotective role (Lee et al. FASEB J. 15:1886–1884). Therefore, the new C3-like proteins are expected to be useful for a variety of diseases were inhibition of Rho activity is required.

It has been proposed to use various Rho antagonists as agents to stimulate regeneration of (cut) axons, i.e. nerve lesions; please see, for example, Canadian Patent application Nos. 2,304,981 (McKerracher et al) and 2,300,878 (Strittmatter). These patent application documents propose the use of known Rho antagonists such as for example C3, chimeric C3 proteins, etc. (see blow) as well as substances selected from among known trans-4-amino (alkyl)-1-pyridylcarbamoylcyclohexane compounds (also see below) or Rho kinase inhibitors for use in the regeneration of axons. C3 inactivates Rho by ADP-ribosylation and is fairly non-toxic to cells (Dillon and Feig (1995) Methods in Enzymology: Small GTPases and their regulators Part. B.256:174–184).

While the following discussion will generally relate or be directed at repair in the CNS, the techniques described herein may be extended to use in many other diseases including, but not restricted to, cancer, metastasis, hypertentension, cardiac disease, stroke, diabetic neuropathy, and neurodegenerative disorders such as stroke, Alzheimer's disease, Parkinson's disease, amyotrophic lateral sclerosis (ALS). Treatment with Rho antagonists would be used to enhance the rate of axon growth of peripheral nerves and thereby be effective for repair of peripheral nerves after surgery, for example after reattaching severed limbs. Also, treatment with our fusion compounds (proteins) is expected to be effective for the treatment of various peripheral neuropathies because of their axon growth promoting effects.

As mentioned above, traumatic injury of the spinal cord results in permanent functional impairment. Axon regeneration does not occur in the adult mammalian CNS because substrate-bound growth inhibitory proteins block axon growth. Many compounds, such as trophic factors, enhance neuronal differentiation and stimulate axon growth in tissue culture. However, most factors that enhance growth and differentiation are not able to promote axon regenerative growth on inhibitory substrates. To demonstrate that a compound known to stimulate axon growth in tissue culture most accurately reflects the potential for therapeutic use in axon regeneration in the CNS, it is important for the cell culture studies to include the demonstration that a compound can permit axon growth on growth inhibitory substrates. An example of trophic and differentiation factors that stimulate growth on permissive substrates in tissue culture, are neurotrophins such as nerve growth factor (NGF) and brain-derived growth factor. NGF, however, does not promote growth on inhibitory substrates (Lehmann, et al. (1999) 19: 7537–7547) and it has not been effective in promoting axon regeneration in vivo. Brain derived neurotrophic factor (BDNF) is not effective to promote regeneration in vivo either (Mansour-Robaey, et al. J. Neurosci. (1994) 91: 1632–1636). BDNF does not promote neurite growth on growth inhibitory substrates (Lehmann et al supra).

Targeting intracellular signaling mechanisms involving Rho and the Rho kinase for promoting axon regeneration has been proposed (see, for example, the above-mentioned Canadian Patent application nos. 2,304,981 (McKerracher et al)). For demonstration that inactivation of Rho promotes axon regeneration on growth inhibitory substrates, recombinant C3, a protein that inactivates Rho by ADP ribosylation of the effector domain was used. While such a C3 protein can effectively promote regeneration, it has been noted that such a C3 protein does not easily penetrate into cells, and high doses must therefore be applied for it to be effective.

The high dose of recombinant C3 needed to promote functional recovery presents a practical constraint or limitation on the use of C3 in vivo to promote regeneration (Lehmann, et al. (1999) J. Neurosci. 19: 7537–7547; Morii, N and Narumiya, S. (1995) Methods in Enzymology, Vol 256 part B, pg. 196–206. In tissue culture studies, it has, for example, been determined that the minimum amount of C3 that can be used to induce growth on inhibitory substrates is 25 ug/ml (Lehmann, et al. (1999) J. Neurosci. 19: 7537–7547; Morii, N and Narumiya, S. (1995) Methods in Enzymology, Vol 256 part B, pg. 196–206. If the cells are not triturated, even this dose is ineffective. It has been estimated, for example, that at least 40 $\mu$g of C3 per 20 g mouse needs to be applied to injured mouse spinal cord or rat optic nerve (McKerracher, Canadian patent application No.: 2,325,842). Calculating doses that would be required to treat an adult human on an equivalent dose per weight scale up used for rat and mice experiments, it would be necessary to apply 120 mg/kg of C3 (i.e. alone) to the injured human spinal cord. The large amount of recombinant C3 protein needed creates significant problems for manufacturing, due to the large-scale protein purification and cost. It also limits the dose ranging that can be tested because of the large amount of protein needed for minimal effective doses.

Another related limitation with respect to the use of C3 to promote repair in the injured CNS is that it does not easily penetrate the plasma membrane of living cells. In tissue culture studies when C3 is applied to test biological effects it has been microinjected directly into the cell (Ridley and Hall (1992) Cell 70: 389–399), or applied by trituration of the cells to break the plasma membrane (Lehmann, et al. (1999) J. Neurosci.19: 7537–7547, Jin and Strittmatter (1997) J. Neurosci. 17: 6256–6263). In the case of axon injury in vivo, the C3 protein is likely able to enter the cell because injured axons readily take up substances from their environment. However, C3-like proteins of the present invention are likely to act also on surrounding undamaged neurons and help them make new connections as well, thus facilitating recovery. After incomplete SCI, there is plasticity of motor systems attributed to cortical and subcortical levels, including spinal cord circuitry (Raineteau, O., and Schwab, M. E. (2001) Nat Rev Neurosci 2: 263–73). This plasticity may be attributed to axonal or dendritic sprouting of collaterals and synaptic strengthening or weakening. Additionally, it has been shown that sparing of a few ventrolateral fibers may translate into significant differences in locomotor performance since these fibers are important in the initiation and control of locomotor pattern through spinal central pattern generators (Brustein, E., and Rossignol, S. (1998) *J Neurophysiol* 80: 1245–67). It is well documented that reorganization of spared collateral cortical spinal fibers occurs after spinal cord injury and this contributes to functional recovery (Weidner et al, 2001 Proc. Natl. Acad. Sci. 98: 3513–3518). The process of reorganization and sprouting of spared fibers would be enhanced by treatment with C3-like proteins able to enter non-injured neurons. This would enhances spontaneous plasticity of axons and dendritic remodeling known to help functional recovery.

Other methods of delivery of C3 in vitro have been to make a recombinant protein that can be taken up by a receptor-mediated mechanism (Boquet, P. et al. (1995) Meth. Enzymol. 256: 297–306). The disadvantage of this method is that the cells needing treatment must express the necessary receptor. Lastly, addition of a C2II binding protein to the tissue culture medium, along with a C21N-C3 fusion toxin allows uptake of C3 by receptor-mediated endocytosis (Barthe et al. (1998) Infection and Immunity 66:1364). The disadvantage of this system is that much of the C3 in the cell will be restrained within a membrane compartment. More importantly, two different proteins must be added separately for transport to occur (Wahl et al. 2000. J. Cell Biol. 149:263), which make this system difficult to apply to for treatment of disease in vivo.

SUMMARY OF THE INVENTION

In accordance with the present invention a conjugate, drug delivery construct, or fusion protein comprising a therapeutically active agent is provided whereby the active agent may be delivered across a cell wall membrane, the conjugate or fusion protein comprising at least a transport subdomain(s) or moiety(ies) (i.e., transport agent region) in addition to an active agent moiety(ies) (i.e., active agent region). More particularly, as discussed herein, in accordance with the present invention a conjugate or fusion protein is provided wherein the therapeutically active agent is one able to facilitate (for facilitating) axon (or dendrite, or neurite) growth (e.g. regeneration) i.e. a conjugate or fusion protein in the form of a conjugate Rho antagonist.

The present invention in accordance with an aspect thereof provides a drug delivery construct or conjugate [e.g. able to (for) suppress(ing) the inhibition of neuronal axon growth at a central nervous system (CNS) lesion site or a peripheral nervous system (PNS) lesion site] comprising at least one transport agent region and an active agent region not naturally associated with the active agent region, wherein the transport agent region is able to facilitate (i.e. facilitates) the uptake of the active agent region into a mammalian (i.e. human or animal) tissue or cell, and wherein the active agent region is an active therapeutic agent region able (i.e. has the capacity or capability) to facilitate axon growth for example on growth inhibitory substrates (e.g. regeneration), either in vivo (in a mammal (e.g., human or animal)) or in vitro (in cell culture), including a derivative or homologue thereof (i.e. pharmaceutically acceptable chemical equivalents thereof—pharmaceutically acceptable derivative or homologue).

In accordance with the present invention the active agent region may be an ADP-ribosyl transferase C3 region. In accordance with the present invention the ADP-ribosyl transferase C3 may be selected from the group consisting of ADP-ribosyl transferase (e.g., ADP-ribosyl transferase C3) derived from *Clostridium botulinum* and a recombinant ADP-ribosyl transferase (e.g., recombinant ADP-ribosyl transferase C3) that includes the entire C3 coding region, or only a part (fragment) of the C3 coding region that retains the ADP-ribosyl transferase activity, or analogues (derivatives) of C3 that retains the ADP-ribosyl transferase activity, or enough of the C3 coding region to be able to effectively inactivate Rho. The active agent could also be selected from other known ADP-ribosyl transferases that act on Rho (Wilde et al. 2000 J. Biol. Chem. 275–16478–16483; Wilde et al 2001. J. Biol. Chem. 276:9537–9542).

In accordance with another aspect the present invention provides a drug conjugate consisting of a transport polypeptide moiety (e.g. rich in basic amino acids e.g. arginine, lysine, histidine, asparagine, glutamine) covalently linked to an active cargo moiety (e.g. by a peptide bond or a labile bond (i.e. a bond readily cleavable or subject to chemical change in the interior target cell environment)) wherein the transport polypeptide moiety is able to or has the capability to facilitate(s) the uptake of the active cargo moiety into a mammalian (e.g. human or animal) tissue or cell (for example, a transport subdomain of HIV (e.g., HIV-1) Tat protein, a homeoprotein transport sequence (referred also as a transport homeoprotein) (e.g. the homeodomain of antennapedia), a Histidine tag (ranging in length from 4 to 30 histidine repeat) or a variation derivative or homologue thereof, (i.e. pharmaceutically acceptable chemical equivalents thereof)) [by a receptor independent process] and wherein the active cargo moiety is an active therapeutic moiety able (i.e. has the capacity or capability) to facilitate (i.e. for facilitating) axon growth (e.g. regeneration, budding) or neuroprotection (prevention of cell death) either in vivo (in a mammal (e.g., human or animal)) or in vitro (in cell culture).

In accordance with the present invention the transport polypeptide moiety may be selected from the group consisting of SEQ ID NO.: 48, a transport subdomain of HIV (e.g., HIV-1) Tat protein such as for example SEQ ID NO.: 46, SEQ ID NO.:47, a homeodomain of antennapedia, such as for example SEQ ID NO.: 44, SEQ ID NO.: 45, a Histidine tag and a functional derivative and analogues thereof (e.g., SEQ ID NO.: 21, SEQ ID NO.: 26, SEQ ID NO.: 31) [i.e. by the addition of polyamine, or any random sequence enriched in basic amino acids]—[i.e. pharmaceutically acceptable chemical equivalents thereof] and wherein the active cargo moiety is selected from the group consisting of C3 protein able (i.e. has the capacity or capability) to facilitate (i.e. for facilitating) axon growth (e.g. regeneration, budding) or neuroprotection (prevention of cell death) either in vivo (in a mammal (e.g., human or animal)) or in vitro (in cell culture).

In accordance with the present invention the C3 protein may be selected from the group consisting of ADP-ribosyl transferase C3 and ADP-ribosyl transferase C3 analogue. In accordance with the present invention the ADP-ribosyl transferase C3 may be selected from the group consisting of ADP-ribosyl transferase (e.g., ADP-ribosyl transferase C3) derived from *Clostridium botulinum* and a recombinant ADP-ribosyl transferase (e.g., recombinant ADP-ribosyl transferase C3). The ADP-ribosyl transferase may be a protein with a C3-like activity, such as that derived from *Staphylococcus aureus* (Wilde et al 2001. J. Biol. Chem. 276:9537–9542). The ADP-ribosyl transferase may be any other transferase that acts to inactivate RhoA, RhoB and/or RhoC such as those derived from *Clostridium limosum*, and *Bacillus cereus* (Wilde et al 2000. J. Biol. Chem. 275:16478–16483). In accordance with the present invention the transport polypeptide moiety may include an active contiguous amino acid sequence as described herein.

In accordance with an additional aspect the present invention provides a fusion protein (polypeptide) [e.g. able to (for) suppress(ing) the inhibition of neuronal axon growth at a central nervous system (CNS) lesion site or a peripheral nervous system (PNS) lesion site] consisting of a carboxy terminal active cargo moiety and an amino terminal transport moiety, wherein the amino terminal transport moiety is selected from the group consisting of a transport subdomain of HIV (e.g., HIV-1) Tat protein, homeoprotein transport sequence (referred also as a transport homeoprotein) (e.g. the homeodomain of antennapedia), a Histidine tag and a functional derivatives and analogues thereof (i.e. pharmaceutically acceptable chemical equivalents thereof) and wherein the active cargo moiety consists of a C3 protein.

The present invention in particular provides a fusion protein (polypeptide) (e.g. able to (for) suppressing the inhibition of neuronal axon growth at a central nervous system (CNS) lesion site or a peripheral nervous system (PNS) lesion site) consisting of a carboxy terminal active cargo moiety and an amino terminal transport moiety, wherein the amino terminal transport moiety consists of the homeodomain of antennapedia and the active cargo moiety consists of a C3 protein (i.e. as described herein).

The present invention also in particular provides a fusion protein (polypeptide) (e.g. able to (for) suppressing the inhibition of neuronal axon growth at a central nervous system (CNS) lesion site or a peripheral nervous system (PNS) lesion site) consisting of a carboxy terminal active cargo moiety and an amino terminal transport moiety, wherein the amino terminal transport moiety consists of a transport subdomain of (e.g., HIV-1) Tat protein and the active cargo moiety consists of a C3 protein (i.e. as described herein).

In accordance with the present invention the C3 protein may be selected from the group consisting of ADP-ribosyl transferase C3 and ADP-ribosyl transferase C3 analogues. In accordance with the present invention the ADP-ribosyl transferase C3 is selected from the group consisting of ADP-ribosyl transferase (e.g., ADP-ribosyl trans ferase C3) derived from *Clostridium botulinum* and a recombinant ADP-ribosyl transferase (e.g., recombinant ADP-ribosyl transferase C3).

In accordance with an additional aspect the present invention provides a fusion protein (polypeptide) [e.g. able to (for) suppress(ing) the inhibition of neuronal axon growth at a central nervous system (CNS) lesion site or a peripheral nervous system (PNS) lesion site] consisting of an amino terminal active cargo moiety and a carboxy terminal transport moiety, wherein the carboxy terminal transport moiety is selected from the group consisting of a transport subdomain of HIV Tat protein, a homeoprotein transport sequence (referred also as a transport homeoprotein) (e.g. the homeodomain of antennapedia), a Histidine tag and a functional derivatives and analogues thereof (i.e. pharmaceutically acceptable chemical equivalents thereof) and wherein the active cargo moiety consists of a C3 protein.

The present invention in particular provides a fusion protein (polypeptide) (e.g. able to (for) suppressing the inhibition of neuronal axon growth at a central nervous system (CNS) lesion site or a peripheral nervous system (PNS) lesion site) consisting of an amino terminal active cargo moiety and a carboxy terminal transport moiety, wherein the carboxy terminal transport moiety consists of the homeodomain of antennapedia and the active cargo moiety consists of a C3 protein (i.e. as described herein).

The present invention also in particular provides a fusion protein (polypeptide) (e.g. able to (for) suppressing the inhibition of neuronal axon growth at a central nervous system (CNS) lesion site or a peripheral nervous system (PNS) lesion site) consisting of an amino terminal active cargo moiety and a carboxy terminal transport moiety, wherein the carboxy terminal transport moiety consists of a transport subdomain of HIV Tat protein and the active cargo moiety consists of a C3 protein (i.e. as described herein).

In accordance with the present invention the C3 protein may be selected from the group consisting of ADP-ribosyl transferase C3 and ADP-ribosyl transferase C3 analogues. In accordance with the present invention the ADP-ribosyl transferase C3 is selected from the group consisting of ADP-ribosyl transferase C3 derived from *Clostridium botulinum* and a recombinant ADP-ribosyl transferase C3.

The present invention in a further aspect provides for the use of a member selected from the group consisting of a drug delivery construct as described herein, a drug conjugate as described herein and a fusion protein (polypeptide) as described herein (e.g. including pharmaceutically acceptable chemical equivalents thereof) for suppressing the inhibition of neuronal axon growth.

The present invention in a further aspect relates to a pharmaceutical composition (e.g. for suppressing the inhibition of neuronal axon growth), the pharmaceutical composition comprising a pharmaceutically acceptable diluent or carrier and an effective amount of an active member selected from the group consisting of a drug delivery construct as described herein, a drug conjugate as described herein, and a fusion protein (polypeptide) as described herein (e.g. including pharmaceutically acceptable chemical equivalents thereof).

The present invention further provides for the use of a member selected from the group consisting of a drug delivery construct as described herein, a drug conjugate as described herein, and a fusion protein (polypeptide) as described herein (e.g. including pharmaceutically acceptable chemical equivalents thereof) for the manufacture of a pharmaceutical composition (e.g. for suppressing the inhibition of neuronal axon growth).

The present invention also relates to a method for preparing a drug delivery construct, a conjugate or fusion protein (polypeptide) as defined above comprising
  cultivating a host cell (bacterial or eukaryotic) under conditions which provide for the expression of the drug delivery construct, the conjugate or fusion protein (polypeptide) within the cell; (the drug delivery construct, conjugate or fusion protein (polypeptide), could also be expressed to be produced in an animals, such as, for example, the production of recombinant proteins in the milk of farm animals) and,
  recovering the drug delivery construct, conjugate or fusion protein (polypeptide) by a purification step.

The purification of the drug delivery construct, conjugate or fusion protein (polypeptide) may be done by affinity methods, ion exchange chromatography, size exclusion chromatography, hydrophobicity or any other purification technique typically used for protein purification. Preferably, the purification step would be performed under non-denaturating conditions. On the other hand, if a denaturating step is required, the protein may be renatured using techniques known in the art.

The present invention also relates to the expression of the drug delivery construct, conjugate or fusion protein (polypeptide) in a mammalian cell, which when used with a signal sequence, will allow expression and secretion of the fusion protein into the extracellular milieu. Other system of expression (yeast cells, bacterial cells, insect cells, etc.) may be suitable to express (produce) the drug delivery construct, conjugate or fusion protein (polypeptide) of the present invention as discussed herein.

The present invention in particular provides a fusion protein (polypeptide) selected from the group consisting of C3APL (SEQ ID NO.: 4), C3APLT (SEQ ID NO.: 37), C3APS (SEQ ID NO.:6), C3-TL (SEQ ID NO.:14), C3-TS (SEQ ID NO.: 18), C3Basic1 (SEQ ID NO.:25), C3Basic2 (SEQ ID NO.: 30), C3Basic3 (SEQ ID NO.:35), SEQ ID NO.: 20, and SEQ ID NO.: 43 and pharmaceutically acceptable chemical equivalents thereof.

In accordance with an additional aspect, the present invention provides a pharmaceutical composition comprising a polypeptide selected from the group consisting of C3APL (SEQ ID NO.:4), C3APLT (SEQ ID NO.:37), C3APS (SEQ ID NO.:6), C3-TL (SEQ ID NO.: 14), C3-TS (SEQ ID NO.:18), C3Basic1 (SEQ ID NO.:25), C3Basic2 (SEQ ID NO.:30), C3Basic3 (SEQ ID NO.:35), SEQ ID NO.: 20 and SEQ ID NO.: 43, and a pharmaceutically acceptable carrier.

In accordance with the present invention, the pharmaceutical composition may further comprise a biological adhesive, such as, for example, fibrin (fibrin glue).

In a further aspect the present invention provides a pharmaceutical composition comprising a polypeptide comprising at least one (one or more) transport agent region and an active agent region, said active agent region being selected from the group consisting of ADP-ribosyl transferase C3 and ADP-ribosyl transferase C3 analogues, and a pharmaceutically acceptable carrier.

In accordance with the present invention, the transport agent region may be at the carboxy-terminal end of said polypeptide and the active agent region may be at the amino terminal end of said polypeptide.

In accordance with the present invention, the pharmaceutical composition may further comprise a biological adhesive, such as, for example, fibrin (fibrin glue).

In an additional aspect, the present invention provides a polypeptide comprising at least one (one or more) transport agent region and an active agent region, said active agent region being selected from the group consisting of ADP-ribosyl transferase C3 and ADP-ribosyl transferase C3 analogues (wherein the transport agent region is able to facilitate the uptake of the active agent region into (inside the cell or in the cell membrane) a cell).

In an additional aspect, the present invention provides a polypeptide consisting of a carboxy-terminal active agent moiety and an amino-terminal transport moiety region (wherein the transport agent region is able to facilitate the uptake of the active agent region into (inside the cell or in the cell membrane) a cell) and wherein said carboxy-terminal active agent moiety may be selected from the group consisting of ADP-ribosyl transferase C3 and ADP-ribosyl transferase C3 analogues thereof.

In accordance with the present invention, the carboxy-terminal transport moiety region may be selected from the group consisting of a basic amino acid rich region and a proline rich region.

In a further aspect, the present invention relates to a polypeptide consisting of an amino-terminal active agent moiety and a carboxy-terminal transport moiety region, wherein said amino-terminal active agent moiety may be selected from the group consisting of ADP-ribosyl transferase C3 and ADP-ribosyl transferase C3 analogues thereof.

In accordance with the present invention, the carboxy-terminal transport moiety region may be selected from the group consisting of a basic amino acid rich region and a proline rich region.

In yet a further aspect, the present invention relates to a conjugate comprising at least one transport agent region (including one, two, three or more transport agent region) and an active agent region, said active agent region being selected from the group consisting of ADP-ribosyl transferase C3 and ADP-ribosyl transferase C3 analogues, wherein said transport agent region is covalently linked to said active agent region.

In accordance with the present invention, the transport agent region may be cross-linked (e.g., chemically cross-linked, UV cross-linked) to the active agent region (C3-like proteins of the present invention and analogues thereof).

In accordance with the present invention, the transport agent region may be fused to ADP-ribosyl transferase C3 and ADP-ribosyl transferase C3 analogues according to recombinant DNA technology (e.g., cloning the DNA sequence of the transport agent region in frame with the DNA sequence of the ADP-ribosyl transferase C3 or an ADP-ribosyl transferase C3 analogue comprising or not a spacer DNA sequence (multiple cloning site, linker) or any other DNA sequence that would not interfere with the activity of the C3-like protein once expressed).

In an additional aspect, the present invention relates to the use of a polypeptide selected from the group consisting of C3APL (SEQ ID NO.: 4), C3APLT (SEQ ID NO.:37), C3APS (SEQ ID NO.:6), C3-TL (SEQ ID NO.:14), C3-TS (SEQ ID NO.:18), C3Basic1 (SEQ ID NO.:25), C3Basic2 (SEQ ID NO.:30), C3Basic3 (SEQ ID NO.:35), SEQ ID NO.: 20 and SEQ ID NO.: 43, for the manufacture of a pharmaceutical composition.

In other aspects, the present invention relates to the use of a polypeptide comprising at least one (one or more) transport agent region and an active agent region, for the manufacture of a pharmaceutical composition, or to facilitate (for facilitating) axon growth or for treating (in the treatment of) nerve injury (e.g., nerve injury arising from traumatic nerve injury or nerve injury caused by disease), or for preventing (diminishing, inhibiting (partially or totally)) cell apoptosis (cell death, such as following ischemia in the CNS), or for suppressing (diminishing) the inhibition of neuronal axon growth, or for the treatment of ischemic damage related to stroke, or for suppressing (diminishing) Rho activity, or to regenerate (for regenerating) injured axon (helping injured axon to recover, partially or totally, their function), or to help (for helping) neurons to make new connections (developing axon, dendrite, neurite) with other (surrounding) cells (neuronal cells), in a mammal, (e.g., human, animal), wherein said active agent region being selected from the group consisting of ADP-ribosyl transferase C3 and ADP-ribosyl transferase C3 analogues.

In accordance with the present invention, the transport agent region may be at the amino-terminal end of the polypeptide (i.e., protein) and the ADP-ribosyl transferase C3 or ADP-ribosyl transferase C3 analogue may be at the carboxy-terminal end of the polypeptide (i.e., protein).

In accordance with the present invention, the transport agent region may be at the carboxy-terminal end of the polypeptide (i.e., protein) and the ADP-ribosyl transferase C3 or ADP-ribosyl transferase C3 analogue may be at the amino-terminal end of the polypeptide (i.e., protein).

In a further aspect, the present invention provides a method of (for) suppressing the inhibition of neuronal axon growth (e.g., in a mammal, (e.g., human, animal)) comprising administering (e.g., delivering) a member selected from the group consisting of a drug delivery construct, a drug conjugate, a fusion protein and a polypeptide (e.g. including pharmaceutically acceptable chemical equivalents thereof), said polypeptide comprising at least one (one or more) transport agent region and an active agent region selected from the group consisting of ADP-ribosyl transferase C3 and ADP-ribosyl transferase C3 analogues (directly) at (to) a central nervous system (CNS) lesion site or a peripheral nervous system (PNS) lesion site (of a patient), in an amount effective to counteract said inhibition. Such application could be useful for treatment of a wide variety of peripheral neuropathies, such as diabetic neuropathy.

The present invention, for example, provides recombinant Rho antagonists comprising C3 enzymes with basic stretches of amino acids (e.g., a basic amino acid rich region) or a proline rich region added to the C3 coding sequence to facilitate the uptake thereof into tissue or cells for the repair and/or promotion of repair or promotion of growth in the CNS, even in the lack of traumatic axon damage. Examples of basic amino acid rich regions and proline rich regions are given below.

In yet a further aspect, the present invention provides a method of (for) facilitating axon growth (e.g., in a mammal, (e.g., human, animal)) comprising delivering a polypeptide or conjugate comprising at least one transport agent region and an active agent region selected from the group consisting of ADP-ribosyl transferase C3 and ADP-ribosyl transferase C3 analogues directly at a central nervous system (CNS) lesion site or a peripheral nervous system (PNS) lesion site, in an amount effective to facilitate said growth.

In an additional aspect, the present invention provides a method of (for) treating nerve injury (e.g., in a mammal, (e.g., human, animal)) comprising delivering a polypeptide or conjugate comprising at least one transport agent region and an active agent region selected from the group consisting of ADP-ribosyl transferase C3 and ADP-ribosyl transferase C3 analogues directly at (to) a central nervous system (CNS) lesion site or a peripheral nervous system (PNS) lesion site.

In yet an additional aspect, the present invention provides a method of (for) preventing cell apoptosis (e.g., in a mammal, (e.g., human, animal)) comprising delivering a polypeptide or conjugate comprising at least one transport agent region and an active agent region selected from the group consisting of ADP-ribosyl transferase C3 and ADP-ribosyl transferase C3 analogues directly at a central nervous system (CNS) lesion site or a peripheral nervous system (PNS) lesion site.

In another aspect, the present invention provides a method of (for) treating ischemic damage related to stroke (e.g., in a mammal, (e.g., human, animal)) comprising delivering a polypeptide or conjugate comprising at least one transport agent region and an active agent region selected from the group consisting of ADP-ribosyl transferase C3 and ADP-ribosyl transferase C3 analogues directly at a central nervous system (CNS) lesion site (to said mammal).

In yet another aspect, the present invention provides a method of (for) suppressing Rho activity comprising delivering a polypeptide or conjugate comprising at least one transport agent region and an active agent region selected from the group consisting of ADP-ribosyl transferase C3 and ADP-ribosyl transferase C3 analogues directly at a central nervous system (CNS) lesion site or a peripheral nervous system (PNS) lesion site, in an amount effective to suppress said activity.

In accordance with an additional aspect, the present invention provides a method of (for) regenerating injured axon (e.g., in a mammal, (e.g., human, animal)) comprising delivering a polypeptide or conjugate comprising at least one transport agent region and an active agent region selected from the group consisting of ADP-ribosyl transferase C3 and ADP-ribosyl transferase C3 analogues directly at a central nervous system (CNS) lesion site or a peripheral nervous system (PNS) lesion site (e.g., in a mammal), in an amount effective to regenerate said injured axon.

In accordance with a further aspect, the present invention provides a method of (for) helping neurons to make new cell connection (developing axon, dendrite, neurite with other (surrounding) cells (neuronal cells) comprising delivering a polypeptide or conjugate comprising at least one transport agent region and an active agent region selected from the group consisting of ADP-ribosyl transferase C3 and ADP-ribosyl transferase C3 analogues directly at a central nervous system (CNS) lesion site or a peripheral nervous system (PNS) lesion site.

In an additional aspect, the present invention provides a method for (of) preparing a polypeptide comprising at least one (one or more) transport agent region and an active agent region, wherein said transport agent region may be selected from the group consisting of SEQ ID NO.: 21, SEQ ID NO.: 26, SEQ ID NO.: 31, SEQ ID NO.: 44, SEQ ID NO.: 45, SEQ ID NO.: 46, SEQ ID NO.: 47, SEQ ID NO.: 48 and analogues thereof, and wherein said active agent region may be selected from the group consisting of ADP-ribosyl transferase C3 and ADP-ribosyl transferase C3 analogues, said method comprising:

cultivating a host cell under conditions which provide for the expression of the polypeptide within the cell; and
recovering the polypeptide by a purification step.

In accordance with the present invention, the purification of polypeptide may be done by affinity methods, ion exchange chromatography, size exclusion chromatography, hydrophobicity or any other purification technique typically used for protein purification. Preferably, the purification step would be performed under non-denaturating conditions. On the other hand, if a denaturating step is required, the protein may be renatured using techniques known in the art.

In another aspect, the present invention provides a polypeptide consisting of a basic amino acid rich region and an active agent region, wherein, amino acids from said basic rich region comprises amino acids selected from the group consisting of Histidine, Asparagine, Glutamine, Lysine and Arginine and wherein the active agent region is ADP-ribosyl transferase C3.

In yet another aspect, the present invention relates to the use of a polypeptide comprising at least one transport agent region and an active agent region, said active agent region being selected from the group consisting of ADP-ribosyl transferase C3 and ADP-ribosyl transferase C3 analogues for the manufacture of a medicament (or a pharmaceutical composition) for suppressing the inhibition of neuronal axon growth.

In accordance with the present invention, the polypeptide may be selected from the group consisting of C3APL (SEQ ID NO.: 4), C3APL (SEQ ID NO.:37), C3APS (SEQ ID NO.:6), C3-TL (SEQ ID NO.:14), C3-TS (SEQ ID NO.:18), C3Basic1 (SEQ ID NO.:25), C3Basic2 (SEQ ID NO.:30), C3Basic3 (SEQ ID NO.:35), SEQ ID NO.: 20 and SEQ ID NO.: 43.

In a further aspect, the present invention relates to the use of a polypeptide comprising at least one transport agent region and an active agent region, said active agent region being selected from the group consisting of ADP-ribosyl transferase C3 and ADP-ribosyl transferase C3 analogues for the manufacture of a medicament (or pharmaceutical composition) for facilitating axon growth.

In accordance with the present invention, the polypeptide may be selected from the group consisting of C3APL (SEQ ID NO.: 4), C3APLT (SEQ ID NO.:37), C3APS (SEQ ID NO.:6), C3-TL (SEQ ID NO.:14), C3-TS (SEQ ID NO.:18), C3Basic1 (SEQ ID NO.:25), C3Basic2 (SEQ ID NO.:30), C3Basic3 (SEQ ID NO.:35), SEQ ID NO.: 20 and SEQ ID NO.: 43.

In yet a further aspect the present invention relates to the use of a polypeptide comprising at least one (one or more) transport agent region and an active agent region, said active agent region being selected from the group consisting of ADP-ribosyl transferase C3 and ADP-ribosyl transferase C3 analogues for the manufacture of a medicament (or pharmaceutical composition) for treating nerve injury (e.g., in a mammal, (e.g., human, animal)).

In accordance with the present invention, the polypeptide may be selected from the group consisting of C3APL (SEQ ID NO.: 4), C3APLT (SEQ ID NO.:37), C3APS (SEQ ID NO.:6), C3-TL (SEQ ID NO.:14), C3-TS (SEQ ID NO.:18), C3Basic1 (SEQ ID NO.:25), C3Basic2 (SEQ ID NO.:30), C3Basic3 (SEQ ID NO.:35), SEQ ID NO.: 20 and SEQ ID NO.: 43.

In accordance with the present invention, the transport agent region discussed herein may be selected from the group consisting of a basic amino acid rich region (region comprising basic amino acid (e.g., arginine, lysine, histidine, glutamine, and/or asparagine)) and a proline rich region (e.g. region comprising prolines).

In accordance with the present invention, the basic amino acid rich region discussed herein may be selected from the group consisting of SEQ ID NO.: 48, a subdomain of HIV Tat protein (e.g., SEQ ID NO.: 46, SEQ ID NO.: 47, or any other subdomain of Tat, that could act as a transport sequence), a homeodomain of antennapedia (e.g., SEQ ID NO.: 44, SEQ ID NO.: 45, or any other domain of antennapedia, that could act as a transport sequence), a homeoprotein transport sequence, a Histidine tag, and analogues thereof (e.g., SEQ ID NO.: 21, SEQ ID NO.: 26, SEQ ID NO.:31).

In accordance with the present invention, the basic amino acid region discussed herein may be selected from the group consisting of SEQ ID NO.: 21(Basic1), SEQ ID NO.: 26 (Basic2), SEQ ID NO.: 31 (Basic3), SEQ ID NO.: 44 (APL), SEQ ID NO.: 45 (APS) SEQ ID NO.: 46 (TL), SEQ ID NO.: 47 (TS), and analogues thereof.

In accordance with the present invention, the proline rich region discussed herein may be selected from the group consisting of SEQ ID NO.: 48 (APLT) and analogues thereof.

In another aspect, the present invention provides an isolated polynucleotide comprising at least the polynucleotide sequence (for example the polynucleotide sequence disclosed herein in addition with (or in some cases without) a suitable (DNA) backbone (e.g., plasmid, viral vector)) selected from the group consisting of SEQ ID NO.: 3, SEQ ID NO.: 5, SEQ ID NO.: 13, SEQ ID NO.: 17, SEQ ID NO.: 19, SEQ ID NO.: 24, SEQ ID NO.: 29, SEQ ID NO.: 34, SEQ ID NO.: 36, and SEQ ID NO.: 42.

In yet another aspect, the present invention provides a cell transformed (transfected, transduced, infected, electroporated, micro-injected, etc.) with an isolated polynucleotide comprising at least the polynucleotide sequence (for example the polynucleotide sequence disclosed herein in addition with (or in some cases without) a suitable backbone (e.g., plasmid, viral vector)) selected from the group consisting of SEQ ID NO.: 3, SEQ ID NO.: 5, SEQ ID NO.: 13, SEQ ID NO.: 17, SEQ ID NO.: 19, SEQ ID NO.: 24, SEQ ID NO.: 29, SEQ ID NO.: 34, SEQ ID NO.: 36, and SEQ ID NO.: 42.

In a further aspect, the present invention provides a delivery agent consisting of a cargo moiety in combination with a transport moiety, wherein the transport moiety is selected from the group consisting of SEQ ID NO: 48 and analogues thereof. SEQ ID NO: 48 and analogues thereof act as a transport moiety which facilitate penetration of the cell membrane. Any cargo moiety (e.g., protein, chemicals) linked (e.g. attached) to SEQ ID NO: 48 or to some analogues thereof are encompassed by the present invention. For example, SEQ ID NO: 48 and analogues thereof may be fused to an anticancer agent, a therapeutic agent, an apoptotic agent, an anti-apoptotic agent, a reporter protein, an antibody, an antibody fragment, a dye, a probe, a marker etc.

In accordance with the present invention, the cargo moiety may retain biological activity following transport moiety-dependent intracellular delivery. Biological activity may include for example, biological properties (e.g. enzymatic activity) as well as its immunological properties. The cargo moiety may have a direct biological effect on the cell, such as for example killing the cell following its internalization or may have an indirect biological effect, for example, the cargo moiety may be a pro-drug that is inactive by itself but becomes active following modification (e.g., cleavage, phosphorylation, etc.) or when a second molecules is introduced inside the cell. The cargo moiety may also be a biologically inactive (i.e., inert) compound such as a labeling molecule (e.g., chemicals, proteins), an imaging molecule etc.

In accordance with the present invention, the agent may be a fusion protein having an amino-terminal that is the cargo moiety and having a carboxy-terminal that is the transport moiety.

In accordance with the present invention the cargo moiety may be selected from the group consisting of analytical molecules (e.g., molecules used in tissue culture experiments, markers, probes, dyes, reporter proteins) therapeutic molecules (e.g., toxin, drug, pro-drug), prophylactic molecules and diagnostic molecules (i.e., molecules used in in vivo or in vitro detection of a specific condition, metabolite, other molecule). Examples of analytical molecules, therapeutic molecules, prophylactic molecules and diagnostic molecules includes proteins (e.g., enzymes (e.g., nucleases, proteases, kinases, etc.), cytokines, chemokines, antigen, antibodies, antibody fragments, reporter proteins such as horseradish peroxidase, beta-galactosidase, fluorescent proteins (e.g., green fluorescent protein)), nucleic acids, polysaccharides, dyes, isotopes (e.g., radioisotope), markers, probes, and other types of chemicals. Transport polypeptides of the present invention may be advantageously attached to cargo molecules by chemical cross-linking or by genetic fusion.

In accordance with the present invention the cargo moiety may be selected from the group consisting of ADP-ribosyl transferase C3 and ADP-ribosyl transferase C3 analogues thereof.

In an additional aspect, the present invention relates to the polypeptide set forth in SEQ ID NO: 48 and analogues thereof.

In yet an additional aspect, the present invention provides a polypeptide as set forth in SEQ ID NO: 48 and analogues thereof, wherein said polypeptide and analogues may be able to act as a transport agent for the intracellular delivery of a cargo agent selected from the group consisting of analytical molecules, therapeutic molecules, prophylactic molecules, and diagnostic molecules.

In accordance with the present invention, the cargo agent may be selected from the group consisting of ADP-ribosyl transferase C3 and ADP-ribosyl transferase C3 analogues thereof.

The transport of a cargo moiety across the cellular membrane (intracellular delivery) may be facilitated (increased) when linked (e.g., genetically fused, chemically cross-linked, etc.) to SEQ ID NO: 48 and analogues thereof. Therefore it is an object of the present invention to provide a method for the intracellular delivery of a cargo moiety, the method comprising exposing the cell to a delivery agent comprising a cargo moiety and a transport moiety, said transport moiety being selected from the group consisting of SEQ ID NO: 48 and analogues thereof and wherein said transport moiety enables the delivery agent to be delivered inside the cell (i.e., across cellular membranes). An example of a cargo moiety that may be delivered across the cell membrane is ADP-ribosyl transferase C3 and analogues thereof. Other examples of a cargo moiety are mentionned herein. The method also comprise bringing the delivery agent comprising a cargo moiety and a transport moiety (SEQ ID NO: 48 and analogues thereof) in the surrounding of a target cell in a manner (e.g., concentration) sufficient to permit the uptake of the delivery agent by the cell. For example, in the case of in vitro (e.g., cell culture) delivery, the delivery agent (in a pharmaceutically acceptable carrier, diluent, excipient, etc.) may be added directly to the extracellular milieu (e.g., cell culture media) of adherent cells (i.e., cell lines or primary cells) or cells in suspension. Alternatively, cells may be harvested and concentrated before being put in contact with the delivery agent. Intracellular delivery may be monitored by techniques known in the art, such as for example, immunofluorescence, immunohistochemistry or by the intrinsic properties of the cargo moiety (e.g., its enzymatic activity).

In vivo delivery (in a mammal) may be performed for example, by exposing (i.e., contacting) a tissue, a nerve injury site, an open wound, etc. with the delivery agent (in a pharmaceutically acceptable carrier, diluent, excipient, fibrin gel etc.) of the present invention in an amount sufficient to promote the biological effect of the cargo moiety (e.g., recovery, healing of the wounded tissue, etc.). In addition, in vivo delivery may be performed by other methods known in the art such as for example, injection via the intramuscular (IM), subcutaneous (SC), intra-dermal (ID), intra-venous (IV) or intra-peritoneal (IP) routes or administration at the mucosal membranes including the oral and nasal cavity membranes using any suitable means. Alternatively, cells may be isolated from a mammal and treated (exposed) ex-vivo (e.g., in gene therapy techniques) with the delivery agent of the present invention before being re-infused in the same individual or in a compatible individual.

The term "Rho antagonists" as used herein includes, but is not restricted to, (known) C3, including C3 chimeric proteins, and like Rho antagonists.

The term "C3 protein" refers to ADP-ribosyl transferase C3 isolated from *Clostridium botulinum* or a recombinant ADP-ribosyl transferase.

The term "C3-like protein", "ADP-ribosyl transferase C3-like protein", "ADP-ribosyl transferase C3 analogue", "C3-like transferase" or "C3 chimeric proteins" as used herein refers to any protein (polypeptide) having a biological activity similar (e.g., the same, substantially similar), to ADP-ribosyl transferase C3. Examples of such C3-like protein include, for example, but are not restricteed to C3APL, C3APLT, C3APS, C3-TL, C3-TS, C3Basic1, C3Basic2 and C3Basic3 and the protein defined in SEQ ID NO.: 20.

The term "nerve injury site" refers to a site of traumatic nerve injury or nerve injury caused by disease. The nerve injury site may be a single nerve (eg sciatic nerve) or a nerve tract comprised of many nerves (eg. damaged region of the spinal cord). The nerve injury site may be in the central nervous system or peripheral nervous system or in any region needing repair. The nerve injury site may form as a result of damage caused by stroke. The nerve injury site may be in the brain as a result of surgery, brain tumour removal or therapy following a cancerous lesion. The nerve injury site may result from stroke, Parkinson's disease, Alzheimer's disease, amyotrophic lateral sclerosis (ALS), diabetes or any other type of neurodegenerative disease.

The term "cargo" refers to a molecule other than the transport moiety and that is either (1) not inherently capable of entering a cell (e.g., cell compartment) or (2) not inherently capable of entering a cell (e.g., cell compartment) at a useful rate. The term "cargo" as used herein refers either to a molecule per se, i.e., before conjugation, or to the cargo moiety of a transport polypeptide-cargo conjugate. Examples of "cargo" include, but are not limited to, small molecules and macromolecules such as polypeptides, nucleic acids (polynucleotides), polysaccharides and chemicals.

As used herein, the term "delivery agent" relates to an agent comprising a cargo moiety and a transport moiety. Examples of cargo moiety are discussed above and includes for example ADP-ribosyl transferase C3 and ADP-ribosyl transferase C3 analogues. Examples of transport moiety comprise for example SEQ ID NO: 48 and analogues thereof.

"Polynucleotide" generally refers to any polyribonucleotide or polydeoxyribonucleotide, which may be unmodified RNA or DNA, or modified RNA or DNA. "Polynucleotides" include, without limitation single- and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus "polynucleotide" embraces chemically, enzymatically or metabolically modified forms of polynucleotides as typically found in nature, as well as the chemical forms of DNA and RNA characteristic of viruses and cells. "Polynucleotide" includes but is not limited to linear and end-closed molecules. "Polynucleotide" also embraces relatively short polynucleotides, often referred to as oligonucleotides.

"Polypeptides" refers to any peptide or protein comprising two or more amino acids joined to each other by peptide bonds or modified peptide bonds (i.e., peptide isosteres). "Polypeptide" refers to both short chains, commonly referred as peptides, oligopeptides or oligomers, and to longer chains generally referred to as proteins. As described above, polypeptides may contain amino acids other than the 20 gene-encoded amino acids.

As used herein the term "analogues" relates to mutants, variants, chimeras, fusions, deletions, additions and any other type of modifications made relative to a given polypeptide. The term "analogue" is synonym of homologue, derivative and chemical equivalent or biological equivalent.

As used herein, the term "homologous" sequence relates to nucleotide or amino acid sequence derived from the DNA sequence or polypeptide sequence of C3APL, C3APLT, C3APS, C3-TL, C3-TS, C3Basic1, C3Basic2 and C3Basic3.

As used herein, the term "heterologous" sequence relates to DNA sequence or amino acid sequence of a heterologous polypeptide and includes sequence other than that of C3APL, C3APLT, C3APS, C3-TL, C3-TS, C3Basic1, C3Basic2 and C3Basic3.

As used herein the term "basic amino acid rich region" relates to a region of a protein with a high content of the basic amino acids such as Arginine, Histidine, Asparagine, Glutamine, Lysine (Lys). A "basic amino acid rich region" may have, for example 15% or more (up to 100%) of basic amino acids. In some instance, a "basic amino acid rich region" may have less than 15% of basic amino acids and still function as a transport agent region. More preferably, a basic amino acid region will have 30% or more (up to 100%) of basic amino acids.

As used herein the term "proline rich region" refers to a region of a protein with 5% or more (up to 100%) of proline in its sequence. In some instance a "proline rich region" may have between 5% and 15% of prolines. Additionally, a "proline rich region" refers to a region, of a protein containing more prolines than what is generally observed in naturally occurring proteins (e.g., proteins encoded by the human genome). "Proline rich region" of the present invention function as a transport agent region.

As used herein the term "to help neuron make new connections with other cells" or "helping neurons to make new cell connection" means that upon treatment of cells (e.g., neuron(s)) or tissue with a drug delivery construct, a conjugate, a fusion-protein, a polypeptide or a pharmaceutical compositions of the present invention, neurons may grow (develop) for example new dendrite, new axon or new neurite (i.e., cell bud), or already existing dendrite(s), axon or neurite (i.e., cell bud) are induce to grow to a greater extent.

As used herein, the term "vector" refers to an autonomously replicating DNA or RNA molecule into which foreign DNA or RNA fragments are inserted and then propagated in a host cell for either expression or amplification of the foreign DNA or RNA molecule. The term "vector" comprises and is not limited to a plasmid (e.g., linearized or not) that can be used to transfer DNA sequences from one organism to another.

The term "pharmaceutically acceptable carrier" or "adjuvant" and "physiologically acceptable vehicle" and the like are to be understood as referring to an acceptable carrier or adjuvant that may be administered to a patient, together with a compound of this invention, and which does not destroy the pharmacological activity thereof. Further, as used herein "pharmaceutically acceptable carrier" or "pharmaceutical carrier" are known in the art and include, but are not limited to, 0.01–0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

As used herein, "pharmaceutical composition" means therapeutically effective amounts (dose) of the agent together with pharmaceutically acceptable diluents, preservatives, solubilizers, emulsifiers, adjuvant and/or carriers. A "therapeutically effective amount" as used herein refers to that amount which provides a therapeutic effect for a given condition and administration regimen. Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts). Solubilizing agents (e.g., glycerol, polyethylene glycerol), anti-oxidants (e.g., ascorbic acid, sodium metabisulfite), preservatives (e.g., thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils). Also comprehended by the invention are particulate compositions coated with polymers (e.g., poloxamers or poloxamines). Other embodiments of the compositions of the invention incorporate particulate forms protective coatings, protease inhibitors or permeation enhancers for various routes of administration, including parenteral, pulmonary, nasal and oral routes. In one embodiment the pharmaceutical composition is administered parenterally, paracancerally, transmucosally, transdermally, intramuscularly, intravenously, intradermally, subcutaneously, intraperitonealy, intraventricularly, intracranially intratumorally or more preferably, directly at a central nervous system (CNS) lesion site or a peripheral nervous system (PNS) lesion site.

In addition, the term "pharmaceutically effective amount" or "therapeutically effective amount" refers to an amount (dose) effective in treating a patient, having, for example, a nerve injury. It is also to be understood herein that a "pharmaceutically effective amount" may be interpreted as an amount giving a desired therapeutic effect, either taken into one dose or in any dosage or route or taken alone or in combination with other therapeutic agents. In the case of the present invention, a "pharmaceutically effective amount" may be understood as an amount of ADP-ribosyl transferase C3 or ADP-ribosyl transferase C3 analogues (e.g., fusion proteins) of the present invention which may for example, suppress (e.g., totally or partially) the inhibition of neuronal axon growth, facilitate axon growth, prevent cell apoptosis, suppress Rho activity, help regenerate injured axon, or which may help neurons to make new connections with other cells.

As may be appreciated, a number of modifications may be made to the polypeptides of the present invention, such as for example the active agent region (e.g., ADP-ribosyl transferase C3 or ADP-ribosyl transferase C3 analogue) or the transport agent region (e.g., a subdomain of HIV Tat protein, or a homeodomain of antennapedia) and fragments thereof without deleteriously affecting the biological activity of the polypeptides or fragments. Polypeptides of the present invention comprises for example, those containing amino acid sequences modified either by natural processes, such as posttranslational processing, or by chemical modification techniques which are known in the art. Modifications may occur anywhere in a polypeptide including the polypeptide backbone, the amino acid side-chains and the amino or carboxy termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslational natural processes or may be made by synthetic methods. Modifications comprise for example, without limitation, acetylation, acylation, addition of acetomidomethyl (Acm) group, ADP-ribosylation, amidation, covalent attachment to flavin, covalent attachment to a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation and ubiquitination (for reference see, Protein-structure and molecular proterties, $2^{nd}$ Ed., T. E. Creighton, W. H. Freeman and Company, New-York, 1993).

Other type of polypeptide modification may comprises for example, amino acid insertion (i.e., addition), deletion and substitution (i.e., replacement), either conservative or nonconservative (e.g., D-amino acids, desamino acids) in the polypeptide sequence where such changes do not substantially alter the overall biological activity of the polypeptide. Polypeptides of the present invention comprise for example, biologically active mutants, variants, fragments, chimeras, and analogues; fragments encompass amino acid sequences having truncations of one or more amino acids, wherein the truncation may originate from the amino terminus (N-terminus), carboxy terminus (C-terminus), or from the interior of the protein. Analogues of the invention involve an insertion or a substitution of one or more amino acids. Variants, mutants, fragments, chimeras and analogues may have the biological properties of polypeptides of the present invention which comprise for example (without being restricted to the present examples) to facilitate neuronal axon growth, to suppress the inhibition of neuronal axon growth, to facilitate neurite growth, to inhibit apoptosis, to treat nerve injury, to regenerate injured axon and/or to act as a Rho antagonist.

As it may be exemplified (Example 13: reverse Tat sequence), in some instance, the order of the amino acids in a particular polypeptide is not critical. As for the transport agent region described herein, the transport function of this region may be preserved even if the amino acids are not in their original (as it is found in nature) order (sequence).

Example of substitutions may be those, which are conservative (i.e., wherein a residue is replaced by another of the same general type). As is understood, naturally occurring amino acids may be sub-classified as acidic, basic, neutral and polar, or neutral and non-polar. Furthermore, three of the encoded amino acids are aromatic. It may be of use that encoded polypeptides differing from the determined polypeptide of the present invention contain substituted codons for amino acids, which are from the same group as that of the amino acid being replaced. Thus, in some cases, the basic amino acids Lys, Arg and His may be interchangeable; the acidic amino acids Asp and Glu may be interchangeable; the neutral polar amino acids Ser, Thr, Cys, Gln, and Asn may be interchangeable; the non-polar aliphatic amino acids Gly, Ala, Val, Ile, and Leu are interchangeable but because of size Gly and Ala are more closely related and Val, Ile and Leu are more closely related to each other, and the aromatic amino acids Phe, Trp and Tyr may be interchangeable.

It should be further noted that if the polypeptides are made synthetically, substitutions by amino acids, which are not naturally encoded by DNA may also be made. For example, alternative residues include the omega amino acids of the formula NH2(CH2)nCOOH wherein n is 2–6. These are neutral nonpolar amino acids, as are sarcosine, t-butyl alanine, t-butyl glycine, N-methyl isoleucine, and norleucine. Phenylglycine may substitute for Trp, Tyr or Phe; citrulline and methionine sulfoxide are neutral nonpolar, cysteic acid is acidic, and ornithine is basic. Proline may be substituted with hydroxyproline and retain the conformation conferring properties.

It is known in the art that mutants or variants may be generated by substitutional mutagenesis and retain the biological activity of the polypeptides of the present invention. These variants have at least one amino acid residue in the protein molecule removed and a different residue inserted in its place (one or more nucleotide in the DNA sequence is changed for a different one using known molecular biology techniques, giving a different amino acid upon translation of the corresponding messenger RNA to a polypeptide). For example, one site of interest for substitutional mutagenesis may include but are not restricted to sites identified as the active site(s), or immunological site(s). Other sites of interest may be those, for example, in which particular residues obtained from various species are identical. These positions may be important for biological activity. Examples of substitutions identified as "conservative substitutions" are shown in Table 1. If such substitutions result in a change not desired, then other type of substitutions, denominated "exemplary substitutions" in Table 1, or as further described herein in reference to amino acid classes, are introduced and the products screened.

In some cases it may be of interest to modify the biological activity of a polypeptide by amino acid substitution, insertion, or deletion. For example, modification of a polypeptide may result in an increase in the polypeptide's biological activity, may modulate its toxicity, may result in changes in bioavailability or in stability, or may modulate its immunological activity or immunological identity. Substantial modifications in function or immunological identity are accomplished by selecting substitutions that differ significantly in their effect on maintaining (a) the structure of the polypeptide backbone in the area of the substitution, for example, as a sheet or helical conformation. (b) the charge or hydrophobicity of the molecule at the target site, or (c) the bulk of the side chain. Naturally occurring residues are divided into groups based on common side chain properties:

(1) hydrophobic: norleucine, methionine (Met), Alanine (Ala), Valine (Val), Leucine (Leu), Isoleucine (Ile)
(2) neutral hydrophilic: Cysteine (Cys), Serine (Ser), Threonine (Thr)
(3) acidic: Aspartic acid (Asp), Glutamic acid (Glu)
(4) basic: Asparagine (Asn), Glutamine (Gln), Histidine (His), Lysine (Lys), Arginine (Arg)
(5) residues that influence chain orientation: Glycine (Gly), Proline (Pro); and
(6) aromatic: Tryptophan (Trp), Tyrosine (Tyr), Phenylalanine (Phe)

Non-conservative substitutions will entail exchanging a member of one of these classes for another.

TABLE 1

Preferred amino acid substitution

| Original residue | Exemplary substitution | Conservative substitution |
| --- | --- | --- |
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Asn, Gln, Lys, Arg | Arg |
| Ile (I) | Leu, Val, Met, Ala, Phe, norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala | Leu |
| Pro (P) | Gly | Gly |
| Ser (S) | Thr | Thr |
| Thr (T) | Ser | Ser |
| Trp (W) | Tyr | Tyr |
| Tyr (Y) | Trp, Phe, Thr, Ser | Phe |
| Val (V) | Ile, Leu, Met, Phe, Ala, norleucine | Leu |

Amino acids sequence insertions (e.g., additions) include amino and/or carboxyl-terminal fusions ranging in length from one residues to polypeptides containing a hundred or more residues, as well as intrasequence insertions of single or multiple amino acid residues. Other insertional variants include the fusion of the N- or C-terminus of the protein to a homologous or heterologous polypeptide forming a chimera. Chimeric polypeptides (i.e., chimeras, polypeptide analogue) comprise sequence of the polypeptides of the present invention fused to homologous or heterologous sequence. Said homologous or heterologous sequence encompass those which, when formed into a chimera with the polypeptides of the present invention retain one or more biological or immunological properties.

Other type of chimera generated by homologous fusion includes new polypeptides formed by the repetition of two or more polypeptides of the present invention. The number of repeat may be, for example, between 2 and 50 units (i.e., repeats). In some instance, it may be useful to have a new polypeptide with a number of repeat greater than 50. For example, it may be useful to fuse (using cross-linking techniques or recombinant DNA technology techniques) polypeptides such as C3APL, C3APLT, C3APS, C3-TL, C3-TS, C3Basic1, C3Basic2 and C3Basic3 either to themselves (e.g., C3APLT fused to C3APLT) or to another polypeptide of the present invention (e.g., C3APLT fused to C3APL).

In addition, a transport agent such as for example, a subdomain of HIV Tat protein, and a homeodomain of antennapedia may be repeated more than one time in a polypeptide comprising the ADP-ribosyl transferase C3 or ADP-ribosyl transferase C3 analogues. The transport agent region may be either at the amino-terminal region of an ADP-ribosyl transferase C3 or ADP-ribosyl transferase C3 analogues or at its carboxy-terminal region or at both regions. The repetition of a transport agent region may affect (e.g., increase) the uptake of the ADP-ribosyl transferase C3 or ADP-ribosyl transferase C3 analogues by a desired cell.

Heterologous fusion includes new polypeptides made by the fusion of polypeptides of the present invention with heterologous polypeptides. Such polypeptides may include but are not limited to bacterial polypeptides (e.g., betalactamase, glutathione-S-transferase, or an enzyme encoded by the *E.coli* trp locus), yeast protein, viral proteins, phage proteins, bovine serum albumin, chemotactic polypeptides, immunoglobulin constant region (or other immunoglobulin regions), albumin, or ferritin.

Other type of polypeptide modification includes amino acids sequence deletions (e.g., truncations). Those generally range from about 1 to 30 residues, more preferably about 1 to 10 residues and typically about 1 to 5 residues.

Mutants, Variants and Analogues Proteins

Mutant polypeptides will possess one or more mutations, which are deletions (e.g., truncations), insertions (e.g., additions), or substitutions of amino acid residues. Mutants can be either naturally occurring (that is to say, purified or isolated from a natural source) or synthetic (for example, by performing site-directed mutagenesis on the encoding DNA or made by other synthetic methods such as chemical synthesis). It is thus apparent that the polypeptides of the invention can be either naturally occurring or recombinant (that is to say prepared from the recombinant DNA techniques).

A protein at least 50% identical, as determined by methods known to those skilled in the art (for example, the methods described by Smith, T. F. and Waterman M. S. (1981) Ad. Appl.Math., 2:482–489, or Needleman, S. B. and Wunsch, C. D. (1970) J.Mol.Biol., 48: 443–453), to those polypeptides of the present invention, for example C3APL, C3APLT, C3APS, C3-TL, C3-TS, C3Basic1, C3Basic2 and C3Basic3 are included in the invention, as are proteins at least 70% or 80% and more preferably at least 90% identical to the protein of the present invention. This will generally be over a region of at least 5, preferably at least 20 contiguous amino acids.

"Variant" as the term used herein, is a polynucleotide or polypeptide. that differs from reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusion and truncations in the polypeptide encoded by the reference sequence, as discussed herein. A typical variant of a polypeptide differs in amino acid sequence from another, reference polypeptide. Generally, differences are limited so that the sequence of the reference polypeptide and the variant are closely similar overall and, in many regions, identical. A variant and reference polypeptide may differ in amino acid by one or more substitutions, additions, deletions, or any combination therefore. A substituted or inserted amino acid residue may or may not be one encoded by the genetic code. A variant polynuclotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

Amino acid sequence variants may be prepared by introducing appropriate nucleotide changes into DNA, or by in vitro synthesis of the desired polypeptide. Such variant include, for example, deletions, insertions, or substitutions of residues within the amino acid sequence. A combination of deletion, insertion and substitution can be made to arrive at the final construct, provided that the final protein product possesses the desired biological activity, or characteristics. The amino acid changes also may alter posttranslational processes such as changing the number or position of the glycosylation sites, altering the membrane anchoring characteristics, altering the intra-cellular location by inserting, deleting or otherwise affecting the transmembrane sequence of the native protein, or modifying its susceptibility to proteolytic cleavage.

Unless otherwise indicated, the recombinant DNA techniques utilized in the present invention are standard procedures, known to those skilled in the art. Example of such techniques are explained in the literature in sources such as J. Perbal, A Practical Guide to Molecular Cloning, John Wiley and Sons (1984), J. Sambrook et al., Molecular Cloning: A Laboratory Manual, Cold Spring Harbor Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1–4, IRL Press (1995 and 1996), and F. M. Ausubel et al. (editors), Current Protocols in Molecular Biology, Greene Pub. Associates and Wiley-Interscience (1988, including all updates until present) and are incorporated herein by reference.

It is to be understood herein, that if a "range" or "group of substances" is mentioned with respect to a particular characteristic (e.g. amino acid groups, temperature, pressure, time and the like) of the present invention, the present invention relates to and explicitly incorporates herein each and every specific member and combination of sub-ranges or sub-groups therein whatsoever. Thus, any specified range or group is to be understood as a shorthand way of referring to each and every member of a range or group individually as well as each and every possible sub-ranges or sub-groups encompassed therein; and similarly with respect to any sub-ranges or sub-groups therein. Thus, for example, with respect to a sequence comprising up to 50 base units it is to be understood as specifically incorporating herein each and every individual unit, as well as sub-range of units;

with respect to reaction time, a time of 1 minute or more is to be understood as specifically incorporating herein each and every individual time, as well as sub-range, above 1 minute, such as for example 1 minute, 3 to 15 minutes, 1 minute to 20 hours, 1 to 3 hours, 16 hours, 3 hours to 20 hours etc.;

with respect to polypeptides, a polypeptide analogue comprising a particular sequence and having an addition of at least one amino acid to its amino-terminus or to its carboxy terminus is to be understood as specifically incorporating each and every individual possibility, such as for example one, two, three, ten, eighteen, forty, etc.;

with respect to polypeptides, a polypeptide analogue having at least 90% of its amino acid sequence identical to a particular amino acid sequence is to be understood as specifically incorporating each and every individual possibility (excluding 100%), such as for example, a polypeptide analogue having 90%, 90.5%, 91%, 93.7%, 97%, 99%, etc., of its amino acid sequence identical to a particular amino acid sequence.

with respect to polypeptides, a polypeptide analogue having at least 70% of its amino acid sequence identical to a particular amino acid sequence is to be understood as specifically incorporating each and every individual possibility (excluding 100%), such as for example, a polypeptide analogue having 70%, 72.3%, 73%, 88.6%, 98% etc., of its amino acid sequence identical to a particular amino acid sequence.

with respect to polypeptides, a polypeptide analogue having at least 50% of its amino acid sequence identical to a particular amino acid sequence is to be understood as specifically incorporating each and every individual possibility (excluding 100%), such as for example, a polypeptide analogue having 50%, 54%, 66.7%, 70.2%, 84%, 93% etc., of its amino acid sequence identical to that particular amino acid sequence.

with respect to polypeptide, a polypeptide comprising at least one transport agent region is to be understood as specifically incorporating each and every individual possibility, such as for example a polypeptide having one, two, five, ten, etc., transport agent region.

and similarly with respect to other parameters such as low pressures, concentrations, elements, etc. . . .

It is also to be understood herein that "g" or "gm" is a reference to the gram weight unit; and that "C", or "° C." is a reference to the Celsius temperature unit.

TABLE 2

Abbreviations

| Abbreviation | Full name |
| --- | --- |
| C3 | ADP-ribosyl transferase C3 |
| NGF | Nerve growth factor |
| BDNF | Brain-derived neurotrophic factor |
| C. or °C. | Degree Celcius |
| ml | milliliter |
| μl or ul | microliter |
| μM or uM | micromolar |
| mM | millimolar |
| M | molar |
| N | normal |
| CNS | Central nervous system |
| PNS | Peripheral nervous system |
| HIV | Human immunodeficiency virus |
| HIV-1 | Human immunodeficiency virus type-1 |
| kDa | kilodalton |
| GST | Glutathione S-transferase |
| MTS | Membrane transport sequence |
| SDS-PAGE | Sodium dodecyl sulfte polyacrylamide gel electrophoresis |
| PBS | Phosphate buffered saline |
| U | unit |
| BBB | Basso, Beattie Breshnahan behavior recovery scale |
| IPTG | Isopropyl β-D-thiogalactopyranoside |
| rpm | Rotation per minutes |
| DTT | dithiothreitol |
| PMSF | Phenylmethylsulfonyl fluoride |
| NaCl | Sodium chloride |
| MgCl$_2$ | Magnesium chloride |

TABLE 2-continued

Abbreviations

| Abbreviation | Full name |
| --- | --- |
| HBSS | Hank's balanced salt solution |
| NaOH | Sodium hydroxide |
| CSPG | chondroitin sulfate proteoglycan |
| PKN | Protein kinase N |
| RSV | Rous sarcoma virus |
| MMTV | Mouse mammary tumor virus |
| LTR | Long terminal repeat |
| HL | Hind limb |
| FL | Fore limb |
| neo | neomycin |
| hygro | hygromycin |
| IN-1 | monoclonal antibody called IN-1 |
| ADP | Adenosine di-phosphate |
| ATP | Adenosine tri-phosphate |
| $^{32}$P | Isotope 32 of phosphorus |
| DHFR | Dihydrofolate reductase |
| PCR | Polymerase chain reaction |

The invention in particular provides C3-like proteins, which may have additional amino acids added to the carboxy terminal end of the C3 proteins. Examples of such proteins includes:

C3APL: (C3 antennapedia—long) created by annealing sequences from the antennapedia transcription factor to the 3' end of the sequence encoding C3 cDNA. The long antennapedia sequence of 60 amino acids containing the homeodomain of antennapedia, was used;

C3APLT: (C3 antennapedia—truncated) created by annealing sequences from the antennapedia transcription factor to the 3' end of the sequence encoding C3 cDNA. This clone with a frameshift mutation gives a proline-rich transport peptide with good transport activity. This sequence is truncated i.e. shorter than C3APL.

C3APS: A short 11 amino acid sequence of antennapedia that has transmembrane transport properties was fused to the carboxy terminal of C3 to create C3APS;

C3-TL: C3 Tat-long created by fusing amino acids 27 to 72 of Tat to the carboxy terminal of C3 protein;

C3-TS: C3 Tat-short created by fusing the amino acids YGRKRRQRR (SEQ ID NO:49) to the C3 protein;

C3Basic1 a random basic charge sequence added to the C-terminal of C3;

C3Basic2: a random basic charge sequence added to the C-terminal of C3;

C3Basic3: C3 Tat-short created by fusing the reverse sequence of Tat amino acids RRQRRKKR (SEQ ID NO:50) to the C3 protein.

It has been found that conjugates or fusion proteins (C3-like proteins) Rho antagonists of the present invention are effective to stimulate repair in the CNS after spinal cord injury. The increased cell permeability of new Rho antagonist (new chimeric C3) would now allow treatment of victims of stroke and neurodegenerative disease because Rho signaling pathway is important in repair after stroke (Hitomi, et al. (2000) 67: 1929–39. Trapp et al 2001. Mol.Cell. Neurosci. 17: 883–84). Treatment with Rho antagonists in the adhesive delivery system could be used to enhance the rate of axon growth in the PNS. Also, evidence in the literature now links Rho signaling with formation of Alzheimer's disease tangles through its ability to activate PKN which then phosphorylates tau and neurofilaments (Morissette, et al. (2000) 278: H1769–74., Kawamata, et al. (1998) 18: 7402–10., Amano, et al. (1996) 271: 648–50., Watanabe, et al. (1996) 271: 645–8.). Therefore, Rho antagonists are expected to be useful in the treatment of Alzheimer's disease. The new chimeric C3 drugs should be able to diffuse readily and therefore can promote repair for diseases that are neurodegenerative. Examples include, but are not limited to stroke, traumatic brain injury, Parkinson's disease, Alzheimer's disease and ALS. Moreover, it is now well established that Rho signaling antagonists are effective in the treatment of other diseases. These include, but are not limited to eye diseases such as glaucoma (Honjo, et al. (2001) 42: 137–44., Rao, et al. (2001) 42: 1029–1037.), cancer cell migration and metastasis (Sahai, et al. (1999) 9: 136–45., Takamura, et al. (2001) 33: 577–81., Imamura, et al. (2000) 91: 811–6.). The effect of the Rho signaling pathway on smooth muscle relaxation are well established. This has led to the identification of Rho signaling antagonists as effective in treatment of hypertension (Chitaley, et al. (2001) 3: 139–144., Somlyo (1997) 389: 908–911, Uehata, et al. (1997) 389: 990–994), asthma (Nakahara, et al. (2000) 389: 103–6., Ishizaki, et al. (2000) 57: 976–83), and vascular disease (Miyata, et al. (2000) 20: 2351–8., Robertson, et al. (2000) 131: 5–9.) as well as penile erectile dysfunction (Chitaley, et al. (2001) 7: 119–22.). Rho is also important as a cardioprotective protein (Lee et al. 2001. FASEB J. 15:1886–1894).

Rho GTPases include members of the Rho, Rac and Cdc42 family of proteins. Our invention concerns Rho family members of the Rho class. Rho proteins consist of different variants encoded by different genes. For example, PC-12 cells express RhoA, RhoB and RhoC (Lehmann et al 1999 supra); PC-12 cells: Pheochromocytom cell line (Greene A and Tischler, A S PNAS 73:2424 (1976). To inactivate Rho proteins inside cells, Rho antagonists of the C3 family type are effective because they inactivate all forms of Rho (e.g. RhoA, Rho B etc). In contrast, gene therapy techniques, such as introduction of a dominant negative RhoA family member into a diseased cell, will only inactivate that specific RhoA family member.

Recombinant C3 proteins, or C3 proteins that retain the ribosylation activity are also effective in our delivery system and are covered by this invention. In addition, Rho kinase is a well-known target for active Rho, and inactivating Rho kinase has the same effect as inactivating Rho, at least in terms of neurite or axon growth (Kimura and Schubert (1992) Journal of Cell Biology.116:777–783, Keino-Masu, et al. (1996) Cell.87:175–185, Matsui, et al. (1996) EMBO J.15:2208–2216, Matsui, et al. (1998) J. Cell Biol.140:647–657, Ishizaki (1997) FEBS Lett.404:118–124), the biological activity that concerns this invention.

The C3 polypeptides of the present invention include biologically active fragments and analogues of C3; fragments encompass amino acid sequences having truncations of one or more amino acids, wherein the truncation may originate from the amino terminus, carboxy terminus, or from the interior of the protein. Fragments containing Glu (173) of C3 are included in this invention (Saito et al. 1995. FEBS Lett. 371–105). Analogues of the invention involve an insertion or a substitution of one or more amino acids. Fragments and analogues will have the biological property of C3 that is capable of inactivating Rho GTPase on Asn(41) on Rho. Also encompassed by the invention are chimeric polypeptides comprising C3 amino acid sequences fused to heterologous amino acid sequences. Said heterologous sequences encompass those which, when formed into a chimera with C3 retain one or more biological or immunological properties of C3. A host cell transformed or transfected with nucleic acids encoding C3 protein or C3 chimeric protein are also encompassed by the invention. Any host cell which produces a polypeptide having at least one of the biological properties of C3 may be used. Specific examples include bacterial, yeast, plant, insect or mammalian cells. In addition, C3 protein may be produced in transgenic animals. Transformed or transfected host cells and transgenic animals are obtained using materials and methods that are routinely available to one skilled in the art. Host cells may contain nucleic acid sequences having the full-length gene for C3 protein including a leader sequence and a C-terminal membrane anchor sequence (see below) or, alternatively, may contain nucleic acid sequences lacking one or both of the leader sequence and the C-terminal membrane anchor sequence. In addition, nucleic acid fragments, variants and analogues which encode a polypeptide capable of retaining the biological activity of C3 may also be resident in host expression systems.

C3 is produced as a 26 kDa protein. The full length C3 protein inactivates Rho by ADP-ribosylating asparagine 41 of Rho A (Han et al. (2001) J. Mol. Biol. 305: 95). Truncated, elongated or altered C3 proteins or C3-derived peptides that retain the ability to ribosylate Rho are included in this invention and can be used to make fusion proteins. The crystal structure of C3 has been determined giving insight to elements of the C3 protein that could be changed without affecting ribosylating activity (Han et al. (2001) J. Mol. Biol. 305: 95).

The Rho antagonist that is a recombinant proteins can be made according to methods present in the art. The proteins of the present invention may be prepared from bacterial cell extracts, or through the use of recombinant techniques. In general, C3 proteins according to the invention can be produced by transformation (transfection, transduction, or infection) of a host cell with all or part of a C3-encoding DNA fragment in a suitable expression vehicle. Suitable expression vehicles include: plasmids, viral particles, and phages. For insect cells, baculovirus expression vectors are suitable. The entire expression vehicle, or a part thereof, can be integrated into the host cell genome. In some circumstances, it is desirable to employ an inducible expression vector.

Those skilled in the field of molecular biology will understand that any of a wide variety of expression systems can be used to provide the recombinant protein. The precise host cell used is not critical to the invention. The C3 and C3-like proteins may be produced in a prokaryotic host (e.g., *E. coli* or *B. subtilis*) or in a eukaryotic host (e.g., *Saccharomyces* or *Pichia*; mammalian cells, e.g., COS, NIH 3T3, CHO, BHK, 293, or HeLa cells; or insect cells).

Proteins and polypeptides may also be produced by plant cells. For plant cells viral expression vectors (e.g., cauliflower mosaic virus and tobacco mosaic virus) and plasmid expression vectors (e.g., Ti plasmid) are suitable. Such cells are available from a wide range of sources (e.g., the American Type Culture Collection, Rockland, Md.). The methods of transformation or transfection and the choice of expression vehicle will depend on the host system selected.

The host cells harboring the expression vehicle can be cultured in conventional nutrient media adapted as need for activation of a chosen gene, repression of a chosen gene, selection of transformants, or amplification of a chosen gene. One expression system is the mouse 3T3 fibroblast host cell transfected with a pMAMneo expression vector (Clontech, Palo Alto, Calif.). pMAMneo provides an RSV-LTR enhancer linked to a dexamethasone-inducible MMTV-LTR promotor, an SV40 origin of replication which allows replication in mammalian systems, a selectable neomycin gene, and SV40 splicing and polyadenylation sites. DNA encoding a C3 or C3-like protein would be inserted into the pMAMneo vector in an orientation designed to allow expression. The recombinant C3 or C3-like protein would be isolated as described below. Other preferable host cells that can be used in conjunction with the pMAMneo expression vehicle include COS cells and CHO cells (ATCC Accession Nos. CRL 1650 and CCL 61, respectively).

C3 polypeptides can be produced as fusion proteins. For example, expression vectors may be used to create lacz fusion proteins. The pGEX vectors can be used to express foreign polypeptides as fusion proteins with glutathione S-transferase (GST). In general, such fusion proteins are soluble and can be easily purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety. Another strategy to make fusion proteins is to use the His tag system.

In an insect cell expression system, Autographa californica nuclear polyhedrosis virus AcNPV), which grows in Spodoptera frugiperda cells, is used as a vector to express foreign genes. A C3 coding sequence can be cloned individually into non-essential regions (for example the polyhedrin gene) of the virus and placed under control of an AcNPV promoter, e.g., the polyhedrin promoter. Successful insertion of a gene encoding a C3 or C3-like protein (polypeptide) will result in inactivation of the polyhedrin gene and production of non-occluded recombinant virus (i.e., virus lacking the proteinaceous coat encoded by the polyhedrin gene). These recombinant viruses are then used to infect Spodoptera frugiperda cells in which the inserted gene is expressed (see, Lehmann et al for an example of making recombinant MAG protein).

In mammalian host cells, a number of viral-based expression systems can be utilized. In cases where an adenovirus is used as an expression vector, the C3 nucleic acid sequence can be ligated to an adenovirus transcription/translation control complex, e.g., the late promoter and tripartite leader sequence. This chimeric gene can then be inserted into the adenovirus genome by in vitro or in vivo recombination. Insertion into a non-essential region of the viral genome (e.g., region E1 or E3) will result in a recombinant virus that is viable and capable of expressing a C3 gene product in infected hosts.

Specific initiation signals may also be required for efficient translation of inserted nucleic acid sequences. These signals include the ATG initiation codon and adjacent sequences. In cases where an entire native C3 gene or cDNA, including its own initiation codon and adjacent sequences, is inserted into the appropriate expression vector, no additional translational control signals may be needed. In other cases, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators.

In addition, a host cell may be chosen which modulates the expression of the inserted sequences, or modifies and processes the gene product in a specific, desired fashion. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product can be used. Such mammalian host cells include, but are not limited to, CHO, VERO, BHK, HeLa, COS, MDCK, 293, 3T3, WI38, and in particular, choroid plexus cell lines.

Alternatively, a C3 protein can be produced by a stably-transfected mammalian cell line. A number of vectors suitable for stable transfection of mammalian cells are available to the public; methods for constructing such cell lines are also publicly available. In one example, cDNA encoding the C3 protein may be cloned into an expression vector that includes the dihydrofolate reductase (DHFR) gene. Integration of the plasmid and, therefore, the C3 or C3-like protein-encoding gene into the host cell chromosome is selected for by including 0.01–300 $\mu$M methotrexate in the cell culture medium (as described in Ausubel et al., supra). This dominant selection can be accomplished in most cell types. Recombinant protein expression may be increased by DHFR-mediated amplification of the transfected gene. Methods for selecting cell lines bearing gene amplifications are known in the art; such methods generally involve extended culture in medium containing gradually increasing levels of methotrexate. DHFR-containing expression vectors commonly used for this purpose include pCVSEII-DHFR and pAdD26SV(A). Any of the host cells described above or, preferably, a DHFR-deficient CHO cell line (e.g., CHO DHFR cells, ATCC Accession No. CRL 9096) are among the host cells preferred for DHFR selection of a stably-transfected cell line or DHFR-mediated gene amplification.

A number of other selection systems may be used, including but not limited to the herpes simplex virus thymidine kinase, hypoxanthine-guanine phosphoribosyltransferase, and adenine phosphoribosyltransferase genes can be employed in tk, hgprt, or aprt cells, respectively. In addition, gpt, which confer resistance to mycophenolic acid; neo, which confers resistance to the aminoglycoside G-418; and hygro, which confers resistance to hygromycin may be used.

Alternatively, any fusion protein can be readily purified by utilizing an antibody specific for the fusion protein being expressed. For example, a system described in Janknecht et al. (1981) Proc. Natl. Acad. Sci. USA 88, 8972, allows for the ready purification of non-denatured fusion proteins expressed in human cell lines. In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto Ni2+ nitriloacetic acid-agarose columns, and histidine-tagged proteins are selectively eluted with imidazole-containing buffers.

Alternatively, C3, C3-like protein or a portion (fragment) thereof, can be fused to an immunoglobulin Fc domain. Such a fusion protein can be readily purified using a protein A column.

To test Rho antagonists for activity, a tissue culture bioassay system was used. This bioassay is used to define activity of Rho antagonists that will be effective in promoting axon regeneration in spinal cord injury, stroke or neurodegenerative disease.

Neurons do not grow neurites on inhibitory myelin substrates. When neurons are placed on inhibitory substrates in tissue culture, they remain rounded. When an effective Rho antagonist is added, the neurons are able to grow neurites on myelin substrates. The time that it takes for neurons to growth neurites upon the addition of a Rho antagonist is the same as if neurons had been plated on growth permissive substrate such as laminin or polylysine, typically 1 to 2 days in cell culture. The results can be scored visually. If needed, a quantitative assessment of neurite growth can be performed. This involved measuring the neurite length in a) control cultures where neurons are plated on myelin substrates and left untreated b) in positive control cultures, such as neurons plated on polylysine c) or treating cultures with different concentrations of the test antagonist.

To test C3 in tissue culture, it has been found that the best concentration is 25–50 ug/ml. (Lehmann et al, 1999. J.Neurosci. 19: 7537–7547; Jin & Strittmatter, 1997. J. Neurosci. 17: 6256–6263). Thus, high concentrations of this Rho antagonist are needed as compared to the growth factors used to stimulate neurite outgrowth. Growth factors, such as nerve growth factor (NGF) are used at concentrations of 1–100 ng/ml in tissue culture. However, growth factors are not able to overcome growth inhibition by myelin. Our tissue culture experiments are all performed in the presence of the growth factor BDNF for retinal ganglion cells, or NGF for PC-12 cells. When growth factors have been tested in vivo, typically the highest concentrations possible are used, in the ug/ml range. Also they are often added to the CNS with the use of pumps for prolonged delivery (e.g. Ramer et al, supra). For in vivo experiments the highest concentrations possible was used when working with C3 stored as a frozen 1 mg/ml solution.

The Rho antagonist C3 is stable at 37° C. for at least 24 hours. The stability of C3 was tested in tissue culture with the following experiment. The C3 was diluted in tissue culture medium, left in the incubator at 37° C. for 24 hours, then added to the bioassay system described above, using retinal ganglion cells as the test cell type. These cells were able to extend neurites on inhibitory substrates when treated with C3 stored for 24 hours at 37° C. Therefore, the minimum stability is 24 hours. This is in keeping with the stability projection based on amino acid composition (see sequence data, below).

A compound can be confirmed as a Rho antagonist in one of the following ways:
a) Cells are cultured on a growth inhibitory substrate as above, and exposed to the candidate Rho antagonist;
b) Cells of step a) are homogenized and a pull-down assay is performed. This assay is based on the capability of GST-Rhotektin to bind to GTP-bound Rho. Recombinant GST-Rhotektin or GST rhotektin binding domain (GST-RBD) is added to the cell homogenate made from cells cultured as in a). It has been found that inhibitory substrates activate Rho, and that this activated Rho is pulled down by GST-RBD. Rho antagonists will block activation of Rho, and therefore, an effective Rho antagonist will block the detection of Rho when cell are cultured as described by a) above;
c) An alternate method for this pull-down assay would be to use the GTPase activating protein, Rho-GAP as bait in the assay to pull down activated Rho, as described (Diekmann and Hall, 1995. In Methods in Enzymology Vol. 256 part B 207–215).

Another method to confirm that a compound is a Rho antagonist is as follows: When added to living cells antagonists that inactivate Rho by ADP-ribosylation of the effector domain can be identified by detecting a molecular weight shift in Rho (Lehmann et al, 1999 supra). The molecular weight shift can be detected after treatment of cells with Rho antagonist by homogenizing the cells, separating the proteins in the cellular homogenate by SDS polyacrylamide gel electrophoresis. The proteins are transferred to nitrocellulose paper, then Rho is detected with Rho-specific antibodies by a Western blotting technique.

Another method to confirm that compound is a Rho-kinase antagonist is as follows:
a) Recombinant Rho kinase tagged with myc epitope tag, or a GST tag or any suitable tag is expressed in Hela cells or another suitable cell type by transfection;
b) The kinase is purified from cell homogenates by immunoprecipitation using antibodies directed against the specific tag (e.g., myc tag or the GST tag);
c) The recovered immunoprecipitates from b) are incubated with [$^{32}P$] ATP and histone type 2 as a substrate in the presence or absence of the Rho kinase inhibitor. In the absence of Rho kinase inhibitor activity, the Rho kinase phosphorylated histone. In the presence of Rho kinase inhibitor the phosphorylation activity of Rho kinase (i.e. phosphorylation of histone) is blocked, and as such identified the compound as a Rho kinase antagonist.

Turning now to the transport side of the conjugates of the present invention, known methods are available to add transport sequences that allow proteins to penetrate into the cell; examples include membrane translocating sequence (Rojas (1998) 16: 370–375), Tat-mediated protein delivery (Vives (1997) 272: 16010–16017), polyargine sequences (Wender et al. 2000, PNAS 24: 13003–13008) and antennapedia (Derossi (1996) 271: 18188–18193). Examples of known transport agents, moities, subdomains and the like are also shown for example in Canadian patent document no. 2,301,157 (conjugates containing homeodomain of antennapedia) as well as in U.S. Pat. Nos. 5,652,122, 5,670, 617, 5,674,980, 5,747,641, and 5,804,604 (conjugates containing amino acids of Tat HIV protein (hereinafter Tat HIV protein is sometimes simply referred to as Tat); the entire contents of each of these patent documents is incorporated herein by reference.

A 16 amino acid region of the third alpha-helix of antennapedia homeodomain has been shown to enable proteins (made as fusion proteins) to cross cellular membranes (PCT international publication number WO 99/11809 and Canadian application No.: 2,301,157 (Crisanti et al,) incorporated herein as references). Here we have generated fusion-proteins comprising C3 and having an antennapedia homeodomain sequence located at the carboxy-terminal end of the fusion-protein. The biological activity (e.g., promoting axon growth) of these fusion proteins was demonstrated on primary mammalian cells such as neurons. Similarly, HIV Tat protein was shown to be able to cross cellular membranes (Frankel A. D. et al., Cell, 55: 1189). We have shown here using a sequence spanning amino acid 27 to 72 of HIV Tat, that Tat-mediated delivery of biologically active C3 protein is possible in neuronal cells and more specifically, in primary neuronal cells.

In addition to HIV Tat and antennapedia-mediated transport of C3 proteins and analogs, new transport sequences (i.e., transport polypeptide moiety, transport agent region, etc.) are presented herein.

Several receptor-mediated transport strategies have been used to try and improve function of ADP ribosylases: these methods include fusing C2 and C3 sequences (Wilde, et al. (2001) 276: 9537–9542.) and use of receptor-mediated transport with the diphtheria toxin receptor (Aullo, et al. (1993) 12: 921–31; Boquet, P. et al. (1995) Meth. Enzymol. 256: 297–306).). These methods have not been demonstrated to dramatically increase the potency of C3. Moreover, these proteins require receptor-mediated transport. This means that the cells must express the receptor, and must express sufficient quantities of the receptor to significantly improve transport. Moreover, when C3 enters the cell by endocytosis, it will be locked within a membrane compartment, and therefore most of it will not be available to inactivate Rho. In the case of diphtheria toxin, not all cells express the appropriate receptor, limiting its potential use. The clinical importance for any of these has not been tested or shown. A C2/C3 fusion protein has also been made to try and improve the effectiveness of C3. In this case, the addition of a C2II binding protein to the tissue culture medium is needed, along with the C2-C3 fusion toxin to allow uptake of C3 by receptor-mediated endocytosis (Barthe et al. (1998) Infection and Immunity 66:1364). The disadvantage of this system is that much of the C3 in the cell will be restrained within a membrane compartment. More importantly, two different proteins must be added separately for transport to occur (Wahl et al. 2000. J. Cell Biol. 149:263), which make this system difficult to apply to in vivo for treatment of disease. Moreover, none of the methods to inactivate Rho with C3 or C3 analogues (C3-like protein) have been demonstrated to be sufficient to overcome growth inhibition in tissue culture, or to promote recovery after CNS damage in vivo.

One strategy which may be used in accordance with the present invention is to exploit the antennapedia homeodomain that is able to transport proteins across the plasma membrane by a receptor-independent mechanism (Derossi (1996) 271: 18188–18193); an alternate strategy is to exploit Tat-mediated delivery (Vives (1997) 272: 16010–16017, Fawell (1994) 91: 664–668, Frankel (1988) 55: 1189–1193).

The Antennapedia strategy has been used for protein translocation into neurons (Derossi (1996) 271: 18188–18193). Antennapedia has, for example, been used to transport biotin-labeled peptides in order to demonstrate the efficacy of the technique; see U.S. Pat. No. 6,080,724 (the entire contents of this patent are incorporated herein by reference). Antennapedia enhances growth and branching of neurons in vitro (Bloch-Gallego (1993) 120: 485–492). Homeoproteins are transcription factors that regulate development of body organization, and antennapedia is a Drosophila homeoprotein. Tat on the other hand is a regulatory protein from human immunodeficiency virus (HIV). It is a highly basic protein that is found in the nucleus and can transport reporter genes into cell. Moreover, Tat-linked proteins can penetrate cells after intraperitoneal injection, and it can even cross the blood brain barrier to enter cells within the brain (Schwarze, et al. (1999) 285: 1569–72).

Other transport sequences that have been tested in other contexts, (i.e., to show that they work through the use of reporter sequences), are known. One transport peptide, a 12 mer, AAVLLPVLLAAP (SEQ ID NO:5 1), is rich in proline. It was made as a GST-MTS fusion protein and is derived from the h region of the Kaposi FGF signal sequence (Royas et al. 1998 Nature Biotech. 16: 370–375. Another example is the sperm fertiline alpha peptide, HPIQIAAFLARIPPIS-SIGTCILK (SEQ ID NO:52) (This is reviewed in Pecheur, J. Sainte-Marie, A. Bienvenuje, D. Hoekstra. 1999. J. Membrane Biol. 167: 1–17). It must be noted however that the alpha helix-breaking propensity of proline (Pro) residues is not a general rule, since the putative, fusion peptide of sperm fertilin alpha displays a high alpha helical content in the presence of liposomes. However, the Pro-Pro sequence is required for efficient fusion properties of fertilin. The C3APLT fusion protein that we tested fits the requirement of having a two prolines for making an effective transport peptide. Therefore, proline-rich sequences and random sequences that have helix-breaking propensity that act as effective transporters would also be effective if fused to C3.

In the context of axon growth on inhibitory substrates, axon regeneration after injury, or axon regeneration in the brain or spinal cord, no method using these transport sequences has been devised. In particular, it should be noted that the ability of antennapedia to enhance growth was tested with neurons placed on laminin-coated coverslips. Laminin supports axon growth and overrides growth inhibition (David, et al. (1995) 42: 594–602) thus, it is not a suitable substrate to test the potential for regeneration. There is an enormous wealth of literature over the last 20 years on substances that promote axon growth under such favorable tissue culture conditions, but none of these has lead to clinical advances in the treatment of spinal cord injury. The effect of antennapedia was shown to act as similar to a growth factors. Growth factors do not overcome growth inhibition by CNS growth inhibitory substrates (Lehmann, et al. (1999) 19: 7537–7547, Cai, et al. (1999) 22: 89–101). Growth factors applied in vivo do not support regeneration, only sprouting (Schnell, et al. (1994) 367: 170–173).

The transport sequence may be added to the N-terminal (amino-terminal) sequence of the C3 protein. Alternatively, the transport sequence may be added on the C-terminal (carboxy-terminal) end of the C3 protein; because the C-terminal is already quite basic, this should enhance further the transport properties. This is likely one of the reasons that C3APLT shows activity in addition to its basic charge and the proline-rich sequences.

The new chimeric C3 may be used to treat spinal cord injury to promote functional repair. We have demonstrated that both C3APLT and C3APS can overcome growth inhibition on complex inhibitory substrates that include myelin and mixed chondroitin sulfate proteoglycans. Further, we demonstrate that C3APLT can promote functional recovery after application to injured spinal cord in adult mice. The new chimeric protein may be used to promote axon regeneration and reduce scarring after CNS injury. Scarring is a barrier to nerve regeneration.

The advantage of the new chimeric C3 is the ability to treat the injured axons after a significant delay between the injury and the treatment. Also, the new recombinant protein may be useful in the treatment of chronic injury. The chimeric C3 can also be used to treat neurodegenerative diseases such as Alzheimer's disease and Parkinson's disease where penetration of the Rho antagonist to the affected neuronal population is required for effective treatment. The chimeric C3 (fusion proteins) will also be of benefit for the treatment of stroke and traumatic brain injury. Moreover, much evidence suggests efficacy in the treatment of cancer cell migration. Rho antagonists are also useful in the treatment of disease involving smooth muscle, such as vascular disease, hypertension, asthma, and penile dysfunction.

For treatment of spinal cord injury, the conjugate Rho antagonists of the present invention may be used in conjunction with cell transplantation. Many different cell transplants have been extensively tested for their potential to promote regeneration and repair, including, but not restricted to, Schwann cells, fibroblasts modified to express growth factors, fetal spinal cord transplants, macrophages, embryonic or adult stem cells, and olfactory ensheathing glia. C3 fusion proteins may be used in conjunction with neurotrophins, apoptosis inhibitors, or other agents that prevent cell death. They may be used in conjunction with cell adhesion molecules such as L1, laminin, and artificial growth matrices that promote axon growth. The chimeric C3 constructs of the present invention may also be used in conjunction with the use of antibodies that block growth inhibitory protein substrates to promote axon growth. Examples of such antibody methods are the use of IN-1 or related antibodies (Schnell and Schwab (1990) 343: 269–272) or through the use of therapeutic vaccine approaches (Huang (1999) 24: 639–647).

BRIEF DESCRIPTION OF THE FIGURES

In drawings which illustrate example embodiments of the present invention:

FIG. 6 illustrates the effectiveness of C3APLT to stimulate axon regeneration of primary neurons;

FIG. 12 illustrates that C3APLT promotes neurite outgrowth from retinal neurons plated on inhibitory myelin or CSPG substrates. Retinal neurons plated on myelin (dark bars) or CSPG (dotted bars) substrates and treated with C3-05.

Referring to FIG. 1, PC-12 cells were plated on inhibitory myelin substrates (0). Unmodified C3 added to the tissue culture medium at concentration from 0.00025–50 ug/ml did not significantly improve neurite outgrowth over the untreated control (grey bars). C3 was only effective in stimulating neurite outgrowth for cells plated on myelin substrates after scrape—loading (black bars). This Figure demonstrates the limited or no penetration in cells when passively added to the tissue culture medium. Please see Example 4 below for techniques.

Referring to FIG. 2, this Figure provides a demonstration that C3APLT and C3APS, ADP ribosylate Rho. Western blot showing RhoA in untreated cells (lane 1), and cells treated with C3APLT (lane 2) or C3APS (lane 3). When Rho is ADP ribosylated by C3 it undergoes a molecular weight shift (Lehmann et al supra), as observed for lanes 2 and 3. Please see Example 4 below for techniques.

Referring to FIG. 3, this Figure shows intracellular activity after treatment with C3APLT. Detection that the new fusion C3 penetrates into the cells. Immunocytochemistry with anti-C3 antibody of PC-12 cells plated on myelin and treated with C3 (A) or C3APLT (13). Cells in A (FIG. 3A) are not immunoreactive because C3 has not penetrated into the cells. Cells in B (FIG. 3B) are immunoreactive and they are able to extend neurites on myelin substrates. Please see Example 4 below for techniques.

Turning to FIG. 4, this Figure shows that C3-antennapedia fusion proteins promote growth on inhibitory substrates. The percent of neurons that grow neurites was counted for each treatment. The dose response experiment shows that C3APLT and C3APS promote more neurite growth per cell than control PC-12 cells plated on myelin (0). PC-12 cells were plated on myelin and either scrape loaded with unmodified C3 (C3 50) left untreated (0) or treated with various concentrations of C3APLT. Compared to C3 used at 25 ug/ml, C3APS is effective at stimulating more cells to grow neurites at 0.0025 ug/ml, a dose 10,000× less. Please see Example 4 below for techniques.

FIG. 5 shows a dose-response experiment showing that C3APLT and C3APS elicit long neurites to grow when cells are plated on inhibitory substrates. The length of neurites was measured for each treatment. PC-12 cells were plated on myelin and either scrape loaded with unmodified C3 (C3 50) left untreated (0) or treated with various concentrations of C3APLT. Compared to C3 used at 25 ug/ml, C3APS is effective at stimulating more cells to longer neurite growth at 0.0025 ug/ml, a dose 10,000× less. Please see Example 4 below for techniques.

As may be seen FIG. 6 shows primary neurons growing on inhibitory substrates after treatment with C3APLT. Rat retinal ganglion cells were plated on myelin substrates and treated with different concentrations of C3APLT. Concentrations of 0.025 and above promoted significantly longer neurites. This dose is 1000× lower than that of C3 needed to promote growth on myelin.

Referring to FIG. 7, this Figure shows behavioral recovery after treatment of adult mice with C3APLT in a dose-response experiment. Mice received a dorsal hemisection of the spinal cord and were left untreated (transection), were treated with fibrin alone (fibrin) or were treated with fibrin plus C3APLT at the indicated concentrations given in ug/mouse. Each point represents one animal. The BBB score (see Example 6 for details) was assessed 24 hours after treatment. Animals treated with C3APLT exhibited a significant improvement in behavioral recovery compared to untreated animals. The effective dose of 0.5 $\mu$g is 100× less than unmodified C3 used (see previous experiment shown in Canadian patent application 2,325,842). Please see Example 6.

Referring to FIG. 8, this Figure shows promotion of axon growth by C3-Tat chimeric proteins. The dose-response experiment shows that C3-TS and C3-TL promote more neurite growth per cell than control PC-12 cells plated on myelin. PC-12 cells were plated on myelin and either scrape loaded with unmodified C3 (scrape load) left untreated (myelin) or treated with various concentrations of C3-TS (grey bars) or C3-TL (black bars). Compared to C3 used at 25 ug/ml, C3-TL is effective at stimulating more cells to grow neurites at 0.0025 ug/ml, a dose 10,000× less than C3.

Referring to FIGS. 9A and 9B, these Figures show axon regeneration in injured spinal cord, i.e. anatomical regeneration after treatment with C3APLT. Section of the spinal cord after anterograde labeling with horseradish peroxidase conjugated to wheat germ agglutinin (WGA-HRP). A) Sprouting of cut axons into the dorsal white matter. Arrows show regenerating axons distal to the lesion. B) Same section 3 mm from the lesion site. Arrows show regenerating axons.

Referring to FIG. 10, this Figure shows that C3-APLT protected neurons from cell death following spinal cord injury. Apoptotic (dying) cells were counted following TUNEL labeling (see Example 16) 2 mm rostral to the lesion (Rostral) at the lesion site (lesion) and 2 mm caudal to the lesion site (caudal). Bars show average counts of Tunel positive cells from 4 animals treated with fibrin only after spinal cord injury as control (white bars), or with C3APLT in fibrin at 1 μg (black bars). Treatment with C3APLT show significantly reduced numbers of Tunel-labeled cells (dying cells). Non-injured spinal cord samples were also processed and these spinal cords did not show Tunel labeling, as expected.

Referring to FIG. 11, this Figure shows that C3APLT and C3Basic3 promote rapid neurite outgrowth compared to untreated cells when cells are plated on plastic as part of a rapid bioassay (see Example 4).

Referring to FIGS. 12A and 12B, to further support the ability of C3-like chimeric proteins to promote neurite outgrowth on inhibitory substrates, we examined the response of primary cultures plated on inhibitory substrates to C3APLT treatment. Purified retinal ganglion cells (RGCs) were plated on myelin, or CSPG substrates and treated with varying concentrations of C3APLT. During the RGC dissection great care was taken in order to try to limit the amount of mechanical manipulation of the cells, however, the isolation protocol requires that some triturating take place in order to dissociate and separate the cells. When RGCs are plated on inhibitory substrates, they maintained a similar round appearance to PC-12 cells plated on myelin. Treatment of RGCs with C3APLT promoted neurite outgrowth and increased neurite length on both myelin and CSPG substrates. In contrast to the wide range of concentrations shown to be effective in other PC-12 experiments a narrower range of C3APLT treatment, 0.025 ug/ml to 50 ug/ml promoted neurite outgrowth and increased neurite length on myelin. In the case of RGCs plated on CSPG substrates, effective concentration ranges of 0.0025 ug/ml to 50 ug/ml were observed.

DETAILED DESCRIPTION

Figure 1:
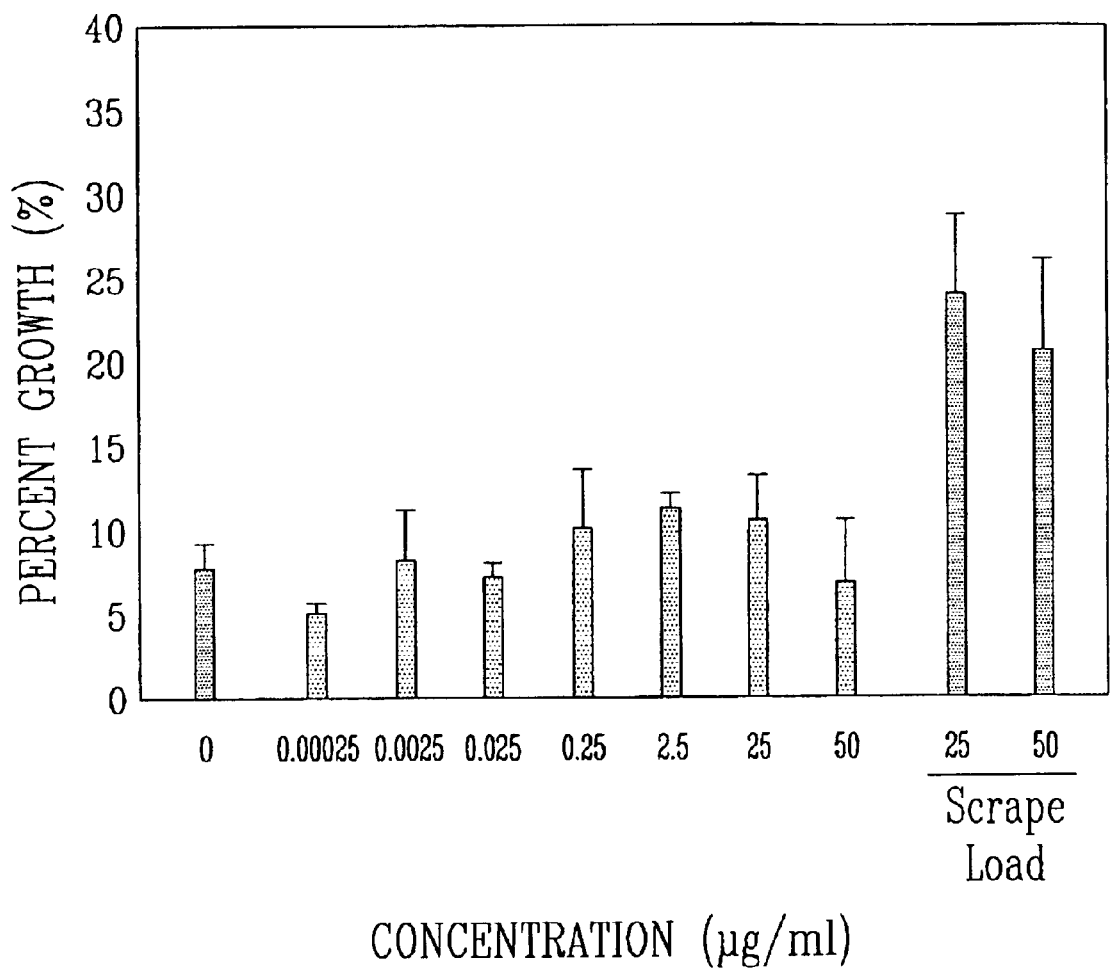
FIG. 1 illustrates the dose response of normal C3 with and without trituration.

Method for Making the C3APL, C3APLT, and C3APS

C3APL is the name given to the protein made by ligating a cDNA encoding C3 (Dillon and Feig (1995) 256: 174–184) with cDNA encoding the antennapedia homeodomain (Bloch-Gallego (1993) 120: 485–492). The stop codon at the 3' end of the DNA was replaced with an EcoR I site by polymerase chain reaction (PCR) using the primers (oligonucleotides) 5'GAA TTC TTT AGG ATT GAT AGC TGT GCC 3' (SEQ ID NO: 1) and 5'GGT GGC GAC CAT CCT CCA AAA 3' (SEQ ID NO: 2). The PCR product was sub-cloned into a pSTBlue-1 vector (Novagen, city), then cloned into a pGEX-4T vector using BamH I and Not I restriction site. This vector was called pGEX-4T/C3. The antennapedia sequence used to add to the 3' end of C3 in pGEX-4T/C3 was created by PCR from the pET-3a vector (Bloch-Gallego (1993) 120: 485–492, Derossi (1994) 269: 10444–10450), subcloned into a pSTBlue-1 blunt vector, then cloned into the pGEX-4T/C3, using the restriction sites EcoR I and Sal I, creating pGEX-4T/C3APL. Another clone (C3APLT) with a frameshift mutation was selected, and the protein made and tested. When the cultures tested positive despite the mutation, the clone was resequenced by another company to confirm the mutation, and this clone was called C3APLT. To confirm the sequence of C3APLT, the coding sequence from both strands was sequenced. The sequence for this clone is given in Examples 16 and 17 (nucleotide sequence of C3APLT; SEQ ID NO: 42, amino acid sequence of C3APLT; SEQ ID NO: 43).

A shorter version of the Antennapedia (pGEX-4T/C3APS) was also made. This chimeric sequence was made by ligating oligonucleotides encoding the short antennapedia peptide (Maizel (1999) 126: 3183–3190) into the pGEX-4T/C3 vector cut with EcoR I and Sal I. The recombinant C3APLT and C3APS cDNAs were separately transformed into bacteria, and after the recombinant proteins were produced, a bacterial homogenate was obtained by sonication, and the homogenate cleared by centrifugation. Glutathione-agarose beads (Sigma) were added to the cleared lysate and placed on a rotating plate for 2–3 hours, then washed extensively. To remove the glutathione S transferase sequence from the recombinant protein, 20 U (unit) of Thrombin was added, the beads were left on a rotator overnight at 4° C. After cleavage with thrombin, the beads were loaded into an empty 20 ml column, and the proteins eluted with PBS (phosphate buffered saline). Aliquots containing recombinant protein were pooled and 100 μl p-aminobenzamidine agarose beads (Sigma) were added and left mixing for 45 minutes at 4° C. to remove thrombin, then recombinant protein was isolated from the beads by centrifugation. Purity of the sample was determined by sodium dodecyl sulfate polyacrylamide gel electrophoresis (SDS-PAGE), and bioactivity bioassay with PC-12 cells was performed (See Lehmann et al supra).

Other possible methods for making bioactive chimeric proteins include anion exchange chromatography. For this, the GST tag is not required and can be removed. The cDNA can then be cloned into a high expression bacterial vector, such as pET, as given in Example 16.

The Rho antagonist is a recombinant protein and can be made according to methods present in the art. The proteins of the present invention may be prepared from bacterial cell extracts, or through the use of recombinant techniques by transformation, transfection, or infection of a host cell with all or part of a C3-encoding DNA fragment with an antennapedia-derived transport sequence in a suitable expression vehicle. Those skilled in the field of molecular biology will understand that any of a wide variety of expression systems can be used to provide the recombinant protein. The precise host cell used is not critical to the invention.

Any fusion protein can be readily purified by utilizing either affinity purification techniques or more traditional column chromatography. Affinity techniques include, but are not restricted to GST (gluathionie-S-transferase), or the use of an antibody specific for the fusion protein being expressed, or the use of a histidine tag. Alternatively, recombinant protein can be fused to an immunoglobulin Fc domain. Such a fusion protein can be readily purified using a protein A column. It is envisioned that small molecule mimetics of the above-described antagonists are also encompassed by the invention.

Testing the Bioactivity of C3APLT, C3APS, C3-TL and C3-TS

Figure 2:
FIG. 2 illustrates ADP ribosylation by C3APLT and C3APS, but not C3 after passively adding the compounds to PC-12 cells.
Figure 3A:
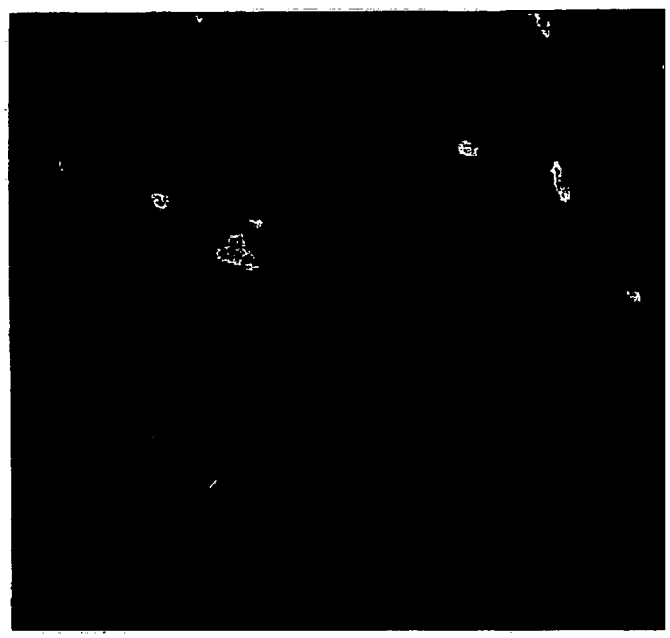
FIG. 3A illustrates that C3APLT penetrates cells.
Figure 3B:
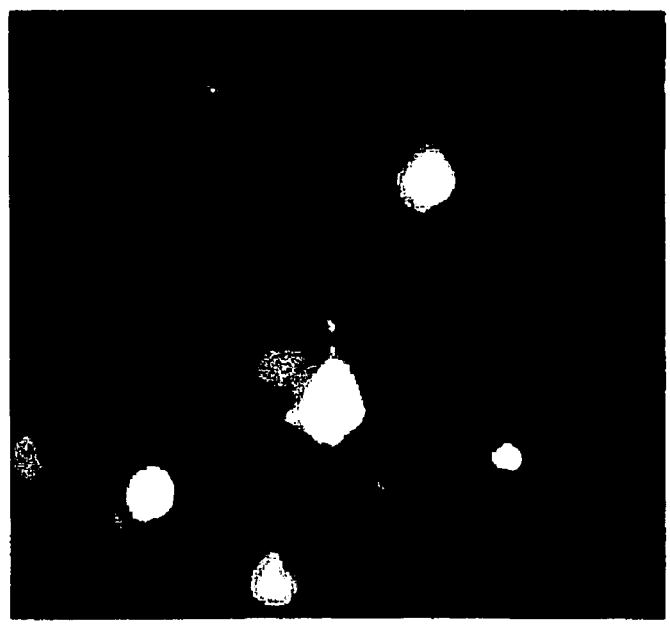
FIG. 3B illustrates a lower level of cell penetration by C3 as compared to FIG. 3A.
Figure 4:
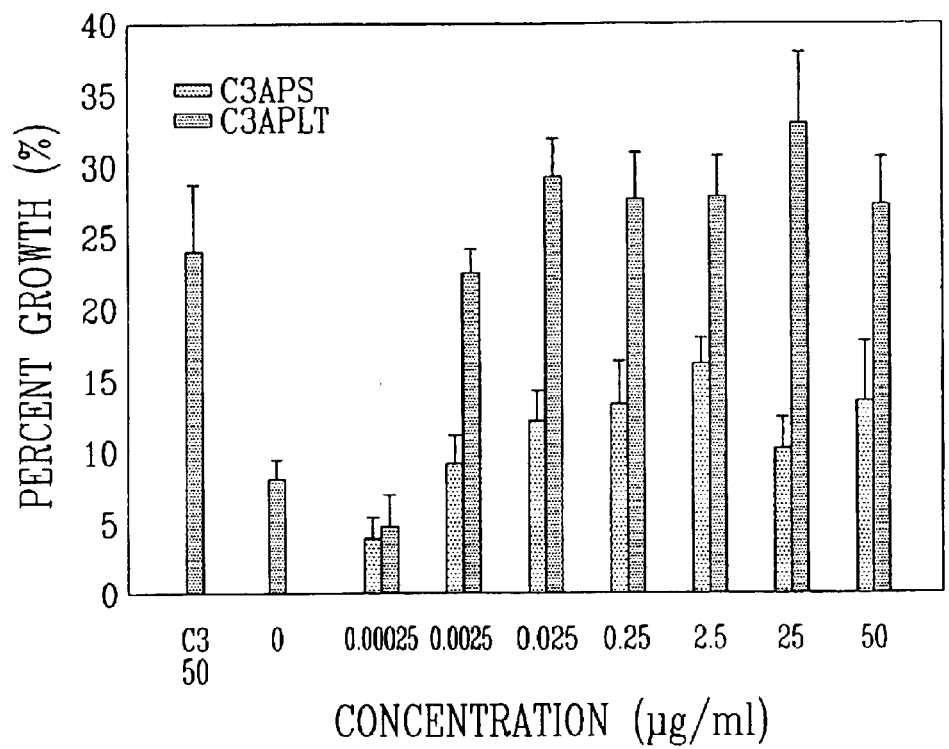
FIG. 4 illustrates the effectiveness of C3APLT and C3APS at low doses.
Figure 5:
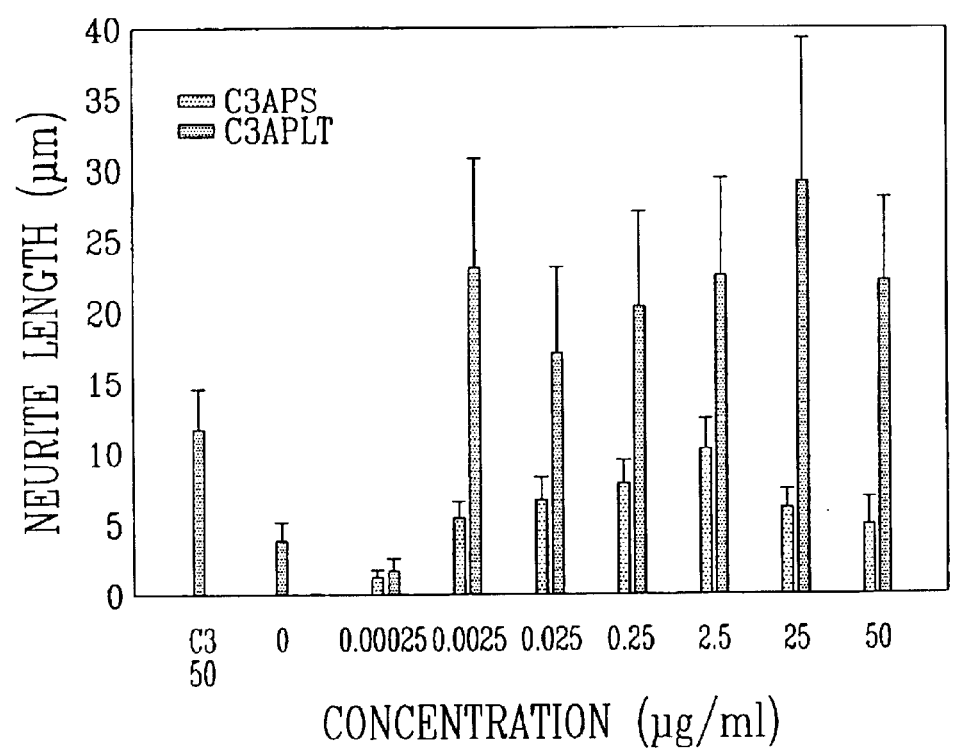
FIG. 5 illustrates the effectiveness of C3APLT and C3APS at low doses.
Figure 5:
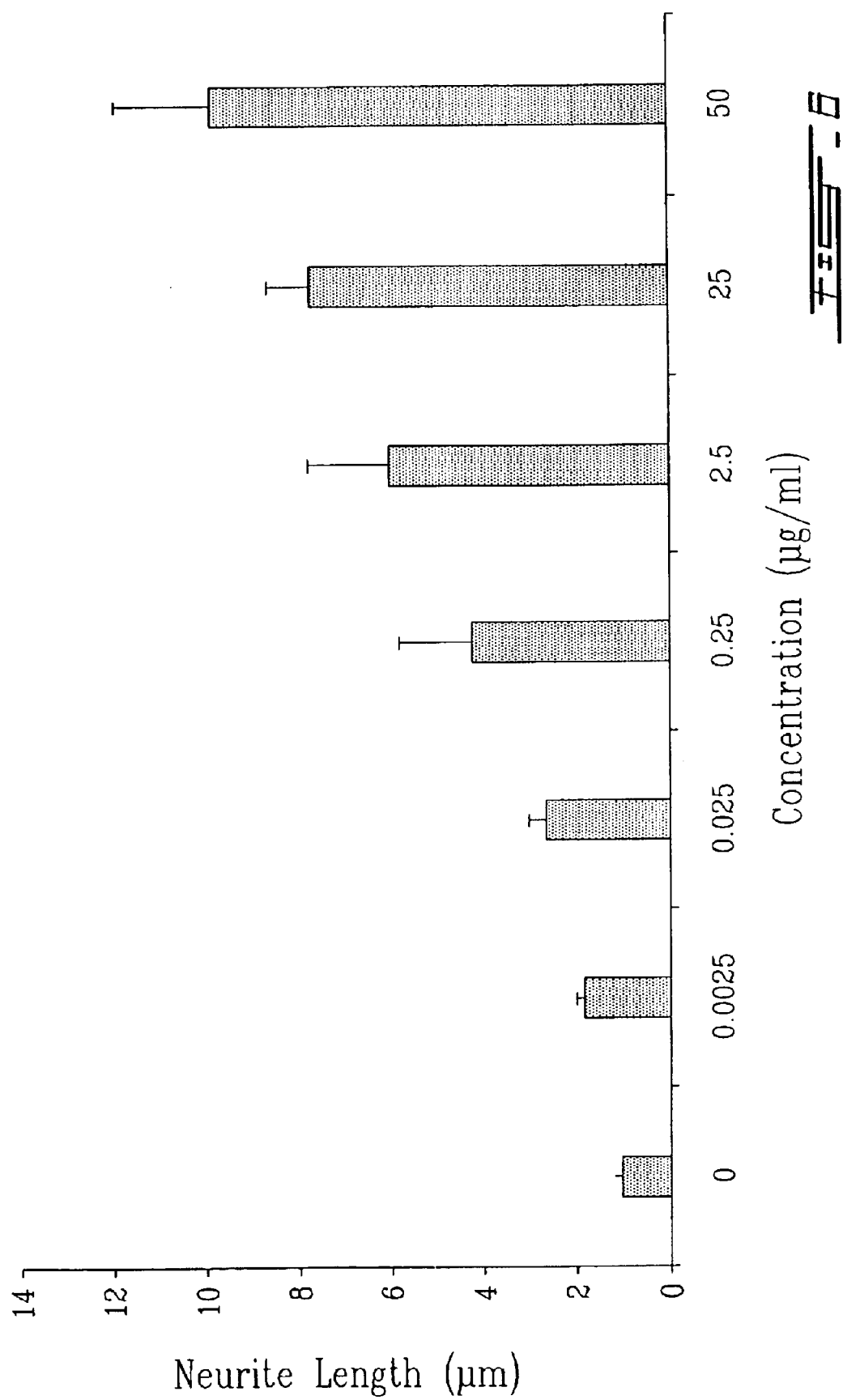

To test the efficacy of C3APLT, C3APS, C3-TL and C3-TS a number of experiments were performed with PC-12 cells, a neural cell line, grown on growth inhibitory substrates (see Lehmann et al supra). PC-12 cells were plated on myelin substrates as described (Lehmann et al, supra). C3, C3APLT, C3APS, C3-TL or C3-TS were added at different concentrations without trituration (please refer to FIGS. 4, 5 and 8 for concentrations used). C3 added passively to the culture medium in this way was not able to promote neurite growth in the growth inhibitory substrates because cells must be triturated for C3 to enter the cells and be active (FIG. 1). Both C3APLT and C3APS were able to ADP ribosylate Rho to cause a shift in the molecular weight of RhoA (FIG. 2). Both C3APLT and C3APS were able to promote neurite growth and enter neurons after being added passively to the culture medium (FIG. 3, FIGS. 4 and 5). Dose-response experiment where concentrations of 0.25 ng/ml, 2.5 ng/ml, 25 ng/ml, 250 ng/ml and 2.5 µg/ml and 25 µg/ml were tested and showed that C3APLT and C3APS helped more neurons differentiate neurites at doses 10,000 fold less than C3 (FIG. 4). Dose response experiments where concentrations of 0.25 ng/ml, 2.5 ng/ml, 25 ng/ml, 250 ng/ml and 2.5 µg/ml and 25 µg/ml were tested and showed that C3APLT was able to promote long neurite growth when added at a minimum concentration of 0.0025 ug/ml (FIG. 5). These concentrations of 2.5 ng/ml and 25 ng/ml for C3APLT and C3APS, represent 10,000 and 1,000 times less than the dose needed with C3, respectively. Moreover, at the highest concentration tested, 50 ug/ml, these two new Rho antagonists did not exhibit toxic effects on PC-12 cells, and were able to stimulate neurite outgrowth on growth inhibitory substrates.

Figure 8:
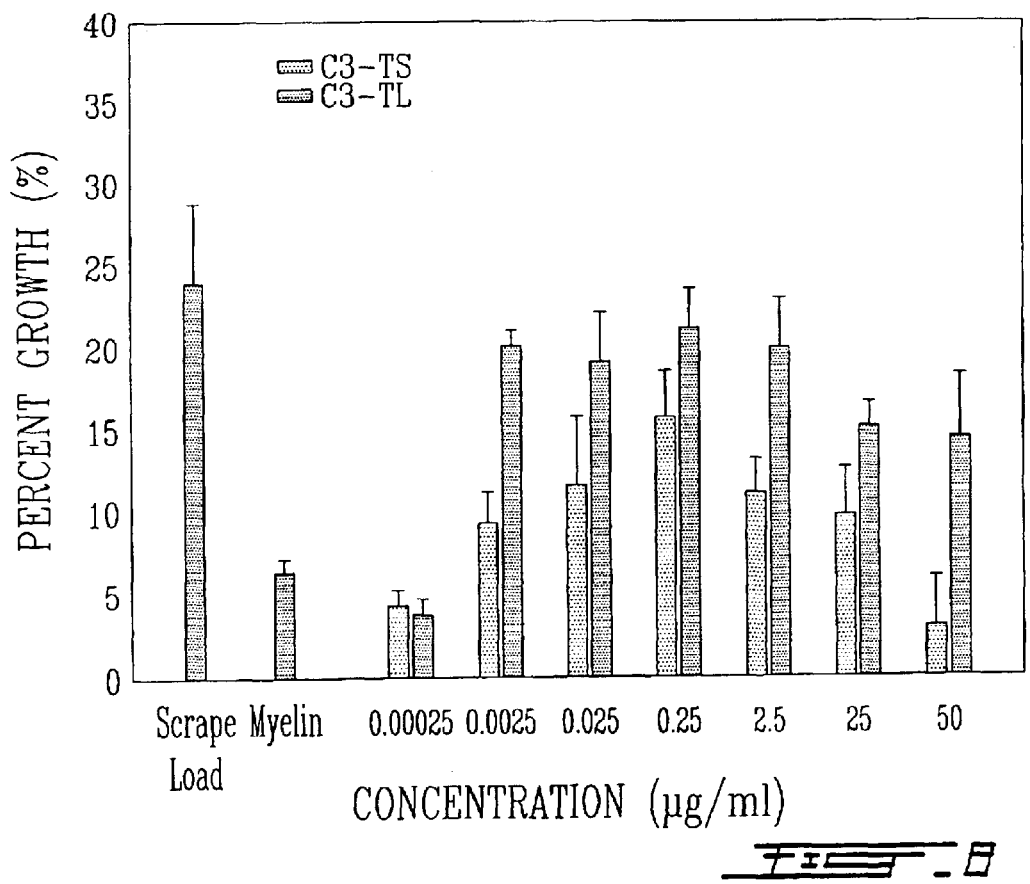
FIG. 8 illustrates effectiveness of Tat transport sequences to enhance growth as C3-Tat (C3-TL and C3-TS) chimeras.
Figure 9B:
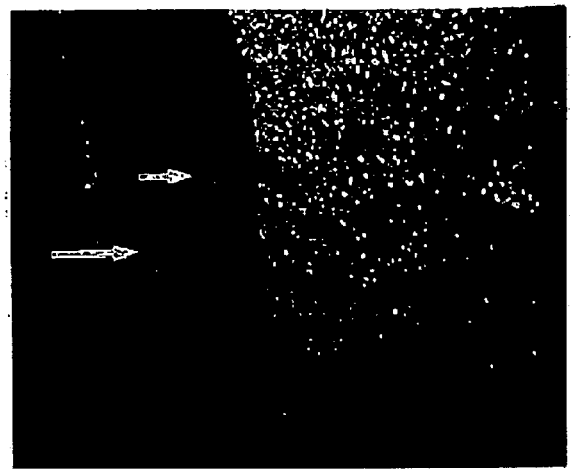
FIGS. 9A and 9B illustrate axon regeneration after spinal cord injury and treatment with C3APLT.
Figure 9A:
Figure 10:
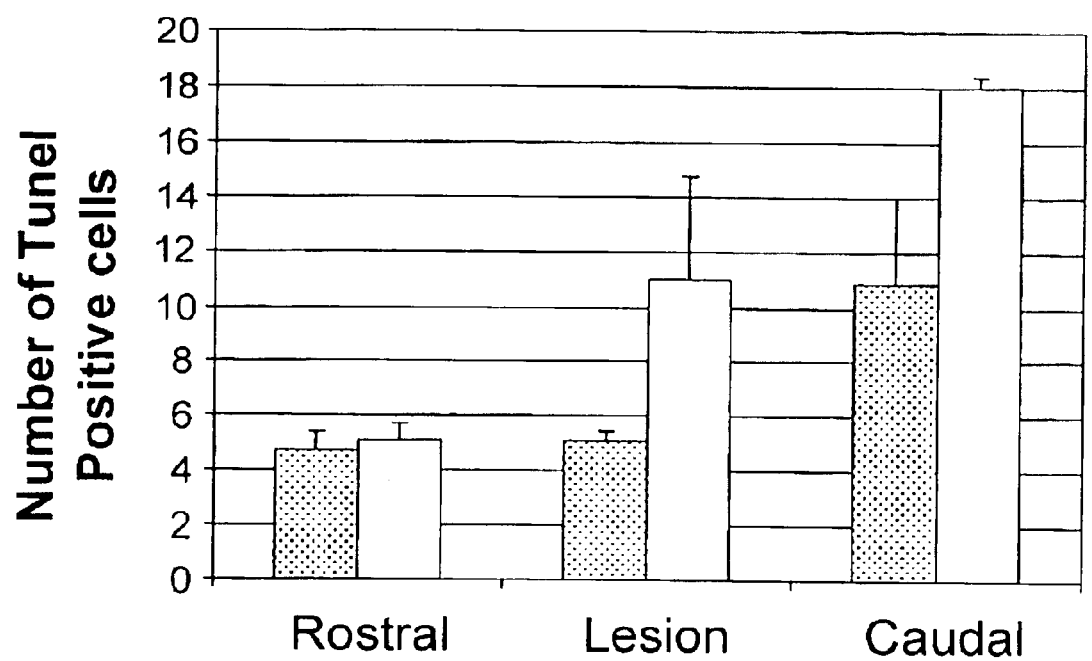
FIG. 10 illustrates effectiveness of C3APLT to prevent cell death after spinal cord injury, thereby showing that it is neuroprotective.
Figure 11:
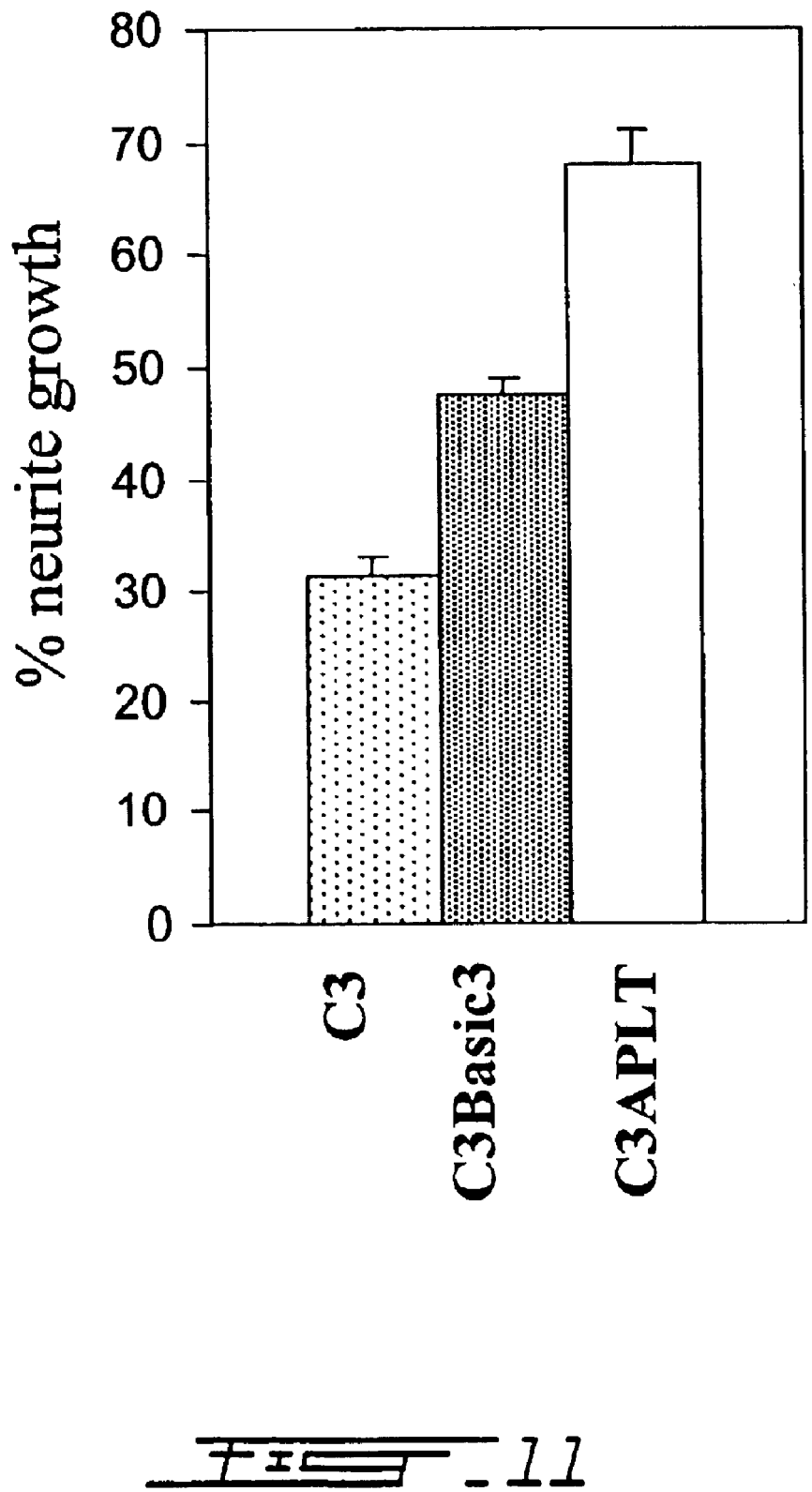
FIG. 11 illustrates a comparison of C3APLT and C3Basic3 to promote neurite outgrowth.

C3-TL and C3-TS also were tested at concentrations of 0.25 ng/ml, 2.5 ng/ml, 25 ng/ml, 250 ng/ml and 2.5 µg/ml and 25 µg/ml and were found to be able to promote neurite growth on myelin substrates at doses significantly less than C3 (FIG. 8). C3Basic3 was tested at 50 ug/ml in a fast growth assay (FIG. 11).

To verify the ability of C3APLT and C3APS to promote growth from primary neurons, primary retinal cultures were prepared, and the neurons were plated on myelin substrates as described with respect to Example 5. In the absence of treatment with C3APLT or C3APS, the cells remained round and were not able to grow neurites. When treated with C3APLT or C3APS, retinal neurons were able to extend long neurites on inhibitory myelin substrates (FIG. 6).

Figure 12A:
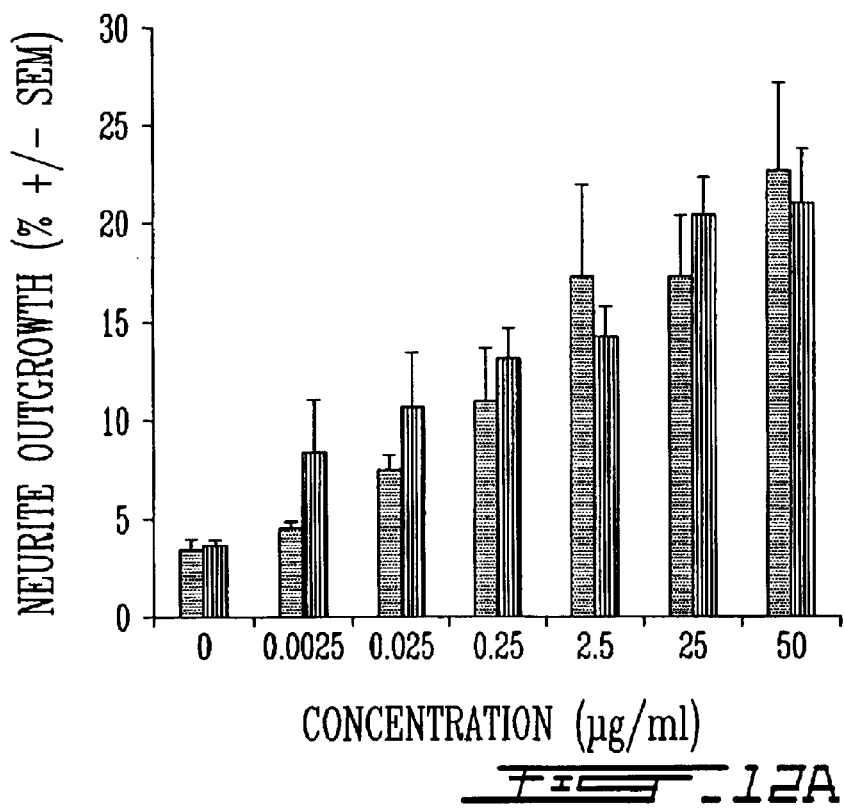
FIG. 12A illustrates the percentage of cells with neurites neurites longer than 1 cell body diameter (neurite outgrowth)
Figure 12B:
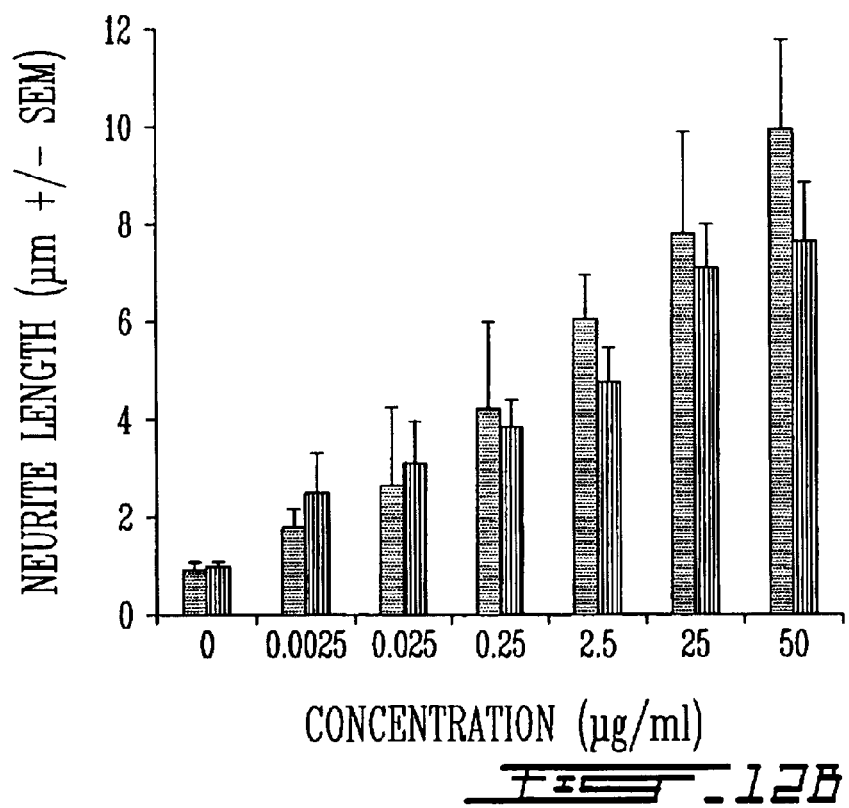
FIG. 12B illustrates the length of the longest neurite per cell (neurite length).

Next, was tested the ability of C3APLT and C3APS to promote growth on a different type of growth inhibitory substrate relevant to the type of growth inhibitory proteins found at glial scars. Chamber slides were coated with a mixture of chondroitin sulfate proteoglycans (Chemicon), and then plated with retinal neurons (results presented in FIG. 12). The neurons were not able to extend neurites on the proteoglycan substrates, but when treated with C3APLT or C3APS, they extended long neurites. These studies demonstrate that C3APLT and C3APS can be used to promote neurite growth on myelin and on proteoglycans, the major classes of inhibitory substrates that prevent repair after injury in the CNS.

Testing Ability of C3APLT to Promote Regeneration and Functional Recovery after Spinal Cord Injury To test if C3APLT could promote repair after spinal cord injury, fully adult mice were used (as described with respect to Example 6). A dorsal hemisection was made at T8 (thoracic spinal level 8), and mice were treated with different amounts (FIG. 7) of C3APLT in a fibrin glue as described (McKerracher, US patent pending (delivery patent)). In previous known experiments with C3, it was found that 40–50 µg was needed to promote anatomical regeneration in optic nerve (Lehmann et all supra). We tested different doses (see FIG. 7) of C3APLT ranging from 1 µg to 50 µg and assessed animals for behavioral recovery according the BBB scale (Basso (1995) 12: 1–21).

Figure 7:
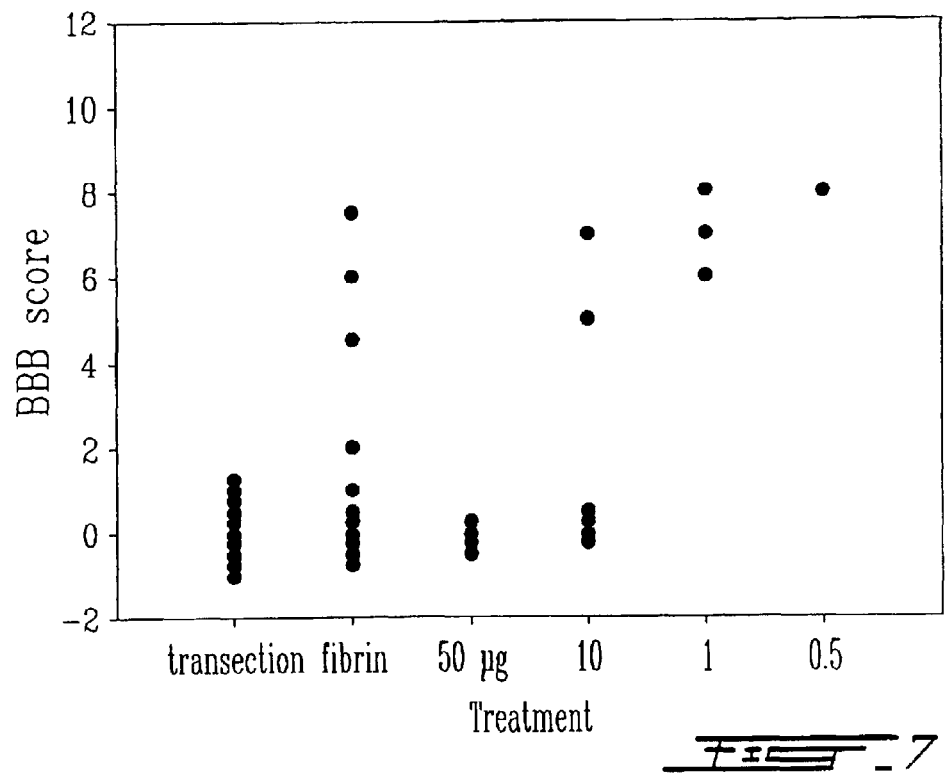
FIG. 7 illustrates the effectiveness of C3APLT to promote functional recovery after spinal cord injury.

The day following surgery and application of C3APLT, behavioral testing began. The animals were placed in an open field environment that consisted of a rubber mat approximately 4'×3' in size. The animals were left to move randomly, the movement of the animals were videotaped. For each test two observers scored the animals for ability to move ankle, knee and hip joints in the early phase of recovery. Previously C3 treatment of mice was seen to lead to functional recovery observable 24 hours after treatment. In mice treated with C3APLT, functional recovery could be observed as early as 24 hours after spinal cord injury (FIG. 7). Untreated mice exhibit a function recovery score according to the BBB scale averaging 0, whereas mice treated with C3 are able to walk and have a BBB score averaging 8 (FIG. 7). At higher concentrations of 50 ug, about 50% of the mice treated with C3APLT died within 24 hours. However, of the mice that survived, they exhibited good long-term functional recovery. These results demonstrate that C3APLT effectively promotes functional recovery early after spinal cord injury, and that it is effective at much lower doses than C3. However, at high concentrations, C3APLT appears to exhibit toxicity, and therefore careful doing will be required for clinical use.

Qualitative observations of the videotapes showed that only animals that received C3APLT reached the late phase of recovery after 30 days of treatment. Untreated control animals did not typically pass beyond the early phase of recovery. These results indicate that the application of C3APLT improved long-term functional recovery after spinal cord injury compared to no treatment, injury alone, or fibrin adhesive alone.

To test if the early recovery was due to neuroprotection, spinal cord sections were examined for apoptosis by Tunel labeling following manufacturer's instruction (Roche Diagnostic). C3APLT was able to reduce the number of dying cells observed at the lesion site. Therefore, C3APLT should be an effective neuroprotective agent for treatment of ischemia, such as follows stroke.

EXAMPLE 1

DNA and Protein Sequence Details of C3APL
Nucleotide Sequence of C3APL

It has been reported that the long version of antennapedia transport sequence can enhance neurite growth (Bloch-Gallego, E., LeRoux, I., Joliot, A. H., Volovitch, M., Henderson, C. E., Prochiantz, A. 1993. J. Cell Biol. 120:485). Therefore, this sequence is expected to enhance neurite growth. For the sequence given below, the start site, is in the GST sequence of the plasmid (not shown). The vector with the GST sequence is commercially available and thus the entire GST sequence including the start was not sequenced. It was desired to determine only the sequence located 3' to the thrombin cleavage site which releases C3 conjugate from the GST sequence. The GST sequence is cleaved with thrombin.

The APL transport sequence (SEQ ID NO.: 44) is as follows:

V M E S R K R A R Q T Y T R Y Q T L E L E K E F H F N-
R Y L T R R R R I E I A H A L C L T E R Q I K I W F Q N-
R R M K W K K E N

Nucleotide Sequence of C3APL (SEQ ID NO: 3)

5' GGA TCC TCT AGA GTC GAC CTG CAG GCA TGC AAT GCT

TAT TCC ATT AAT CAA AAG GCT TAT TCA AAT ACT TAC

CAG GAG TTT ACT AAT ATT GAT CAA GCA AAA GCT TGG

GGT AAT GCT CAG TAT AAA AAG TAT GGA CTA AGC AAA

-continued
```
TCA GAA AAA GAA GCT ATA GTA TCA TAT ACT AAA AGC

GCT AGT GAA ATA AAT GGA AAG CTA AGA CAA AAT AAG

GGA GTT ATC AAT GGA TTT CCT TCA AAT TTA ATA AAA

CAA GTT GAA CTT TTA GAT AAA TCT TTT AAT AAA ATG

AAG ACC CCT GAA AAT ATT ATG TTA TTT AGA GGC GAC

GAC CCT GCT TAT TTA GGA ACA GAA TTT CAA AAC ACT

CTT CTT AAT TCA AAT GGT ACA ATT AAT AAA ACG GCT

TTT GAA AAG GCT AAA GCT AAG TTT TTA AAT AAA GAT

AGA CTT GAA TAT GGA TAT ATT AGT ACT TCA TTA ATG

AAT GTC TCT CAA TTT GCA GGA AGA CCA ATT ATT ACA

CAA TTT AAA GTA GCA AAA GGC TCA AAG GCA GGA TAT

ATT GAC CCT ATT AGT GCT TTT CAG GGA CAA CTT GAA

ATG TTG CTT CCT AGA CAT AGT ACT TAT CAT ATA GAC

GAT ATG AGA TTG TCT TCT GAT GGT AAA CAA ATA ATA

ATT ACA GCA ACA ATG ATG GGC ACA GCT ATC AAT CCT

AAA GAA TTC GTG ATG GAA TCC CGC AAA CGC GCA AGG

CAG ACA TAC ACC CGG TAC CAG ACT CTA GAG CTA GAG

AAG GAG TTT CAC TTC AAT CGC TAC TTG ACC CGT CGG

CGA AGG ATC GAG ATC GCC CAC GCC CTG TGC CTC ACG

GAG CGC CAG ATA AAG ATT TGG TTC CAG AAT CGG CGC

ATG AAG TGG AAG AAG GAG AAC TGA 3'
```

Amino Acid Sequence of C3APL (SEQ ID NO: 4)

GSSRVDLQACNAYSINQKAYSNTYQEFTNIDQAKAWGNAQYKKYGLSKSE

KEAIVSYTKSASEINGKLRQNKGVINGFPSNLIKQVELLDKSFNKMKTPE

NIMLFRGDDPAYLGTEFQNTLLNSNGTINKTAFEKAKAKFLNKDRLEYGY

ISTSLMNVSQFAGRPIITQFKVAKGSKAGYIDPISAFQGQLEMLLPRHST

YHIDDMRLSSDGKQIIITATMMGTAINPKEFVMESRKRARQTYTRYQTLE

LEKEFHFNRYLTRRRRIEIAHALCLTERQIKIWFQNRRMKWKKEN

Physical Characteristics of C3APL
  Molecular Weight 34098.03 Daltons
  295 Amino Acids
  48 Strongly Basic(+) Amino Acids (K,R)
  28 Strongly Acidic(-) Amino Acids (D,E)
  89 Hydrophobic Amino Acids (A,I,L,F,W,V)
  94 Polar Amino Acids (N,C,Q,S,T,Y)
  9.847 Isoelectric Point
  20.524 Charge at PH 7.0
Davis, Botstein, Roth Melting Temp C. 79.48

EXAMPLE 2

DNA and Protein Sequence Details of C3APS

Nucleotide sequence of C3APS (SEQ ID NO: 5). The start site, is in the GST sequence of the plasmid, not shown here.

```
5' GGA TCC TCT AGA GTC GAC CTG CAG GCA TGC AAT GCT

TAT TCC ATT AAT CAA AAG GCT TAT TCA AAT ACT TAC

CAG GAG TTT ACT AAT ATT GAT CAA GCA AAA GCT TGG

GGT AAT GCT CAG TAT AAA AAG TAT GGA CTA AGC AAA

TCA GAA AAA GAA GCT ATA GTA TCA TAT ACT AAA AGC

GCT AGT GAA ATA AAT GGA AAG CTA AGA CAA AAT AAG

GGA GTT ATC AAT GGA TTT CCT TCA AAT TTA ATA AAA

CAA GTT GAA CTT TTA GAT AAA TCT TTT AAT AAA ATG

AAG ACC CCT GAA AAT ATT ATG TTA TTT AGA GGC GAC

GAC CCT GCT TAT TTA GGA ACA GAA TTT CAA AAC ACT

CTT CTT AAT TCA AAT GGT ACA ATT AAT AAA ACG GCT

TTT GAA AAG GCT AAA GCT AAG TTT TTA AAT AAA GAT

AGA CTT GAA TAT GGA TAT ATT AGT ACT TCA TTA ATG

AAT GTC TCT CAA TTT GCA GGA AGA CCA ATT ATT ACA

CAA TTT AAA GTA GCA AAA GGC TCA AAG GCA GGA TAT

ATT GAC CCT ATT AGT GCT TTT CAG GGA CAA CTT GAA

ATG TTG CTT CCT AGA CAT AGT ACT TAT CAT ATA GAC

GAT ATG AGA TTG TCT TCT GAT GGT AAA CAA ATA ATA

ATT ACA GCA ACA ATG ATG GGC ACA GCT ATC AAT CCT

AAA GAA TTC CGC CAG ATC AAG ATT TGG TTC CAG AAT

CGT CGC ATG AAG TGG AAG AAG GTC GAC TCG AGC GGC

CGC ATC GTG ACT GAC TGA 3'
```

The APS transport sequence (SEQ ID NO.: 45) is as follows:

RQIKIWFQNRRMKWKKVDS

Amino Acid Sequence for C3APS (SEQ ID NO: 6)

GSSRVDLQACNAYSINQKAYSNTYQEFTNIDQAKAWGNAQYKKYGLSKSE

KEAIVSYTKSASEINGKLRQNKGVINGFPSNLIKQVELLDKSFNKMKTPE

NIMLFRGDDPAYLGTEFQNTLLNSNGTINKTAFEKAKAKFLNKDRLEYGY

ISTSLMNVSQFAGRPIITQFKVAKGSKAGYIDPISAFQGQLEMLLPRHST

YHIDDMRLSSDGKQIIITATMMGTAINPKEFRQIKIWFQNRRMKWKKVDS

SGRIVTD

Physical Characteristics of C3APS
  Molecular Weight 29088.22 Daltons
  257 Amino Acids
  38 Strongly Basic(+) Amino Acids (K,R)
  23 Strongly Acidic(-) Amino Acids (D,E)
  79 Hydrophobic Amino Acids (A,I,L,F,W,V)
  83 Polar Amino Acids (N,C,Q,S,T,Y)
  9.745 Isoelectric Point
  15.211 Charge at PH 7.0
Davis, Botstein, Roth Melting Temp C. 78.34

EXAMPLE 3

Method for Making the C3APLT and C3APS Proteins

C3APL (amino acid sequence: SEQ ID NO.: 4) and C3APLT (amino acid sequence; SEQ ID NO: 37) are the names given to the proteins encoded by cDNAs made by ligating the functional domain of C3 transferase and the homeobox region of the transcription factor called antennapedia (Bloch-Gallego (1993) 120: 485–492) in the following way. A cDNA encoding C3 (Dillon and Feig (1995) 256: 174–184) cloned in the plasmid vector pGEX-2T was used for the C3 portion of the chimeric protein. The stop codon at the 3' end of the DNA was replaced with an EcoR I site by polymerase chain reaction using the primers 5'GAA TTC TTT AGG ATT GAT AGC TGT GCC 3' (SEQ ID NO: 1) and 5'GGT GGC GAC CAT CCT CCA AAA 3' (SEQ ID NO: 2). The PCR product was sub-cloned into a pSTBlue-1 vector (Novagen, city), then cloned into a pGEX-4T vector using BamH I and Not I restriction site. This vector was called pGEX-4T/C3. The pGEX-4T vector has a 5' glutathione S transferase (GST) sequence for use in affinity purification. The antennapedia sequence used to add to the 3' end of C3 in pGEX-4T/C3 was created by PCR from the pET-3a vector (Bloch-Gallego (1993) 120: 485–492, Derossi (1994) 269: 10444–10450). The primers used were 5'GAA TCC CGC AAA CGC GCA AGG CAG 3' (SEQ ID NO: 7) and 5'TCA GTT CTC CTT CTT CCA CTT CAT GCG 3' (SEQ ID NO: 8). The PCR product obtained from the reaction was sub-cloned into a pSTBlue-1 blunt vector, then cloned into the pGEX-4T/C3, using the restriction sites EcoR I and Sal I, creating pGEX-4T/C3APL and C3APLT. C3APLT was selected for the presence of a frameshift mutation giving a transport region moiety rich in prolines.

A shorter version of the antennapedia (pGEX-4T/C3AP-short) (amino acid sequence of C3APS; SEQ ID NO.: 6) was also made. This chimeric sequence was made by ligating oligonucleotides encoding the short antennapedia peptide (Maizel (1999) 126: 3183–3190) into the pGEX-4T/C3 vector cut with EcoR I and Sal I. For pGEX-4T/C3AP-short the sequences of the oligos made were 5'AAT TCC GCC AGA TCA AGA TTT GGT TCC AGA ATC GTC GCA TGA AGT GGA AGA AGG 3' (SEQ ID NO: 9) and 5'GGC GGT CTA GTT CTA AAC CAA GCT CTT AGC AGC GTA GTT CAC CTT CTT CCA GCT 3' (SEQ ID NO: 10). The two strands were annealed together by mixing equal amounts of the oligonucleotides, heating at 72° C. for 5 minutes and then leaving them at room temperature for 15 minutes. The oligonucleotides were ligated into the pGEX4T/C3 vector and clones were picked and analyzed.

To prepare recombinant C3APLT (SEQ ID NO.: 37) and C3APS (SEQ ID NO.: 6) proteins, the plasmids containing the corresponding cDNAs (pGEX-4T/C3APLT and pGEX-4T/C3AP-short) were transformed into bacteria, strain XL-1 blue competent *E. coli*. The bacteria were grown in L-broth (10 g/L Bacto-Tryptone, 5 g/L Yeast Extract, 10 g/L NaCl) with ampicillin at 50 ug/ml (BMC-Roche), in a shaking incubator for 1 hr at 37° C. and 300 rpm. Isopropyl β-D-thiogalactopyranoside (IPTG), (Gibco) was added to a final concentration of 0.5 mM to induce the production of recombinant protein and the culture was grown for a further 6 hours at 37° C. and 250 rpm. Bacteria pellets were obtained by centrifugation in 250 ml centrifige bottles at 7000 rpm for 6 minutes at 4° C. Each pellet was re-suspended in 10 ml of Buffer A (50 mM Tris, pH 7.5, 50 mM NaCl, 5 mM MgCl$_2$, 1 mM DTT) plus 1 mM PMSF. All re-suspended pellets were pooled and transferred to a 100 ml plastic beaker on ice. The remaining Buffer A with PMSF was added to the pooled sample. The bacteria sample was sonicated 6×20 seconds using a Branson Sonifier 450 probe sonicator. Both the bacteria and probe were cooled on ice 1 minute between sonications. The sonicate was centrifuged in a Sorvall SS-34 rotor at 16,000 rpm for 12 minutes at 4° C. to clarify the supernatant. The supernatant was transferred into fresh SS-34 tubes and re-spun at 12,000 rpm for 12 minutes at 4° C. Up to 20 ml of Glutathione-agarose beads (Sigma) were added to the cleared lysate and placed on a rotating plate for 2–3 hours. The beads were washed 4 times with buffer B, (Buffer A, NaCl is 150 mM, no PSMF) then 2 times with Buffer C (Buffer B+2.5 mM CaCl$_2$). The final wash was poured out till the beads created a thick slurry. To remove the glutathione S transferase sequence from the recombinant protein, 20 U of Thrombin (Bovine, Plasminogen-free, Calbiochem) was added, the beads were left on a rotator overnight at 4° C. After cleavage with thrombin the beads were loaded into an empty 20 ml column. Approximately 20 aliquots of 1 ml were collected by elution with PBS. Samples of each aliquot of 0.5 ul were spotted on nitrocellulose and stained with Amido Black to determine the protein peak. Aliquots containing fusion proteins were pooled and 100 µl p-aminobenzamidine agarose beads (Sigma) were added and left mixing for 45 minutes at 4° C. This last step removed the thrombin from the recombinant protein sample. The recombinant protein was centrifuged to remove the beads and then concentrated using a centriprep-10 concentrator (Amicon). The concentrated recombinant protein was desalted with a PD-10 column (Pharmacia, containing Sephadex G-25M) and ten 0.5 ml aliquots were collected. A dot-blot was done on these samples to determine the protein peak, and the appropriate aliquots pooled, filter-sterilized, and stored at −80° C. A protein assay (DC assay, Biorad) was used to determine the concentration of recombinant protein. Purity of the sample was determined by SDS-PAGE, and bioactivity bioassay with PC-12 cells.

EXAMPLE 4

Testing of Efficacy of C3APLT and C3APS in Tissue Culture

To test the ability of C3APLT and C3APS to overcome growth inhibition, PC-12 cells were plated on myelin, a growth inhibitory substrate. The myelin was purified from bovine brain (Norton and Poduslo (1973) 21: 749–757). In some other experiments chondroitin sulfate proteoglycan (CSPG) substrates were made from a purchased protein composition (Chemicon). Before coating coverslips or wells of a 96 well plate, they were coated with poly-L-lysine (0.025 µg/ml) (Sigma, St. Louis, Mo.), washed with water and allowed to dry. Myelin stored as a 1 mg/ml solution at −80° C. was thawed at 37° C., and vortexed. The myelin was plated at 8 ug/well in a 8 well chamber Lab-Tek slides (Nuc, Naperville, Ill.). The myelin solution was left to dry overnight in a sterile tissue culture hood. The next morning the substrate was washed gently with phosphate buffered saline, and then cells in media were added to the substrate. PC-12 cells (Lehmann et al., 1999) were grown in DMEM with 10% horse serum (HS) and 5% fetal bovine serum (FBS). Two days prior to use the PC-12 cells were differentiated by 50 ng/ml of nerve growth factor (NGF). After the cells were primed, 5 ml of trypsin was added to the culture dish to detach the cells, the cells were pelleted and re-suspended in 2 ml of DMEM with 1% HS and 50 ng/ml of nerve growth factor.

Approximately, 5000 to 7000 cells were then plated on 8 well chamber Lab-Tek slides (Nuc, Naperville, Ill.) coated myelin. The cells were placed on the test substrates at 37° C. for 3–4 hours to allow the cells to settle. The original media was carefully removed by aspiration, taking care not to disrupt the cells and replaced with DMEM with 1% HS, 50 ng/ml of NGF and varying amounts of the C3, C3APLT, or C3APS, depending on the dose desired. After two days, the cells were fixed (4% paraformaldehyde and 0.5% glutaraldehyde). For control experiments with unmodified C3, NGF primed PC-12 cells were trypsinized to detach them from the culture dish, the cells were washed once with scrape loading buffer (114 mM KCL, 15 mM NaCl, 5.5 mM $MgCl_2$, and 10 mM Tris-HCL) and then the cells were scraped with a rubber policeman into 0.5 ml of scraping buffer in the presence of 25 or 50 µg/ml of C3. The cells were pelleted and resuspended in 2 ml of DMEM, 1% HS and 50 ng/ml nerve growth factor before plating. At least four experiments were analyzed for each treatment. For each well, twelve images were collected with a 20× objective using a Zeiss Axiovert microscope. For each image, the numbers of cells with and without neurites were counted and the lengths of the neurites were determined. Since myelin is phase dense, cells plated on myelin substrates were immuno-stained with anti-βIII tubulin antibody before analysis. Quantitative analysis of neurite outgrowth was with the aid of Northern Eclipse software (Empix Imaging, Mississauga, Ontario, Canada). Data analysis and statistics were with Microsoft Excel.

For a fast bioassay, the compounds were tested in tissue culture as described above, except that the cells were plated on the tissue culture plastic rather than on inhibitory substrates. For these experiments the plates were fixed and the neurites counted five hours after plating the cells. The test compounds (C3APLT and C3Basic3) were able to promote faster growth on tissue culture plastic than cells plated without treatment (FIG. 11).

To examine ADP ribosylation by C3, C3APLT, and C3APS, the compounds were added to PC-12 cell cultures, as described above. The cells were harvested by centrifugation, cell homogenates prepared and the proteins separated by SDS polyacrylamide gel electrophoresis. The proteins were then transferred to nitrocellulose and the Western blots probed with anti-RhoA antibody (Santa Cruz).

EXAMPLE 5

Testing Ability of C3APLT and C3APS to Override Inhibition of Multiple Growth Inhibitory Proteins Myelin substrates were made as described in Example 4 and plated on tissue culture chamber slides. P1 to P3 rat pups were decapitated, the heads washed in ethanol and the eye removed and placed in a petri dish with Hanks buffered saline solution (HBSS, from Gibco). A hole was cut in the cornea, the lens removed, and the retina squeezed out. Typically, four retinas per preparation were used. The retinas were removed to a 15 ml tube and the volume brought to 7 ml. A further 7 ml of dissociation enzymes and papain were added. The dissociation enzyme solution was made as follows: 30 mg DL cysteine was added to a 15 ml tube (Sigma DL cystein hydrochloride), and 70 ml HBSS, 280 ul of 10 mg.ml bovine serum albumin were added and the solution mixed and pH adjusted to 7 with 0.3 N NaOH. The dissociate solution was filter-sterilized and kept frozen in 7 ml aliquots, and before use 12.5 units papain per ml (Worthington) was added. After adding the dissociation solution to the retina, the tube was incubated for 30 minutes on a rocking tray at 37° C. The retinas were then gently triturated, centrifuged and washed with HBSS. The HBSS was replaced with growth medium (DMEM (Gibco), 10% fetal bovine serum, and 50 ng/ml brain derived neurotrophic factor (BDNF) vitamins, penicillin-streptomycin, in the presence or absence of C3APLT or C3APS. Cells were plated on test substrates of myelin or CSPG in chamber slides prepared as described in Example 4, above. A quantitative analysis was completed as described for Example 4 above. Neurons were visualized by fluorescent microscopy with anti-βIII tubulin antibody, which detects growing retinal ganglion cells (RGCs). Results are presented in FIG. 6.

EXAMPLE 6

Treatment of Injured Mouse Spinal Cord with C3APLT and Measurement of Recovery of Motor Function in Treated Mice Adult Balb-c mice were anaesthetized with 0.6 ml/kg hypnorm, 2.5 mg/kg diazepam and 35 mg/kg ketamine. This does gives about 30 minutes of anaesthetic, which is sufficient for the entire operation. A segment of the thoracic spinal column was exposed by removing the vertebrae and spinus process with microrongeurs (Fine Science Tools). A spinal cord lesion was then made dorsally, extending past the central canal with fine scissors, and the lesion was recut with a fine knife. This lesion renders all of the control animals paraplegic. The paravertebral muscle were closed with reabsorbable sutures, and the skin was closed with 2.0 silk sutures. After surgery, the bladder was manually voided every 8–10 hours until the animals regained control, typically 2–3 days. Food was placed in the cage for easy access, and sponge-water used for easy accessibility of water after surgery. Also, animals received subcutaneous injection Buprenorphine (0.05 to 0.1 mg/kg) every 8–12 hours for the first 3 days. Any animals that lost 15–20% of body weight were killed.

Rho antagonists (C3 or C3-like proteins) were delivered locally to the site of the lesion by a fibrin-based tissue adhesive delivery system (McKerracher, Canadian patent application No. 2,325,842). Recombinant C3APLT was mixed with fibrinogen and thrombin in the presence of $CaCl_2$. Fibrinogen is cleaved by thrombin, and the resulting fibrin monomers polymerize into a three-dimensional matrix. We added C3APLT as part of a fibrin adhesive, which polymerized within about 10 seconds after being placed in the injured spinal cord. We tested C3APLT applied to the spinal cord lesion site after the lesion was made. For control we injected fibrin adhesive alone, or transected the cord without further treatment. For behavioral testing, the BBB scoring method was used to examine locomotion in an open field environment (Basso (1995) 12: 1–21). Results are presented in FIG. 7. The environment was a rubber mat approximately 4'×3' in size, and animals were placed on the mat and videotaped for about 4 minutes. Care was taken not to stimulate the peroneal region or touch the animals excessively during the taping session. The video tapes were digitized and observed by two observers to assign BBB scores. The BBB score, modified for mice, was as follows:

| Score | Description |
|---|---|
| 1 | No observable hindlimb (HL) movement. |
| 2 | Slight movement of one or two joints. |
| 3 | Extensive movement of one joint and/or slight movement of one other joint. |
| 4 | Extensive movement of two joints. |

-continued

| Score | Description |
|---|---|
| 5 | Slight movement of all three joints of the HL. |
| 6 | Slight movement of two joints and extensive movement of the third. |
| 7 | Extensive movement of two joints and slight movement of the third. |
| 8 | Extensive movement of all three joints of the HL walking with no weight support. |
| 9 | Extensive movement of all three joints, walking with weight support. |
| 10 | Frequent to consistent dorsal stepping with weight support. |
| 11 | Frequent plantar stepping with weight support. |
| 12 | Consistent plantar stepping with weight support, no coordination. |
| 13 | Consistent plantar stepping with consistent weight support, occasional FL-HL coordination. |
| 14 | Consistent plantar stepping with consistent weight support, frequent FL-HL coordination. |
| 15 | Consistent plantar stepping with consistent weight support, consistent FL-HL coordination; predominant paw position during locomotion is rotated internally or externally, or consistent FL-HL coordination with occasional dorsal stepping. |
| 16 | Consistent plantar stepping with consistent weight support, consistent FL-HL coordination; predominant paw position is parallel to the body; frequent to consistent toe drag, or curled toes, trunk instability. |
| 17 | Consistent plantar stepping with consistent weight support, consistent FL-HL coordination; predominant paw position is parallel to the body, no toe drag, some trunk instability. |
| 18 | Consistent plantar stepping with consistent weight support, consistent FL-HL coordination; predominant paw position is parallel to the body, no toe drag and consistent stability in the locomotion. |

EXAMPLE 7

Treatment of Injured Mouse Spinal Cord with C3APLT and Assessment of Anatomical Recovery Mice that received a spinal cord injury and treated as controls or with C3APLT, as described for Example 6 were assessed for morphological changes to the scar and for axon regeneration. To study axon regeneration, the corticospinal axons were identified by anterograde labeling. For anterograde labeling studies, the animals were anaesthetized as above, and the cranium over the motor cortex was removed. With the fine glass micropipetter (about 100 um in diameter) the cerebral cortex was injected with 2–4 ul of horse radish peroxidase conjugated to wheat germ agglutinin (2%), a marker that is taken up by nerve cells and transported anterogradely into the axon that extends into the spinal cord. After injection of the anterograde tracer, the cranium was replaced, and the skin closed with 5–0 silk sutures. The animals were sacrificed with chloral hydrate (4.9 mg/10 g) after 48 hours, and perfused with 4% paraformaldehyde in phosphate buffer as a fixative. The spinal cord was removed, cryoprotected with sucrose and cryostat sections placed on slides for histological examination.

EXAMPLE 8

DNA and Protein Sequence Details of C3-TL

The Tat coding sequence was obtained by polymerase chain reaction of the plasmid SVCMV-TAT (obtained form Dr. Eric Cohen, Universite de Montreal) that contains the entire HIV-1 Tat coding sequence. To isolate the transport sequence of the Tat protein, PCR was used. The first primer (5'GAATCCAAGCACCAGGAAGTCAGCC 3' (SEQ ID NO.: 11)) and the second primer (5' ACC AGCCACCAC-CTTCTGATA 3' (SEQ ID NO.: 12)) used corresponded to amino acids 27 to 72 of the HIV Tat protein. Upon verification and purification, the PCR product was sub cloned into a pSTBlue-1 blunt vector. This transport segment of the Tat protein was then cloned into pGEX-4T/C3 at the 3' end of C3, using the restriction sites EcoR I and Sac I. The new C3-Tat fusion protein was called C3-TL. Recombinant protein was made as described in Example 3.

DNA Sequence of C3-TL (SEQ ID NO.: 13)

5' GGA TCC TCT AGA GTC GAC CTG CAG GCA TGC AAT GCT

TAT TCC ATT AAT CAA AAG GCT TAT TCA AAT ACT TAC

CAG GAG TTT ACT AAT ATT GAT CAA GCA AAA GCT TGG

GGT AAT GCT CAG TAT AAA AAG TAT GGA CTA AGC AAA

TCA GAA AAA GAA GCT ATA GTA TCA TAT ACT AAA AGC

GCT AGT GAA ATA AAT GGA AAG CTA AGA CAA AAT AAG

GGA GTT ATC AAT GGA TTT CCT TCA AAT TTA ATA AAA

CAA GTT GAA CTT TTA GAT AAA TCT TTT AAT AAA ATG

AAG ACC CCT GAA AAT ATT ATG TTA TTT AGA GGC GAC

GAC CCT GCT TAT TTA GGA ACA GAA TTT CAA AAC ACT

CTT CTT AAT TCA AAT GGT ACA ATT AAT AAA ACG GCT

TTT GAA AAG GCT AAA GCT AAG TTT TTA AAT AAA GAT

AGA CTT GAA TAT GGA TAT ATT AGT ACT TCA TTA ATG

AAT GTC TCT CAA TTT GCA GGA AGA CCA ATT ATT ACA

CAA TTT AAA GTA GCA AAA GGC TCA AAG GCA GGA TAT

ATT GAC CCT ATT AGT GCT TTT CAG GGA CAA CTT GAA

ATG TTG CTT CCT AGA CAT AGT ACT TAT CAT ATA GAC

GAT ATG AGA TTG TCT TCT GAT GGT AAA CAA ATA ATA

ATT ACA GCA ACA ATG ATG GGC ACA GCT ATC AAT CCT

AAA GAA TTC AAG CAT CCA GGA AGT CAG CCT AAA ACT

GCT TGT ACC AAT TGC TAT TGT AAA AAG TGT TGC TTT

CAT TGC CAA GTT TGT TTC ATA ACA AAA GCC TTA GGC

ATC TCC TAT GGC AGG AAG CGG AGA CAG CGA CGA AGA

GCT CAT CAG AAC AGT CAG ACT CAT CAA GCT TCT CTA

TCA AAG CAG TAA 3'

The TL transport peptide sequence by itself is as follows: (SEQ ID NO.: 46)
KHPGSQPKTACTNCYCKKCCFHC-QVCFITKALGISYGRKRRQRRAHQN-SQTHQASLSKQ.

The Protein Sequence of C3-TL (SEQ ID NO.: 14)

GSSRVDLQACNAYSINQKAYSNTYQEFTNIDQAKAWGNAQYKKYGLSKSE

KEAIVSYTKSASEINGKLRQNKGVINGFPSNLIKQVELLDKSFNKMKTPE

NIMLFRGDDPAYLGTEFQNTLLNSNGTINKTAFEKAKAKFLNKDRLEYGY

ISTSLMNVSQFAGRPIITQFKVAKGSKAGYIDPISAFQGQLEMLLPRHST

YHIDDMRLSSDGKQIIITATMMGTAINPKEFKHPGSQPKTACTNCYCKKC

CFHCQVCFITKALGISYGRKRRQRRRAHQNSQTHQASLSKQ.

Molecular Weight 32721.40 Daltons
  291 Amino Acids
  43 Strongly Basic(+) Amino Acids (K,R)
  21 Strongly Acidic(-) Amino Acids (D,E)
  82 Hydrophobic Amino Acids (A,I,L,F,W,V)
  104 Polar Amino Acids (N,C,Q,S,T,Y)
  9.688 Isolectric Point
  22.655 Charge at PH 7.0
  Total Number of Bases Translated is 876

| % A = 37.44 | [328] |
| % G = 17.58 | [154] |
| % T = 28.31 | [248] |
| % C = 16.67 | [146] |

EXAMPLE 9

DNA and Protein Sequence Details of C3-TS

A shorter Tat construct was also made (C3-TS). To make the shorter C3 Tat fusion protein the following oligonucleotides were 5' AAT TCT ATG GTC GTA AAA AAC GTC GTC AAC GTC GTC GTG 3' (SEQ ID NO.: 15) and 5' GAT ACC AGC ATT TTT TGC AGC AGT TGC AGC AGC ACA GCT 3' (SEQ ID NO.: 16). The two oligonucleotide strands were annealed together by combining equal amounts of the oligonucleotides, heating at 72° C. for 5 minutes and then letting the oligonucleotide solution cool at room temperature for 15 minutes. The oligonucleotides were ligated into the pGEX4T/C3 vector at the 3' end of C3. The construct was sequenced. All plasmids were transformed into XL-1 blue competent cells. Recombinant protein was made as described in Example 3.

Nucleotide Sequence of C3-TS (SEQ ID NO.: 17)

```
5' GGA TCC TCT AGA GTC GAC CTG CAG GCA TGC AAT GCT
TAT TCC ATT AAT CAA AAG GCT TAT TCA AAT ACT TAC
CAG GAG TTT ACT AAT ATT GAT CAA GCA AAA GCT TGG
GGT AAT GCT CAG TAT AAA AAG TAT GGA CTA AGC AAA
TCA GAA AAA GAA GCT ATA GTA TCA TAT ACT AAA AGC
GCT AGT GAA ATA AAT GGA AAG CTA AGA CAA AAT AAG
GGA GTT ATC AAT GGA TTT CCT TCA AAT TTA ATA AAA
CAA GTT GAA CTT TTA GAT AAA TCT TTT AAT AAA ATG
AAG ACC CCT GAA AAT ATT ATG TTA TTT AGA GGC GAC
GAC CCT GCT TAT TTA GGA ACA GAA TTT CAA AAC ACT
CTT CTT AAT TCA AAT GGT ACA ATT AAT AAA ACG GCT
TTT GAA AAG GCT AAA GCT AAG TTT TTA AAT AAA GAT
AGA CTT GAA TAT GGA TAT ATT AGT ACT TCA TTA ATG
AAT GTC TCT CAA TTT GCA GGA AGA CCA ATT ATT ACA
CAA TTT AAA GTA GCA AAA GGC TCA AAG GCA GGA TAT
ATT GAC CCT ATT AGT GCT TTT CAG GGA CAA CTT GAA
ATG TTG CTT CCT AGA CAT AGT ACT TAT CAT ATA GAC
```

-continued
```
GAT ATG AGA TTG TCT TCT GAT GGT AAA CAA ATA ATA
ATT ACA GCA ACA ATG ATG GGC ACA GCT ATC AAT CCT
AAA GAA TTC TAT GGT GCT AAA AAA CGT CGT CAA CGT
CGT CGT GTC GAC TCG AGC GGC CCG CAT CGT GAC TGA 3'
```

The TS transport peptide sequence by itself is as follows: (SEQ ID NO.: 47)

YGAKKRRQRRRVDSSGPHRD

The Protein Sequence of C3-TS (SEQ ID NO.: 18)

GSSRVDLQACNAYSINQKAYSNTYQEFTNIDQAKAWGNAQYKKYGLSKSE
KEAIVSYTKSASEINGKLRQNKGVINGFPSNLIKQVELLDKSFNKMKTPE
NIMLFRGDDPAYLGTEFQNTLLNSNGTINKTAFEKAKAKFLNKDRLEYGY
ISTSLMNVSQFAGRPIITQFKVAKGSKAGYIDPISAFQGQLEMLLPRHST
YHIDDMRLSSDGKQIIITATMMGTAINPKEFYGAKKRRQRRRVDSSGPHR
D

Molecular Weight 26866.62 Daltons
  238 Amino Acids
  36 Strongly Basic(+) Amino Acids (K,R)
  21 Strongly Acidic(-) Amino Acids (D,E)
  71 Hydrophobic Amino Acids (A,I,L,F,W,V)
  78 Polar Amino Acids (N,C,Q,S,T,Y)
  9.802 Isolectric Point
  15.212 Charge at PH 7.0
Total Number of Bases Translated is 717

| % A = 38.91 | [279] |
| % G = 17.43 | [125] |
| % T = 28.45 | [204] |
| % C = 15.20 | [109] |

EXAMPLE 10

The following example illustrates how a coding sequence can be modified without affecting the efficacy of the translated protein. The example shows modifications to C3Basic3 that would not affect the activity. Sequences may include the entire GST sequence, as shown here that includes the start site, which would not be removed enzymatically. Also, the transport sequence shown in this example has changes in amino acid composition surrounding the active sequence due to a difference in the cloning strategy, and the His tag has been omitted. However, the active region is R R K Q R R K R R (SEQ ID NO:53). This sequence is contained in the C3Basic3, and is the active transport sequence in the sequence below. Also note that the C-terminal region of the protein after this active region differs from C3Basic3. That is because the cloning strategy was changed, the restriction sites differ, and therefore non-essential amino acids 3' terminal to the transport sequence are transplanted and included in the protein.

Nucleic Acid Sequence: (SEQ ID NO.: 19)
1413 base pairs
single strand
linear sequence

```
5' ATG TCC CCT ATA CTA GGT TAT TGG AAA ATT AAG GGC
CTT GTG CAA CCC ACT CGA CTT CTT TTG GAA TAT CTT
GAA GAA AAA TAT GAA GAG CAT TTG TAT GAG CGC GAT
GAA GGT GAT AAA TGG CGA AAC AAA AAG TTT GAA TTG
GGT TTG GAG TTT CCC AAT CTT CCT TAT TAT ATT GAT
GGT GAT GTT AAA TTA ACA CAG TCT ATG GCC ATC ATA
CGT TAT ATA GCT GAC AAG CAC AAC ATG TTG GGT GGT
TGT CCA AAA GAG CGT GCA GAG ATT TCA ATG CTT GAA
GGA GCG GTT TTG GAT ATT AGA TAC GGT GTT TCG AGA
ATT GCA TAT AGT AAA GAC TTT GAA ACT CTC AAA GTT
GAT TTT CTT AGC AAG CTA CCT GAA ATG CTG AAA ATG
TTC GAA GAT CGT TTA TGT CAT AAA ACA TAT TTA AAT
GGT GAT CAT GTA ACC CAT CCT GAC TTC ATG TTG TAT
GAC GCT CTT GAT GTT GTT TTA TAC ATG GAC CCA ATG
TGC CTG GAT GCG TTC CCA AAA TTA GTT TGT TTT AAA
AAA CGT ATT GAA GCT ATC CCA CAA ATT GAT AAG TAC
TTG AAA TCC AGC AAG TAT ATA GCA TGG CCT TTG CAG
GGC TGG CAA GCC ACG TTT GGT GGT GGC GAC CAT CCT
CCA AAA TCG GAT CTG GTT CCG CGT GGA TCC TCT AGA
GTC GAC CTG CAG GCA TGC AAT GCT TAT TCC ATT AAT
CAA AAG GCT TAT TCA AAT ACT TAC CAG GAG TTT ACT
AAT ATT GAT CAA GCA AAA GCT TGG GGT AAT GCT CAG
TAT AAA AAG TAT GGA CTA AGC AAA TCA GAA AAA GAA
GCT ATA GTA TCA TAT ACT AAA AGC GCT AGT GAA ATA
AAT GGA AAG CTA AGA CAA AAT AAG GGA GTT ATC AAT
GGA TTT CCT TCA AAT TTA ATA AAA CAA GTT GAA CTT
TTA GAT AAA TCT TTT AAT AAA ATG AAG ACC CCT GAA
AAT ATT ATG TTA TTT AGA GGC GAC GAC CCT GCT TAT
TTA GGA ACA GAA TTT CAA AAC ACT CTT CTT AAT TCA
AAT GGT ACA ATT AAT AAA ACG GCT TTT GAA AAG GCT
AAA GCT AAG TTT TTA AAT AAA GAT AGA CTT GAA TAT
GGA TAT ATT AGT ACT TCA TTA ATG AAT GTT TCT CAA
TTT GCA GGA AGA CCA ATT ATT ACA AAA TTT AAA GTA
GCA AAA GGC TCA AAG GCA GGA TAT ATT GAC CCT ATT
AGT GCT TTT CAG GGA CAA CTT GAA ATG TTG CTT CCT
AGA CAT AGT ACT TAT CAT ATA GAC GAT ATG AGA TTG
TCT TCT GAT GGT AAA CAA ATA ATA ATT ACA GCA ACA
ATG ATG GGC ACA GCT ATC AAT CCT AAA GAA TTC AGA
AGG AAA CAA AGA AGA AAA AGA AGA CTG CAG GCG GCC
GCA TCG TGA 3'
```

Amino Acid Sequence (SEQ ID NO: 20)
479 amino acids
linear, single strand

```
MSPILGYWKIKGLVQPTRLLLEYLEEKYEEHLYERDEGDKWRNKKFELGL
EFPNLPYYIDGDVKLTQSMAIIRYIADKHNMLGGCPKERAEISMLEGAVL
DIRYGVSRIAYSKDFETLKVDFLSKLPEMLKMFEDRLCHKTYLNGDHVTH
PDFMLYDALDVVLYMDPMCLDAFPKLVCFKKRIEAIPQIDKYLKSSKYIA
WPLQGWQATFGGGDHPPKSDLVPRGSSRVDLQACNAYSINQKAYSNTYQE
FTNIDQAKAWGNAQYKKYGLSKSEKEAIVSYTKSASEINGKLRQNKGVIN
GFPSNLIKQVELLDKSFNKMKTPENIMLFRGDDPAYLGTEFQNTLLNSNG
TINKTAFEKAKAKFLNKDRLEYGYISTSLMNVSQFAGRPIITKFKVAKGS
KAGYIDPISAFQGQLEMLLPRHSTYHIDDMRLSSDGKQIIITATMMGTAIN
PKEFRRKQRRKRRLQAAAS.
```

Molecular Weight 53813.02 Daltons
470 Amino Acids
68 Strongly Basic(+) Amino Acids (K,R)
55 Strongly Acidic(−) Amino Acids (D,E)
149 Hydrophobic Amino Acids (A,I,L,F,W,V)
121 Polar Amino Acids (N,C,Q,S,T,Y)
9.137 Isolectric Point
14.106 Charge at PH 7.0
Total Number of Bases Translated is 1413

| | |
|---|---|
| % A = 34.61 | [489] |
| % G = 19.75 | [279] |
| % T = 29.51 | [417] |
| % C = 15.99 | [226] |
| % Ambiguous = 0.14 | [2] |
| % A + T = 64.12 | [906] |
| % C + G = 35.74 | [505] |

Davis, Botstein, Roth Melting Temp C. 79.20

EXAMPLE 11

Additional Chimeric C3 Proteins that would be Effective to Stimulate Repair in the CNS The following sequences could be added to the amino terminal or carboxy terminal of C3 or a truncated C3 that retains its enzymatic activity.

1) Sequences of polyarginine as described (Wender, et al. (2000) 97: 13003–8.). These could be from 6 to 9 or more arginines.
2) Sequences of poly-lysine
3) Sequences of poly-histidine
4) Sequences of arginine and lysine mixed.
5) Basic stretches of amino acids containing non-basic amino acids stretch where the sequence added retains transport characteristics.
6) Sequences of 5–15 amino acids containing at least 50% basic amino acids 7) Sequences longer than 15–30 amino acids containing at least 30% basic amino acids.
8) Sequences longer than 50 amino acids containing at least 18% basic amino acids.
9) Any of the above where the amino acids are chemically modified, such as by addition of cyclohexyl side chains, other side chains, different alkyl spacers.
10) Sequences that have proline residues with helix-breaking propensity to act as effective transporters.

EXAMPLE 12

Additional Chimeric C3 Proteins that would be Effective to Stimulate Repair in the CNS C3Basic1: C3 fused to a randomly designed basic tail
C3Basic2: C3 fused to a randomly designed basic tail
C3Basic3: C3 fused to the reverse Tat sequence We have designed the following DNA encoding a chimeric C3 with membrane transport properties. The protein is designated C3Basic1. This sequence was designed with C3 fused to a random basic sequence. The construct was made to encode the peptide given below.

K R R R R R P K K R R R A K R R (SEQ ID NO.: 21)

The construct was made by synthesizing the two oligonucleotides given below, annealing them together, and ligating them into the pGEX-4T/C3 vector with an added histidine tag.

5' AAG AGA AGG CGA AGA AGA CCT AAG AAG AGA CGA AGG GCG AAG AGG AGA 3' (SEQ ID NO.: 22)

5'TTC TCT TCC GCT TCT TCT GGA TTC TTC TCT GCT TCC CGC TTC TCC TCT 3' (SEQ ID NO.: 23)

DNA Sequence of C3Basic1 (SEQ ID NO: 24)

```
5' GGA TCC TCT AGA GTC GAC CTG CAG GCA TGC AAT GCT
TAT TCC ATT AAT CAA AAG GCT TAT TCA AAT ACT TAC
CAG GAG TTT ACT AAT ATT GAT CAA GCA AAA GCT TGG
GGT AAT GCT CAG TAT AAA AAG TAT GGA CTA AGC AAA
TCA GAA AAA GAA GCT ATA GTA TCA TAT ACT AAA AGC
GCT AGT GAA ATA AAT GGA AAG CTA AGA CAA AAT AAG
GGA GTT ATC AAT GGA TTT CCT TCA AAT TTA ATA AAA
CAA GTT GAA CTT TTA GAT AAA TCT TTT AAT AAA ATG
AAG ACC CCT GAA AAT ATT ATG TTA TTT AGA GGC GAC
GAC CCT GCT TAT TTA GGA ACA GAA TTT CAA AAC ACT
CTT CTT AAT TCA AAT GGT ACA ATT AAT AAA ACG GCT
TTT GAA AAG GCT AAA GCT AAG TTT TTA AAT AAA GAT
AGA CTT GAA TAT GGA TAT ATT AGT ACT TCA TTA ATG
AAT GTT TCT CAA TTT GCA GGA AGA CCA ATT ATT ACA
AAA TTT AAA GTA GCA AAA GGC TCA AAG GCA GGA TAT
ATT GAC CCT ATT AGT GCT TTT CAG GGA CAA CTT GAA
ATG TTG CTT CCT AGA CAT AGT ACT TAT CAT ATA GAC
GAT ATG AGA TTG TCT TCT GAT GGT AAA CAA ATA ATA
ATT ACA GCA ACA ATG ATG GGC ACA GCT ATC AAT CCT
```

-continued

```
AAA GAA TTC AAG AGA AGG CGA AGA AGA CCT AAG AAG
AGA CGA AGG GCG AAG AGG AGA CAC CAC CAC CAC CAC
CAC GTC GAC TCG AGC GGC CGC ATC GTG ACT GAC TGA 3'
```

Protein Sequence of C3Basic1 (SEQ ID NO: 25)

```
GSSRVDLQACNAYSINQKAYSNTYQEFTNIDQAKAWGNAQYKKYGLSKSEK
EAIVSYTKSASEINGKLRQNKGVINGFPSNLIKQVELLDKSFNKMKTPENI
MLFRGDDPAYLGTEFQNTLLNSNGTINKTAFEKAKAKFLNKDRLEYGYIS
TSLMNVSQFAGRPIITKFKVAKGSKAGY-
IDPISAFQGQLEMLLPRHSTYHID
DMRLSSDGKQIIITATMMGTAINPKEFKRRRRRPKKRRRAKRRHHHHHHVD
SSGRIVTD.
```

Molecular Weight 29897.03 Daltons
263 Amino Acids
44 Strongly Basic(+) Amino Acids (K,R)
23 Strongly Acidic(−) Amino Acids (D,E)
75 Hydrophobic Amino Acids (A,I,L,F,W,V)
79 Polar Amino Acids (N,C,Q,S,T,Y)
10.024 Isolectric Point
22.209 Charge at PH 7.0
Davis, Botstein, Roth Melting Temp C. 78.56

EXAMPLE 13

Additional Chimeric C3 Protein that would be Effective to Stimulate Repair in the CNS We have designed the following DNA encoding a chimeric C3 with membrane transport properties. The protein is designated C3Basic2. This sequence was designed with C3 fused to a random basic sequence. The construct was made to encode the peptide given below.

K R R R R K K R R Q R R R(SEQ ID NO.:26)

The construct was made by synthesizing the two oligonucleotides given below, annealing them together, and ligating them into the pGEX4T/C3 vector with an added histidine tag.

5' AAG CGT CGA CGT AGA AAG AAA CGT AGA CAG CGT AGA CGT 3' (SEQ ID NO.: 27)

5'TTC GCA GCT GCA TCT TTC TTT GCA TCT GTC GCA TCT GCA 3' (SEQ ID NO.: 28)

DNA Sequence of C3Basic2 (SEQ ID NO.: 29)

```
5' GGA TCC TCT AGA GTC GAC CTG CAG GCA TGC AAT GCT
TAT TCC ATT AAT CAA AAG GCT TAT TCA AAT ACT TAC
CAG GAG TTT ACT AAT ATT GAT CAA GCA AAA GCT TGG
GGT AAT GCT CAG TAT AAA AAG TAT GGA CTA AGC AAA
TCA GAA AAA GAA GCT ATA GTA TCA TAT ACT AAA AGC
GCT AGT GAA ATA AAT GGA AAG CTA AGA CAA AAT AAG
GGA GTT ATC AAT GGA TTT CCT TCA AAT TTA ATA AAA
CAA GTT GAA CTT TTA GAT AAA TCT TTT AAT AAA ATG
```

-continued

```
AAG ACC CCT GAA AAT ATT ATG TTA TTT AGA GGC GAC

GAC CCT GCT TAT TTA GGA ACA GAA TTT CAA AAC ACT

CTT CTT AAT TCA AAT GGT ACA ATT AAT AAA ACG GCT

TTT GAA AAG GCT AAA GCT AAG TTT TTA AAT AAA GAT

AGA CTT GAA TAT GGA TAT ATT AGT ACT TCA TTA ATG

AAT GTT TCT CAA TTT GCA GGA AGA CCA ATT ATT ACA

AAA TTT AAA GTA GCA AAA GGC TCA AAG GCA GGA TAT

ATT GAC CCT ATT AGT GCT TTT CAG GGA CAA CTT GAA

ATG TTG CTT CCT AGA CAT AGT ACT TAT CAT ATA GAC

GAT ATG AGA TTG TCT TCT GAT GGT AAA CAA ATA ATA

ATT ACA GCA ACA ATG ATG GGC ACA GCT ATC AAT CCT

AAA GAA TTC AAG CGT CGA CGT AGA AAG AAA CGT AGA

CAG CGT AGA CGT CAC CAC CAC CAC CAC CAC GTC GAC

TCG AGC GGC CGC ATC GTG ACT GAC TGA 3'
```

Protein Sequence of C3Basic2 (SEQ ID NO.: 30)

GSSRVDLQACNAYSINQKAYSNTYQEFTNIDQAKAWGNAQYKKYGLSKSEK

EAIVSYIKSASEINGKLRQNKGVINGFPSNLIKQVELLDKSFNKMKTPEN

IMLFRGDDPAYLGTEFQNTLLNSNGTINKTAFEKAKAKFLNKDRLEYGYI

STSLMNVSQFAGRPIITKFKVAKGSKAGYIDPISAFQGQLEMLLPRHSTY

HIDDMRLSSDGKQIIITATMMGTAINPKEFKRRRRKKRRQRRRHHHHHHV

DSSGRIVTD.

Molecular Weight 29572.61 Daltons
260 Amino Acids
42 Strongly Basic(+) Amino Acids (K,R)
23 Strongly Acidic(−) Amino Acids (D,E)
74 Hydrophobic Amino Acids (A,I,L,F,W,V)
80 Polar Amino Acids (N,C,Q,S,T,Y)
9.956 Isoelectric Point
20.210 Charge at PH 7.0
Davis, Botstein, Roth Melting Temp C. 78.45

EXAMPLE 14

Additional Chimeric C3 Protein that would be Effective to Stimulate Repair in the CNS We have designed the following DNA encoding a chimeric C3 with membrane transport properties. The protein is designated C3Basic3. This sequence was designed with C3 fused to a reverse Tat sequence. The construct was made to encode the peptide given below

R R K Q R R K R R (SEQ ID NO.: 31)

The construct was made by synthesizing the two oligonucleotides given below, annealing them together, and ligating them into the pGEX4T/C3 vector with an added histidine tag, then subcloning in pGEX-4T/C3.

5' AGA AGG AAA CAA AGA AGA AAA AGA AGA 3' (SEQ ID NO.: 32)

5' TCT TCC TTT GTT TCT TCT TTT TCT TCT 3' (SEQ ID NO.: 33)

DNA Sequence of C3Basic3 (SEQ ID NO.: 34)

5' GGA TCC TCT AGA GTC GAC CTG CAG GCA TGC AAT GCT
TAT TCC ATT AAT CAA AAG GCT TAT TCA AAT ACT TAC
CAG GAG TTT ACT AAT ATT GAT CAA GCA AAA GCT TGG
GGT AAT GCT CAG TAT AAA AAG TAT GGA CTA AGC AAA
TCA GAA AAA GAA GCT ATA GTA TCA TAT ACT AAA AGC
GCT AGT GAA ATA AAT GGA AAG CTA AGA CAA AAT AAG
GGA GTT ATC AAT GGA TTT CCT TCA AAT TTA ATA AAA
CAA GTT GAA CTT TTA GAT AAA TCT TTT AAT AAA ATG
AAG ACC CCT GAA AAT ATT ATG TTA TTT AGA GGC GAC
GAC CCT GCT TAT TTA GGA ACA GAA TTT CAA AAC ACT
CTT CTT AAT TCA AAT GGT ACA ATT AAT AAA ACG GCT
TTT GAA AAG GCT AAA GCT AAG TTT TTA AAT AAA GAT
AGA CTT GAA TAT GGA TAT ATT AGT ACT TCA TTA ATG
AAT GTT TCT CAA TTT GCA GGA AGA CCA ATT ATT ACA
AAA TTT AAA GTA GCA AAA GGC TCA AAG GCA GGA TAT
ATT GAC CCT ATT AGT GCT TTT CAG GGA CAA CTT GAA
ATG TTG CTT CCT AGA CAT AGT ACT TAT CAT ATA GAC
GAT ATG AGA TTG TCT TCT GAT GGT AAA CAA ATA ATA
ATT ACA GCA ACA ATG ATG GGC ACA GCT ATC AAT CCT
AAA GAA TTC AGA AGG AAA CAA AGA AGA AAA AGA AGA
CAC CAC CAC CAC CAC CAC GTC GAC TCG AGC GGC CGC
ATC GTG ACT GAC TGA 3'

Protein Sequence of C3Basic3 (SEQ ID NO.: 35)

GSSRVDLQACNAYSINQKAYSNTYQEFTNIDQAKAWGNAQYKKYGLSKSE
KEAIVSYTKSASEINGKLRQNKGVINGFPSNLIKQVELLDKSFNKMKTPE
NIMLFRGDDPAYLGTEFQNTLLNSNGTINKTAFEKAKAKFLNKDRLEYGY
ISTSLMNVSQFAGRPIITKFKVAKGSKAGYIDPISAFQGQLEMLLPRHS
TYHIDDMRLSSDGKQIIITATMMGTAINPKEFRRKQRRKRRHHHHHHVDS
SGRIVTD.

Molecular Weight 29441.47 Daltons
260 Amino Acids
39 Strongly Basic(+) Amino Acids (K,R)
23 Strongly Acidic(−) Amino Acids (D,E)
76 Hydrophobic Amino Acids (A,I,L,F,W,V)
80 Polar Amino Acids (N,C,Q,S,T,Y)
9.833 Isolectric Point
17.211 Charge at PH 7.0
Davis, Botstein, Roth Melting Temp C. 78.29

EXAMPLE 15

Sequences for C3APLT

One of the clones that was selected from the subcloning of C3APL into pGEX encoded a protein that was not the expected size but had good biological activity. This clone that had a frameshift mutation leading to a truncation, and this clone was called C3APLT. The clone was resequenced and the chromatograms analyzed to confirm the sequence. To confirm the sequences of C3APLT, the coding sequence from both strands of pGEX-4T/C3APLT were sequenced by double strand sequencing of the full length of the clone (BioS&T, Montreal, Quebec).

The DNA Sequence for C3APLT is as follows: (SEQ ID NO.: 36)

```
GGATCCTCTA GAGTCGACCT GCAGGCATGC AATGCTTATT      60
                      CCATTAATCA AAAGGCTTAT

TCAAATACTT ACCAGGAGTT TACTAATATT GATCAAGCAA     120
                     AAGCTTGGGG TAATGCTCAG

TATAAAAAGT ATGGACTAAG CAAATCAGAA AAAGAAGCTA     180
                     TAGTATCATA TACTAAAAGC

GCTAGTGAAA TAAATGGAAA GCTAAGACAA AATAAGGGAG     240
                     TTATCAATGG ATTTCCTTCA

AATTTAATAA AACAAGTTGA ACTTTTAGAT AAATCTTTTA     300
                     ATAAAATGAA GACCCCTGAA

AATATTATGT TATTTAGAGG CGACGACCCT GCTTATTTAG     360
                     GAACAGAATT TCAAAACACT

CTTCTTAATT CAAATGGTAC AATTAATAAA ACGGCTTTTG     420
                     AAAAGGCTAA AGCTAAGTTT

TTAAATAAAG ATAGACTTGA ATATGGATAT ATTAGTACTT     480
                     CATTAATGAA TGTTTCTCAA

TTTGCAGGAA GACCAATTAT TACAAAATTT AAAGTAGCAA     540
                     AAGGCTCAAA GGCAGGATAT

ATTGACCCTA TTAGTGCTTT TGCAGGACAA CTTGAAATGT     600
                     TGCTTCCTAG ACATAGTACT

TATCATATAG ACGATATGAG ATTGTCTTCT GATGGTAAAC     660
                     AAATAATAAT TACAGCAACA

ATGATGGGCA CAGCTATCAA TCCTAAAGAA TTCGTGATGA     720
                     ATCCCGCAAA CGCGCAAGGC

AGACATACAC CCGGTACCAG ACTCTAGAGC TAGAGAAGGA     780
                     GTTTCACTTC AATCGCTACT

TGACCCGTCG GCGAAGGATC GAGATCGCCC ACGCCCTGTG     840
                     CCTCACGGAG CGCCAGATAA

AGATTTGGTT CCAGAATCGG CGCATGAAGT GGAAGAAGGA     887
                                  GAACTGA
```

The APLT transport peptide sequence by itself is as follows (SEQ ID NO.: 48):
VMNPANAQGRHTPGTRL The Protein Sequence for C3APLT is as follows: (SEQ ID NO.: 37)

```
GSSRVDLQACNAYSINQKAYSNTYQEFTNIDQAKAWGNAQYKKYGLSKSE

KEAIVSYTKSASEINGKLRQNKGVINGFPSNLIKQVELLDKSFNKMKTP

ENIMLFRGDDPAYLGTEFQNTLLNSNGTINKTAFEKAKAKFLNKDRLEY

GYISTSLMNVSQFAGRPIITKFKVAKGSKAGYIDPISAFAGQLEMLLPRH

STYHIDDMRLSSDGKQIIITATMMGTAINPKEFVMNPANAQGRHTPGTRL
```

Molecular Weight 27574.42 Daltons
248 Amino Acids
33 Strongly Basic(+) Amino Acids (K,R)
21 Strongly Acidic(−) Amino Acids (D,E)
76 Hydrophobic Amino Acids (A,I,L,F,W,V)
80 Polar Amino Acids (N,C,Q,S,T,Y)
9.636 Isoelectric Point
12.379 Charge at PH 7.0

EXAMPLE 16

Subcloning and Sequences for C3APLT in pET

C3 has been reported to be stably expressed in *E. coli* by both pGEX-series and pET-series vectors (e.g., Dillon and Feig, 1995 Meth. Enzymol. 256: 174–184. Small GTPases and Their Regulators. Part B. Rho Family. W. E. Balch, C. J. Der, and A. Hall, eds.; Lehmann et al., 1999 supra; Han et al., 2001. J. Mol. Biol. 395: 95–107). The fusion proteins were expressed well in the pGEX vector, for synthesis and testing. However, for large-scale production it is more efficient to synthesize recombinant proteins without an affinity tag that increases the size of the protein produced. Also, it is more economical to synthesize proteins in large scale by affinity chromatography using automated FPLC systems. The polymerase chain reaction was used to transfer recombinant construct C3APLT into the pET T7 polymerase based system *E. coli* expression system (reviewed by Studier et al., 1990. Meth. Enzymol. 185: 60–89. Gene Expression Technology. D. V. Goeddel, ed.). A similar PCR approach is suitable for others in the fusion protein series of C3-based constructs with transport sequences. The pET3a vector DNA was obtained from Dr. Jerry Pelletier, McGill University. PCR primers were obtained from Invitrogen. The upper (5') primer was 5'-GGA TCT GGT TCC GCG <u>TCA TAT GTC</u> TAG AGT CGA CCT G-3' (37 b) (SEQ ID NO.:38). Underlined is the Nde I site that was introduced into the primer to replace the BamHI site in pGEX4T-C3APLT. The lower primer was 5'-CGC <u>GGA TCC ATT</u> AGT TCT CCT TCT TCC ACT TC-3' (32 b) (SEQ ID NO.:39). This primer introduced two changes in the coding strand DNA of pGEX4T-C3APLT, replacing the EcoRI site from pGEX4T-C3APLT with a BamiH I site (underlined) and replacing a TGA stop codon with the strong stop sequence TAAT (the italicized ATTA sequence in the complementary primer). Compared to pGEX4T-C3APLT, the predicted N-terminal sequence of pET3a-C3APLT is Met-Ser rather than Gly-Ser-Ser, a loss of one serine and a substitution of Met for Gly. There were no changes in amino acid sequence at the C-terminus of C3APLT.

The target C3APLT gene was amplified using Pfu polymerase (Invitrogen/Canadian Life Technologies) with buffer, DNA and deoxyribonucleotide concentrations recommended by the manufacturer. The PCR was carried out as follows: 95° C. for 5 minutes, 10 cycles of 94° C. for 2 minutes followed by 56° C. for 2 minutes then extension at 70° C. for 2 minutes, then 30 cycles of 94° C. for 2 minutes followed by 70° C. Completed reactions were stored at 4° C. The QIAEXII kit (Qiagen) was used to purify the agarose gel slice containing DNA band. The purified PCR product DNA and the vector were digested with BamH I and Nde I (both obtained from New England BioLabs) following the instructions of the manufacturer. The digestion products were separated from extraneous DNA by agarose gel electrophoresis and purified with the QIAEXII kit. The insert and vector DNA were incubated together overnight at 16° C. with T4 DNA ligase according to directions provided by the manufacturer (New England BioLabs). Competent *E. coli* (DH5α, obtained from Invitrogen/Canadian Life Technologies) were transformed with the ligation mixture.

DNA was prepared from purified colonies using the Qiagen plasmid midi kit, and the entire insert and junction sequences were verified by double strand sequencing of the full length of the clone (BioS&T, Montreal, Quebec) with forward primer 5' AAA TTA ATA CGA CTC ACT ATA GGG 3' (24 bases) (SEQ ID NO.: 40) and reverse T7 terminator sequencing primer 5' GCT AGT TAT TGC TCAGCG G 3' (19 bases) (SEQ ID NO.: 41). The sequence of the C3APLT cDNA in pET is given in SEQ ID NO.: 42. The amino acid sequence is given in SEQ. ID NO.: 43.

EXAMPLE 17

Modifications of Sequences

Any of sequences given in Examples 1, 2, 8, 9, 10, 11, 12 and 13, 15 and 16 could be modified to retain C3 enzymatic activity and effective transport sequences. For example amino acids encoded from DNA at the 3' end of the sequence that represents the translation of the restriction sites used in cloning may be removed without affecting activity. Some of the amino terminal amino acids may also be removed without affecting activity. The minimal amount of sequence needed for biological activity of the C3 portion of the fusion protein is not known but could be easily determined by known techniques. For example, increasingly more of the 5' end of the cDNA encoding C3 could be removed, and the resulting proteins made and tested for biological activity. Similarly, increasing amounts of the 3' end could be removed and the fragments tested for biological activity. Next, fragments testing the central region could be tested for retention of C3 activity. Therefore, the C3 portion of the protein could be truncated to include just the amino acids needed for activity. Alternatively mutations could be made in the coding regions of C3, and the resulting proteins tested for activity. The transport sequences could be modified to add or remove one or more amino acids or to completely change the transport peptide, but retain the transport characteristics in terms of effective dose compared to C3 in our tissue culture bioassay (Example 4). New transport sequences could be tested for biological activity to improve the efficiency of C3 activity by plating neurons and testing them on inhibitory substrates, as described in Example 4.

As discussed previously, it has been determined in tissue culture studies, that the minimum amount of C3 that can be used to induce growth on inhibitory substrates is 25 ug/ml (Lehmann, et al. (1999) J. Neurosci. 19: 7537–7547; Morii, N and Narumiya, S. (1995) Methods in Enzymology, Vol 256 part B, pg. 196–206. If the cells are not triturated, even this dose is ineffective (FIG. 1). In the context of the present invention it has been determined, for example, that at least 40 $\mu$g of C3/20 g mouse needs to be applied to injured mouse spinal cord or rat optic nerve (McKerracher, Canadian patent application No.: 2,325,842). Calculating doses that would be required to treat an adult human on an equivalent dose per weight scale up used for rat and mice experiments, it would be necessary to apply 120 mg/kg of C3 (i.e. alone) to the injured human spinal cord. This large amount of recombinant C3 protein needed, creates significant problems for manufacturing, due to the large-scale protein purification and cost. It also limits the dose ranging that can be tested because of the large amount of protein needed for minimal effective doses.

Fusion proteins of the present invention are much more effective than C3 (i.e., alone) in promoting neurite outgrowth on myelin substrate. For example, concentrations of C3APLT and C3APS, 10,000 and 1,000 times less than the concentration needed for C3 may be used with comparable (similar) effects without exhibiting toxic effects (e.g., on PC-12 cells). C3-TL and C3-TS are also able to promote neurite growth on myelin substrates at doses significantly less than C3. In vivo results also indicate that lower dose of the fusion proteins may be required to promote regeneration and functional recovery after spinal cord injury in mice. Thus, fusion proteins of the present invention represent a significant improvement and advantage over C3 in both manufacture cost and doses required for treatment.

I claim:

1. A pharmaceutical composition comprising;
   a) a polypeptide consisting of SEQ ID NO: 43 and;
   b) a pharmaceutically acceptable carrier.

2. The pharmaceutical composition of claim 1, wherein the carrier comprises a biological adhesive.

3. The pharmaceutical composition of claim 1, wherein the carrier comprises fibrin.

4. A pharmaceutical composition comprising;
   a) a polypeptide comprising an amino acid sequence of a transport agent covalently linked to an amino acid sequence of an active agent, said amino acid sequence of said active agent consisting of ADP-ribosyl transferase C3 or a fragment thereof retaining ADP-ribosyl transferase activity, said amino acid sequence of said transport agent facilitating uptake of the active agent by a receptor-independent mechanism and being selected from the group consisting of a subdomain of HIV Tat protein, a homeodomain of antennapedia, and a Histidine tag, and
   b) a pharmaceutically acceptable carrier.

5. The pharmaceutical composition of claim 4, wherein the carrier comprises a biological adhesive.

6. The pharmaceutical composition of claim 4, wherein the carrier comprises fibrin.

7. A pharmaceutical composition comprising;
   a) a polypeptide comprising an amino acid sequence of a transport agent covalently linked to an amino acid sequence of an active agent, said amino acid sequence of said active agent consisting of ADP-ribosyl transferase C3 or a fragment thereof retaining ADP-ribosyl transferase activity, said amino acid sequence of said transport agent facilitating uptake of the active agent by a receptor-independent mechanism and being selected from the group consisting of SEQ IDNO:21, SEQ ID NQ:26, SEQ IDNO:31, SEQ ID NO:44, SEQ ID NO:45, SEQ ID NO:46, ftnd SEQ ID NO: 47, and SEQ ID NO: 48 and
   b) a pharmaceutically acceptable carrier.

8. The pharmaceutical composition of claim 7, wherein the carrier comprises a biological adhesive.

9. The pharmaceutical composition of claim 7, wherein the carrier comprises fibrin.

10. A pharmaceutical composition comprising;
    a) a polypeptide comprising an amino acid sequence of a transport agent covalently linked to an amino acid sequence of an active agent, said amino acid sequence of said active agent consisting of ADP-ribosyl transferase C3 or an amino acid sequence having at least 90% sequence identity with the amino acid sequence of SEQ ID NO: 43 and retaining ADP-ribosyl transferase activity, said amino acid sequence of said transport agent facilitating uptake of the active agent by a receptor-independent mechanism and being selected from the group consisting of a subdomain of HIV Tat protein, a homeodomain of antennapedia, and a Histidine tag, and b) a pharmaceutically acceptable carrier.

11. The pharmaceutical composition of claim 10, wherein the carrier comprises a biological adhesive.

12. The pharmaceutical composition of claim 10, wherein the carrier comprises fibrin.

13. A pharmaceutical composition comprising;

a) a polypeptide comprising an amino acid sequence of a transport agent covalently linked to an amino acid sequence of an active agent, said amino acid sequence of said active agent consisting of ADP-ribosyl transferase C3 or an amino acid sequence having at least 90% sequence identity with the amino acid sequence of SEO ID NO: 43 and rctaining ADP-ribosyl transferase activity, said amino acid sequence of said transport agent facilitating uptake of the active agent by a receptor-independent mechanism and being selected from the group consisting of SEQ ID NO:21, SEQ ID NO:26, SEQ ID NO:31, SEQ ID NO:44, SEQ ID NO:45, SEQ IDNO:46, SEQ ID NO: 47, and SEQ ID NO: 48, and b) a pharmaceutically acceptable carrier.

14. The pharmaceutical composition of claim 13, wherein the carrier comprises a biological adhesive.

15. The pharmaceutical composition of claim 13, wherein the carrier comprises fibrin.

16. A method of facilitating axon growth comprising delivering a pharmaceutical composition according to any one of claims 1, 4, 7, 10, or 13 directly at a central nervous system lesion site or a peripheral nervous system lesion site, in an amount effective to facilitate said growth.

17. A method of treating nerve injury comprising delivering a pharmaceutical composition according to any one of claims 1, 4, 7, 10, or 13 directly at a central nervous system lesion site or a peripheral nervous system lesion site, in an amount effective to treat said nerve injury.

18. A substantially purified polypeptide comprising an amino acid sequence of a transport agent covalently linked to an amino acid sequence of an active agent, said amino acid sequence of said active agent consisting of ADP-ribosyl transferase C3 or a fragment thereof retaining ADP-ribosyl transferase activity, said amino acid sequence of said transport agent facilitating uptake of the active agent by a receptor-independent mechanism and being selected from the group consisting of a subdomain of HIV Tat protein, a homeodomain of antennapedia, and a Histidine tag, said polypeptide having ADP-ribosyl transferase activity.

19. The substantially purified polypeptide of claim 18, whercin the amino acid sequence of the transport agent is at the carboxy-terminal end of said polypeptide and the amino acid sequence of the active agent is at the amino terminal end of said polypeptide.

20. A substantially purified polypeptide comprising an amino acid sequence of a transport agent covalently linked to an amino acid sequence of an active agent, said amino acid sequence of said active agent consisting of ADP-ribosyl transferase C3 or a fragment thereof retaining ADP-ribosyl transferase activity, said amino acid sequence of said transport agent facilitating uptake of the active agent by a receptor-independent mechanism and being selected from the group consisting of SEQ ID NO:21, SEQ ID NO:26, SEQ ID NO:31, SEQ ID NO:44, SEQ ID NO:45, SEQ ID NO:46, SEQ ID NO: 47, and SEQ ID NO: 48, said polypeptide having ADP-ribosyl transferase activity.

21. The substantially purified polypeptide of claim 20, wherein the amino acid sequence of the transport agent is at the carboxy-terminal end of said polypeptide and the amino acid sequence of the active agent is at the amino terminal end of said polypeptide.

22. A substantially purified polypeptide comprising an amino acid sequence of a transport agent covalently linked to an amino acid sequence of an active agent, said amino acid sequence of said active agent consisting of ADP-ribosyl transferase C3 or an amino acid sequence having at least 90% sequence identity with the amino acid sequence of SEQ ID NO: 43 and retaining ADP-ribosyl transferase activity, said amino acid sequence of said transport agcnt facilitating uptake of the activc agent by a receptor-independent mechanism and being selected from the group consisting of a subdomain of HIV Tat protein, a homeodomain of antennapedia, and a Histidine tag, said polypeptide having ADP-ribosyl transferase activity.

23. The substantially purified polypeptide of claim 22, wherein the amino acid sequence of the transport agent is at the carboxy-terminal end of said polypeptide and the amino acid sequence of the active agent is at the amino terminal end of said polyp eptide.

24. A substantially purified polypeptide comprising an amino acid sequence of a transport agent covalently linked to an amino acid sequence of an active agent, said amino acid sequence of said active agent consisting of ADP-ribosyl transferase C3 or an amino acid sequence having at least 90% sequence identity with the amino acid sequence of SEQ ID NO: 43 and retaining ADP-ribosyl transferase activity, said amino acid sequence of said transport agent facilitating uptake of the active agent by a receptor-independent mechanism and being selected from the group consisting of SEQ ID NO:21, SEQ ID NO:26, SEQ ID NO:31, SEQ ID NO:44, SEQ ID NO:45, SEQ ID NO:46, SEQ ID NO: 47, and SEQ ID NO: 48, said polypeptide having ADP-ribosyl transferase activity.

25. The substantially purified polypeptide of claim 24, wherein the amino acid sequence of the transport agent is at the carboxy-terminal end of said polypeptide and the amino acid sequence of the active agent is at the amino terminal end of said polypeptide.

* * * * *

SEQUENCE LISTING

<160> NUMBER OF SEQ ID NOS: 53

<210> SEQ ID NO 1
<211> LENGTH: 27
<212> TYPE: DNA
<213> ORGANISM: Artificial Sequence
<220> FEATURE:
<223> OTHER INFORMATION: Oligonucleotide used to remove the stop codon
    from ADP-ribosyl tr ansferase C3 (Clostridium botulinum) cDNA.

<400> SEQUENCE: 1
gaattcttta ggattgatag ctgtgcc                                        27

<210> SEQ ID NO 2
<211> LENGTH: 21
<212> TYPE: DNA
<213> ORGANISM: Artificial Sequence
<220> FEATURE:
<223> OTHER INFORMATION: Oligonucleotide used to remove the stop codon
    from ADP-ribosyl tr ansferase C3 (Clostridium botulinum) cDNA.

<400> SEQUENCE: 2
ggtggcgacc atcctccaaa a                                              21

<210> SEQ ID NO 3
<211> LENGTH: 888
<212> TYPE: DNA
<213> ORGANISM: Artificial Sequence
<220> FEATURE:
<223> OTHER INFORMATION: Sequence of C3APL: includes ADP-ribosyl transferase C3 (Clostridium botulinum) and Antennapedia sequence.
<220> FEATURE:
<221> NAME/KEY: CDS
<222> LOCATION: (1)..(888)
<223> OTHER INFORMATION:

<400> SEQUENCE: 3

| | | | | | | | | | | | | | | | | |
|---|---|---|---|---|---|---|---|---|---|---|---|---|---|---|---|---|
| gga | tcc | tct | aga | gtc | gac | ctg | cag | gca | tgc | aat | gct | tat | tcc | att | aat | 48 |
| Gly | Ser | Ser | Arg | Val | Asp | Leu | Gln | Ala | Cys | Asn | Ala | Tyr | Ser | Ile | Asn | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| caa | aag | gct | tat | tca | aat | act | tac | cag | gag | ttt | act | aat | att | gat | caa | 96 |
| Gln | Lys | Ala | Tyr | Ser | Asn | Thr | Tyr | Gln | Glu | Phe | Thr | Asn | Ile | Asp | Gln | |
| | | | 20 | | | | | 25 | | | | | 30 | | | |

| | | | | | | | | | | | | | | | | |
|---|---|---|---|---|---|---|---|---|---|---|---|---|---|---|---|---|
| gca | aaa | gct | tgg | ggt | aat | gct | cag | tat | aaa | aag | tat | gga | cta | agc | aaa | 144 |
| Ala | Lys | Ala | Trp | Gly | Asn | Ala | Gln | Tyr | Lys | Lys | Tyr | Gly | Leu | Ser | Lys | |
| | | 35 | | | | | 40 | | | | | 45 | | | | |

| | | | | | | | | | | | | | | | | |
|---|---|---|---|---|---|---|---|---|---|---|---|---|---|---|---|---|
| tca | gaa | aaa | gaa | gct | ata | gta | tca | tat | act | aaa | agc | gct | agt | gaa | ata | 192 |
| Ser | Glu | Lys | Glu | Ala | Ile | Val | Ser | Tyr | Thr | Lys | Ser | Ala | Ser | Glu | Ile | |
| 50 | | | | | 55 | | | | | 60 | | | | | | |

| | | | | | | | | | | | | | | | | |
|---|---|---|---|---|---|---|---|---|---|---|---|---|---|---|---|---|
| aat | gga | aag | cta | aga | caa | aat | aag | gga | gtt | atc | aat | gga | ttt | cct | tca | 240 |
| Asn | Gly | Lys | Leu | Arg | Gln | Asn | Lys | Gly | Val | Ile | Asn | Gly | Phe | Pro | Ser | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| aat | tta | ata | aaa | caa | gtt | gaa | ctt | tta | gat | aaa | tct | ttt | aat | aaa | atg | 288 |
| Asn | Leu | Ile | Lys | Gln | Val | Glu | Leu | Leu | Asp | Lys | Ser | Phe | Asn | Lys | Met | |
| | | | | 85 | | | | | 90 | | | | | 95 | | |

| | | | | | | | | | | | | | | | | |
|---|---|---|---|---|---|---|---|---|---|---|---|---|---|---|---|---|
| aag | acc | cct | gaa | aat | att | atg | tta | ttt | aga | ggc | gac | gac | cct | gct | tat | 336 |
| Lys | Thr | Pro | Glu | Asn | Ile | Met | Leu | Phe | Arg | Gly | Asp | Asp | Pro | Ala | Tyr | |
| | | | 100 | | | | | 105 | | | | | 110 | | | |

| | | | | | | | | | | | | | | | | |
|---|---|---|---|---|---|---|---|---|---|---|---|---|---|---|---|---|
| tta | gga | aca | gaa | ttt | caa | aac | act | ctt | ctt | aat | tca | aat | ggt | aca | att | 384 |
| Leu | Gly | Thr | Glu | Phe | Gln | Asn | Thr | Leu | Leu | Asn | Ser | Asn | Gly | Thr | Ile | |
| | | 115 | | | | | 120 | | | | | 125 | | | | |

| | | | | | | | | | | | | | | | | |
|---|---|---|---|---|---|---|---|---|---|---|---|---|---|---|---|---|
| aat | aaa | acg | gct | ttt | gaa | aag | gct | aaa | gct | aag | ttt | tta | aat | aaa | gat | 432 |
| Asn | Lys | Thr | Ala | Phe | Glu | Lys | Ala | Lys | Ala | Lys | Phe | Leu | Asn | Lys | Asp | |
| 130 | | | | | 135 | | | | | 140 | | | | | | |

| | | | | | | | | | | | | | | | | |
|---|---|---|---|---|---|---|---|---|---|---|---|---|---|---|---|---|
| aga | ctt | gaa | tat | gga | tat | att | agt | act | tca | tta | atg | aat | gtc | tct | caa | 480 |
| Arg | Leu | Glu | Tyr | Gly | Tyr | Ile | Ser | Thr | Ser | Leu | Met | Asn | Val | Ser | Gln | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ttt | gca | gga | aga | cca | att | att | aca | caa | ttt | aaa | gta | gca | aaa | ggc | tca | 528 |
| Phe | Ala | Gly | Arg | Pro | Ile | Ile | Thr | Gln | Phe | Lys | Val | Ala | Lys | Gly | Ser | |
| | | | | 165 | | | | | 170 | | | | | 175 | | |

| | | | | | | | | | | | | | | | | |
|---|---|---|---|---|---|---|---|---|---|---|---|---|---|---|---|---|
| aag | gca | gga | tat | att | gac | cct | att | agt | gct | ttt | cag | gga | caa | ctt | gaa | 576 |
| Lys | Ala | Gly | Tyr | Ile | Asp | Pro | Ile | Ser | Ala | Phe | Gln | Gly | Gln | Leu | Glu | |
| | | | 180 | | | | | 185 | | | | | 190 | | | |

| | | | | | | | | | | | | | | | | |
|---|---|---|---|---|---|---|---|---|---|---|---|---|---|---|---|---|
| atg | ttg | ctt | cct | aga | cat | agt | act | tat | cat | ata | gac | gat | atg | aga | ttg | 624 |
| Met | Leu | Leu | Pro | Arg | His | Ser | Thr | Tyr | His | Ile | Asp | Asp | Met | Arg | Leu | |
| | | 195 | | | | | 200 | | | | | 205 | | | | |

| | | | | | | | | | | | | | | | | |
|---|---|---|---|---|---|---|---|---|---|---|---|---|---|---|---|---|
| tct | tct | gat | ggt | aaa | caa | ata | ata | att | aca | gca | aca | atg | atg | ggc | aca | 672 |
| Ser | Ser | Asp | Gly | Lys | Gln | Ile | Ile | Ile | Thr | Ala | Thr | Met | Met | Gly | Thr | |
| | | | 210 | | | | | 215 | | | | | 220 | | | |

| | | | | | | | | | | | | | | | | |
|---|---|---|---|---|---|---|---|---|---|---|---|---|---|---|---|---|
| gct | atc | aat | cct | aaa | gaa | ttc | gtg | atg | gaa | tcc | cgc | aaa | cgc | gca | agg | 720 |
| Ala | Ile | Asn | Pro | Lys | Glu | Phe | Val | Met | Glu | Ser | Arg | Lys | Arg | Ala | Arg | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| cag | aca | tac | acc | cgg | tac | cag | act | cta | gag | cta | gag | aag | gag | ttt | cac | 768 |
| Gln | Thr | Tyr | Thr | Arg | Tyr | Gln | Thr | Leu | Glu | Leu | Glu | Lys | Glu | Phe | His | |
| | | | | 245 | | | | | 250 | | | | | 255 | | |

```
ttc aat cgc tac ttg acc cgt cgg cga agg atc gag atc gcc cac gcc    816
Phe Asn Arg Tyr Leu Thr Arg Arg Arg Arg Ile Glu Ile Ala His Ala
        260                 265                 270 ctg tgc ctc acg gag cgc cag ata aag att tgg ttc cag aat cgg cgc    864
Leu Cys Leu Thr Glu Arg Gln Ile Lys Ile Trp Phe Gln Asn Arg Arg
        275                 280                 285 atg aag tgg aag aag gag aac tga                                    888
Met Lys Trp Lys Lys Glu Asn
        290                 295
```

<210> SEQ ID NO 4
<211> LENGTH: 295
<212> TYPE: PRT
<213> ORGANISM: Artificial Sequence
<220> FEATURE:
<223> OTHER INFORMATION: Sequence of C3APL: includes ADP-ribosyl
    transferase C3 (Clostridium botulinum) and Antennapedia
    sequence.

<400> SEQUENCE: 4

```
Gly Ser Ser Arg Val Asp Leu Gln Ala Cys Asn Ala Tyr Ser Ile Asn
1               5                   10                  15

Gln Lys Ala Tyr Ser Asn Thr Tyr Gln Glu Phe Thr Asn Ile Asp Gln
            20                  25                  30

Ala Lys Ala Trp Gly Asn Ala Gln Tyr Lys Lys Tyr Gly Leu Ser Lys
        35                  40                  45

Ser Glu Lys Glu Ala Ile Val Ser Tyr Thr Lys Ser Ala Ser Glu Ile
    50                  55                  60

Asn Gly Lys Leu Arg Gln Asn Lys Gly Val Ile Asn Gly Phe Pro Ser
65                  70                  75                  80

Asn Leu Ile Lys Gln Val Glu Leu Leu Asp Lys Ser Phe Asn Lys Met
                85                  90                  95

Lys Thr Pro Glu Asn Ile Met Leu Phe Arg Gly Asp Asp Pro Ala Tyr
            100                 105                 110

Leu Gly Thr Glu Phe Gln Asn Thr Leu Leu Asn Ser Asn Gly Thr Ile
        115                 120                 125

Asn Lys Thr Ala Phe Glu Lys Ala Lys Ala Lys Phe Leu Asn Lys Asp
    130                 135                 140

Arg Leu Glu Tyr Gly Tyr Ile Ser Thr Ser Leu Met Asn Val Ser Gln
145                 150                 155                 160

Phe Ala Gly Arg Pro Ile Ile Thr Gln Phe Lys Val Ala Lys Gly Ser
                165                 170                 175

Lys Ala Gly Tyr Ile Asp Pro Ile Ser Ala Phe Gln Gly Gln Leu Glu
            180                 185                 190

Met Leu Leu Pro Arg His Ser Thr Tyr His Ile Asp Asp Met Arg Leu
        195                 200                 205

Ser Ser Asp Gly Lys Gln Ile Ile Ile Thr Ala Thr Met Met Gly Thr
    210                 215                 220

Ala Ile Asn Pro Lys Glu Phe Val Met Glu Ser Arg Lys Arg Ala Arg
225                 230                 235                 240

Gln Thr Tyr Thr Arg Tyr Gln Thr Leu Glu Leu Glu Lys Glu Phe His
                245                 250                 255

Phe Asn Arg Tyr Leu Thr Arg Arg Arg Ile Glu Ile Ala His Ala
            260                 265                 270
```

```
Leu Cys Leu Thr Glu Arg Gln Ile Lys Ile Trp Phe Gln Asn Arg Arg
            275                 280                 285

Met Lys Trp Lys Lys Glu Asn
    290                 295

<210> SEQ ID NO 5
<211> LENGTH: 774
<212> TYPE: DNA
<213> ORGANISM: Artificial Sequence
<220> FEATURE:
<223> OTHER INFORMATION: Sequence of C3APS: Includes  ADP-ribosyl
      transferase C3 (Clostridium botulinum) and Antennapedia
      sequence.
<220> FEATURE:
<221> NAME/KEY: CDS
<222> LOCATION: (1)..(774)
<223> OTHER INFORMATION:

<400> SEQUENCE: 5 gga tcc tct aga gtc gac ctg cag gca tgc aat gct tat tcc att aat      48
Gly Ser Ser Arg Val Asp Leu Gln Ala Cys Asn Ala Tyr Ser Ile Asn
1               5                   10                  15 caa aag gct tat tca aat act tac cag gag ttt act aat att gat caa     96
Gln Lys Ala Tyr Ser Asn Thr Tyr Gln Glu Phe Thr Asn Ile Asp Gln
                20                  25                  30 gca aaa gct tgg ggt aat gct cag tat aaa aag tat gga cta agc aaa    144
Ala Lys Ala Trp Gly Asn Ala Gln Tyr Lys Lys Tyr Gly Leu Ser Lys
            35                  40                  45 tca gaa aaa gaa gct ata gta tca tat act aaa agc gct agt gaa ata    192
Ser Glu Lys Glu Ala Ile Val Ser Tyr Thr Lys Ser Ala Ser Glu Ile
        50                  55                  60 aat gga aag cta aga caa aat aag gga gtt atc aat gga ttt cct tca    240
Asn Gly Lys Leu Arg Gln Asn Lys Gly Val Ile Asn Gly Phe Pro Ser
65                  70                  75                  80 aat tta ata aaa caa gtt gaa ctt tta gat aaa tct ttt aat aaa atg    288
Asn Leu Ile Lys Gln Val Glu Leu Leu Asp Lys Ser Phe Asn Lys Met
                85                  90                  95 aag acc cct gaa aat att atg tta ttt aga ggc gac gac cct gct tat    336
Lys Thr Pro Glu Asn Ile Met Leu Phe Arg Gly Asp Asp Pro Ala Tyr
                100                 105                 110 tta gga aca gaa ttt caa aac act ctt ctt aat tca aat ggt aca att    384
Leu Gly Thr Glu Phe Gln Asn Thr Leu Leu Asn Ser Asn Gly Thr Ile
            115                 120                 125 aat aaa acg gct ttt gaa aag gct aaa gct aag ttt tta aat aaa gat    432
Asn Lys Thr Ala Phe Glu Lys Ala Lys Ala Lys Phe Leu Asn Lys Asp
        130                 135                 140 aga ctt gaa tat gga tat att agt act tca tta atg aat gtc tct caa    480
Arg Leu Glu Tyr Gly Tyr Ile Ser Thr Ser Leu Met Asn Val Ser Gln
145                 150                 155                 160 ttt gca gga aga cca att att aca caa ttt aaa gta gca aaa ggc tca    528
Phe Ala Gly Arg Pro Ile Ile Thr Gln Phe Lys Val Ala Lys Gly Ser
                165                 170                 175 aag gca gga tat att gac cct att agt gct ttt cag gga caa ctt gaa    576
Lys Ala Gly Tyr Ile Asp Pro Ile Ser Ala Phe Gln Gly Gln Leu Glu
            180                 185                 190 atg ttg ctt cct aga cat agt act tat cat ata gac gat atg aga ttg    624
Met Leu Leu Pro Arg His Ser Thr Tyr His Ile Asp Asp Met Arg Leu
        195                 200                 205 tct tct gat ggt aaa caa ata ata att aca gca aca atg atg ggc aca    672
Ser Ser Asp Gly Lys Gln Ile Ile Ile Thr Ala Thr Met Met Gly Thr
    210                 215                 220
```

-continued

```
gct atc aat cct aaa gaa ttc cgc cag atc aag att tgg ttc cag aat        720
Ala Ile Asn Pro Lys Glu Phe Arg Gln Ile Lys Ile Trp Phe Gln Asn
225                 230                 235                 240 cgt cgc atg aag tgg aag aag gtc gac tcg agc ggc cgc atc gtg act        768
Arg Arg Met Lys Trp Lys Lys Val Asp Ser Ser Gly Arg Ile Val Thr
                245                 250                 255 gac tga                                                                 774
Asp
```

<210> SEQ ID NO 6
<211> LENGTH: 257
<212> TYPE: PRT
<213> ORGANISM: Artificial Sequence
<220> FEATURE:
<223> OTHER INFORMATION: Sequence of C3APS: Includes ADP-ribosyl
      transferase C3 (Clostridium botulinum) and Antennapedia
      sequence.

<400> SEQUENCE: 6

```
Gly Ser Ser Arg Val Asp Leu Gln Ala Cys Asn Ala Tyr Ser Ile Asn
1               5                   10                  15

Gln Lys Ala Tyr Ser Asn Thr Tyr Gln Glu Phe Thr Asn Ile Asp Gln
            20                  25                  30

Ala Lys Ala Trp Gly Asn Ala Gln Tyr Lys Lys Tyr Gly Leu Ser Lys
        35                  40                  45

Ser Glu Lys Glu Ala Ile Val Ser Tyr Thr Lys Ser Ala Ser Glu Ile
    50                  55                  60

Asn Gly Lys Leu Arg Gln Asn Lys Gly Val Ile Asn Gly Phe Pro Ser
65                  70                  75                  80

Asn Leu Ile Lys Gln Val Glu Leu Leu Asp Lys Ser Phe Asn Lys Met
                85                  90                  95

Lys Thr Pro Glu Asn Ile Met Leu Phe Arg Gly Asp Asp Pro Ala Tyr
            100                 105                 110

Leu Gly Thr Glu Phe Gln Asn Thr Leu Leu Asn Ser Asn Gly Thr Ile
        115                 120                 125

Asn Lys Thr Ala Phe Glu Lys Ala Lys Ala Lys Phe Leu Asn Lys Asp
    130                 135                 140

Arg Leu Glu Tyr Gly Tyr Ile Ser Thr Ser Leu Met Asn Val Ser Gln
145                 150                 155                 160

Phe Ala Gly Arg Pro Ile Ile Thr Gln Phe Lys Val Ala Lys Gly Ser
                165                 170                 175

Lys Ala Gly Tyr Ile Asp Pro Ile Ser Ala Phe Gln Gly Gln Leu Glu
            180                 185                 190

Met Leu Leu Pro Arg His Ser Thr Tyr His Ile Asp Asp Met Arg Leu
        195                 200                 205

Ser Ser Asp Gly Lys Gln Ile Ile Thr Ala Thr Met Met Gly Thr
    210                 215                 220

Ala Ile Asn Pro Lys Glu Phe Arg Gln Ile Lys Ile Trp Phe Gln Asn
225                 230                 235                 240

Arg Arg Met Lys Trp Lys Lys Val Asp Ser Ser Gly Arg Ile Val Thr
                245                 250                 255

Asp
```

<210> SEQ ID NO 7
<211> LENGTH: 24
<212> TYPE: DNA
<213> ORGANISM: Artificial Sequence -continued

```
<220> FEATURE:
<223> OTHER INFORMATION: Oligonucleotide used in the amplification of
      Antennapedia sequence

<400> SEQUENCE: 7
gaatcccgca aacgcgcaag gcag                                            24

<210> SEQ ID NO 8
<211> LENGTH: 27
<212> TYPE: DNA
<213> ORGANISM: Artificial Sequence
<220> FEATURE:
<223> OTHER INFORMATION: Oligonucleotide used in the amplification of
      Antennapedia sequence

<400> SEQUENCE: 8
tcagttctcc ttcttccact tcatgcg                                         27

<210> SEQ ID NO 9
<211> LENGTH: 54
<212> TYPE: DNA
<213> ORGANISM: Artificial Sequence
<220> FEATURE:
<223> OTHER INFORMATION: Oligonucleotide used in the cloning of
      sequences from Antennapedia

<400> SEQUENCE: 9
aattccgcca gatcaagatt tggttccaga atcgtcgcat gaagtggaag aagg           54

<210> SEQ ID NO 10
<211> LENGTH: 54
<212> TYPE: DNA
<213> ORGANISM: Artificial Sequence
<220> FEATURE:
<223> OTHER INFORMATION: Oligonucleotide used in the cloning of
      sequences from Antennapedia

<400> SEQUENCE: 10
ggcggtctag ttctaaacca agctcttagc agcgtagttc accttcttcc agct           54

<210> SEQ ID NO 11
<211> LENGTH: 26
<212> TYPE: DNA
<213> ORGANISM: Artificial Sequence
<220> FEATURE:
<223> OTHER INFORMATION: Oligonucleotide used inthe amplification of
      a sequence corresponding to amino acid 27-72 of HIV-1 Tat

<400> SEQUENCE: 11
gaatccaagc atccaggaag tcagcc                                          26

<210> SEQ ID NO 12
<211> LENGTH: 21
<212> TYPE: DNA
<213> ORGANISM: Artificial Sequence
<220> FEATURE:
<223> OTHER INFORMATION: Oligonucleotide used inthe amplification of
      a sequence corresponding to amino acid 27-72 of HIV-1 Tat

<400> SEQUENCE: 12
accagccacc accttctgat a                                               21

<210> SEQ ID NO 13
<211> LENGTH: 876
<212> TYPE: DNA
<213> ORGANISM: Artificial Sequence
```

<220> FEATURE:
<223> OTHER INFORMATION: Sequence of C3-TL: Includes ADP-ribosyl
      transferase C3 (Clostridium botulinum) and HIV-1 Tat sequence.
<220> FEATURE:
<221> NAME/KEY: CDS
<222> LOCATION: (1)..(876)
<223> OTHER INFORMATION:

<400> SEQUENCE: 13

```
gga tcc tct aga gtc gac ctg cag gca tgc aat gct tat tcc att aat        48
Gly Ser Ser Arg Val Asp Leu Gln Ala Cys Asn Ala Tyr Ser Ile Asn
1               5                   10                  15 caa aag gct tat tca aat act tac cag gag ttt act aat att gat caa        96
Gln Lys Ala Tyr Ser Asn Thr Tyr Gln Glu Phe Thr Asn Ile Asp Gln
            20                  25                  30 gca aaa gct tgg ggt aat gct cag tat aaa aag tat gga cta agc aaa       144
Ala Lys Ala Trp Gly Asn Ala Gln Tyr Lys Lys Tyr Gly Leu Ser Lys
        35                  40                  45 tca gaa aaa gaa gct ata gta tca tat act aaa agc gct agt gaa ata       192
Ser Glu Lys Glu Ala Ile Val Ser Tyr Thr Lys Ser Ala Ser Glu Ile
50                  55                  60 aat gga aag cta aga caa aat aag gga gtt atc aat gga ttt cct tca       240
Asn Gly Lys Leu Arg Gln Asn Lys Gly Val Ile Asn Gly Phe Pro Ser
65                  70                  75                  80 aat tta ata aaa caa gtt gaa ctt tta gat aaa tct ttt aat aaa atg       288
Asn Leu Ile Lys Gln Val Glu Leu Leu Asp Lys Ser Phe Asn Lys Met
                85                  90                  95 aag acc cct gaa aat att atg tta ttt aga ggc gac gac cct gct tat       336
Lys Thr Pro Glu Asn Ile Met Leu Phe Arg Gly Asp Asp Pro Ala Tyr
            100                 105                 110 tta gga aca gaa ttt caa aac act ctt ctt aat tca aat ggt aca att       384
Leu Gly Thr Glu Phe Gln Asn Thr Leu Leu Asn Ser Asn Gly Thr Ile
        115                 120                 125 aat aaa acg gct ttt gaa aag gct aaa gct aag ttt tta aat aaa gat       432
Asn Lys Thr Ala Phe Glu Lys Ala Lys Ala Lys Phe Leu Asn Lys Asp
130                 135                 140 aga ctt gaa tat gga tat att agt act tca tta atg aat gtc tct caa       480
Arg Leu Glu Tyr Gly Tyr Ile Ser Thr Ser Leu Met Asn Val Ser Gln
145                 150                 155                 160 ttt gca gga aga cca att att aca caa ttt aaa gta gca aaa ggc tca       528
Phe Ala Gly Arg Pro Ile Ile Thr Gln Phe Lys Val Ala Lys Gly Ser
                165                 170                 175 aag gca gga tat att gac cct att agt gct ttt cag gga caa ctt gaa       576
Lys Ala Gly Tyr Ile Asp Pro Ile Ser Ala Phe Gln Gly Gln Leu Glu
            180                 185                 190 atg ttg ctt cct aga cat agt act tat cat ata gac gat atg aga ttg       624
Met Leu Leu Pro Arg His Ser Thr Tyr His Ile Asp Asp Met Arg Leu
        195                 200                 205 tct tct gat ggt aaa caa ata ata att aca gca aca atg atg ggc aca       672
Ser Ser Asp Gly Lys Gln Ile Ile Ile Thr Ala Thr Met Met Gly Thr
210                 215                 220 gct atc aat cct aaa gaa ttc aag cat cca gga agt cag cct aaa act       720
Ala Ile Asn Pro Lys Glu Phe Lys His Pro Gly Ser Gln Pro Lys Thr
225                 230                 235                 240 gct tgt acc aat tgc tat tgt aaa aag tgt tgc ttt cat tgc caa gtt       768
Ala Cys Thr Asn Cys Tyr Cys Lys Lys Cys Cys Phe His Cys Gln Val
                245                 250                 255 tgt ttc ata aca aaa gcc tta ggc atc tcc tat ggc agg aag cgg aga       816
Cys Phe Ile Thr Lys Ala Leu Gly Ile Ser Tyr Gly Arg Lys Arg Arg
            260                 265                 270
```

```
cag cga cga aga gct cat cag aac agt cag act cat caa gct tct cta      864
Gln Arg Arg Arg Ala His Gln Asn Ser Gln Thr His Gln Ala Ser Leu
        275                 280                 285 tca aag cag taa                                                      876
Ser Lys Gln
    290
```

<210> SEQ ID NO 14
<211> LENGTH: 291
<212> TYPE: PRT
<213> ORGANISM: Artificial Sequence
<220> FEATURE:
<223> OTHER INFORMATION: Sequence of C3-TL: Includes ADP-ribosyl
      transferase C3 (Clostridium botulinum) and HIV-1 Tat sequence.

<400> SEQUENCE: 14

```
Gly Ser Ser Arg Val Asp Leu Gln Ala Cys Asn Ala Tyr Ser Ile Asn
1               5                   10                  15

Gln Lys Ala Tyr Ser Asn Thr Tyr Gln Glu Phe Thr Asn Ile Asp Gln
            20                  25                  30

Ala Lys Ala Trp Gly Asn Ala Gln Tyr Lys Lys Tyr Gly Leu Ser Lys
        35                  40                  45

Ser Glu Lys Glu Ala Ile Val Ser Tyr Thr Lys Ser Ala Ser Glu Ile
    50                  55                  60

Asn Gly Lys Leu Arg Gln Asn Lys Gly Val Ile Asn Gly Phe Pro Ser
65                  70                  75                  80

Asn Leu Ile Lys Gln Val Glu Leu Leu Asp Lys Ser Phe Asn Lys Met
                85                  90                  95

Lys Thr Pro Glu Asn Ile Met Leu Phe Arg Gly Asp Asp Pro Ala Tyr
            100                 105                 110

Leu Gly Thr Glu Phe Gln Asn Thr Leu Leu Asn Ser Asn Gly Thr Ile
        115                 120                 125

Asn Lys Thr Ala Phe Glu Lys Ala Lys Ala Lys Phe Leu Asn Lys Asp
130                 135                 140

Arg Leu Glu Tyr Gly Tyr Ile Ser Thr Ser Leu Met Asn Val Ser Gln
145                 150                 155                 160

Phe Ala Gly Arg Pro Ile Ile Thr Gln Phe Lys Val Ala Lys Gly Ser
                165                 170                 175

Lys Ala Gly Tyr Ile Asp Pro Ile Ser Ala Phe Gln Gly Gln Leu Glu
            180                 185                 190

Met Leu Leu Pro Arg His Ser Thr Tyr His Ile Asp Asp Met Arg Leu
        195                 200                 205

Ser Ser Asp Gly Lys Gln Ile Ile Ile Thr Ala Thr Met Met Gly Thr
    210                 215                 220

Ala Ile Asn Pro Lys Glu Phe Lys His Pro Gly Ser Gln Pro Lys Thr
225                 230                 235                 240

Ala Cys Thr Asn Cys Tyr Cys Lys Lys Cys Cys Phe His Cys Gln Val
                245                 250                 255

Cys Phe Ile Thr Lys Ala Leu Gly Ile Ser Tyr Gly Arg Lys Arg Arg
            260                 265                 270

Gln Arg Arg Arg Ala His Gln Asn Ser Gln Thr His Gln Ala Ser Leu
        275                 280                 285

Ser Lys Gln
    290
```

-continued

```
<210> SEQ ID NO 15
<211> LENGTH: 39
<212> TYPE: DNA
<213> ORGANISM: Artificial Sequence
<220> FEATURE:
<223> OTHER INFORMATION: Oligonucleotide used in the cloning of
      sequences from HIV-1 Tat

<400> SEQUENCE: 15
aattctatgg tcgtaaaaaa cgtcgtcaac gtcgtcgtg                              39

<210> SEQ ID NO 16
<211> LENGTH: 39
<212> TYPE: DNA
<213> ORGANISM: Artificial Sequence
<220> FEATURE:
<223> OTHER INFORMATION: Oligonucleotide used in the cloning of
      sequences from HIV-1 Tat

<400> SEQUENCE: 16
gataccagca tttttttgcag cagttgcagc agcacagct                             39

<210> SEQ ID NO 17
<211> LENGTH: 756
<212> TYPE: DNA
<213> ORGANISM: Artificial Sequence
<220> FEATURE:
<223> OTHER INFORMATION: Sequence of C3-TS: Includes ADP-ribosyl
      transferase C3 (Clostridium botulinum) and HIV-1 Tat sequence.
<220> FEATURE:
<221> NAME/KEY: CDS
<222> LOCATION: (1)..(756)
<223> OTHER INFORMATION:

<400> SEQUENCE: 17 gga tcc tct aga gtc gac ctg cag gca tgc aat gct tat tcc att aat        48
Gly Ser Ser Arg Val Asp Leu Gln Ala Cys Asn Ala Tyr Ser Ile Asn
1               5                   10                  15 caa aag gct tat tca aat act tac cag gag ttt act aat att gat caa        96
Gln Lys Ala Tyr Ser Asn Thr Tyr Gln Glu Phe Thr Asn Ile Asp Gln
            20                  25                  30 gca aaa gct tgg ggt aat gct cag tat aaa aag tat gga cta agc aaa       144
Ala Lys Ala Trp Gly Asn Ala Gln Tyr Lys Lys Tyr Gly Leu Ser Lys
        35                  40                  45 tca gaa aaa gaa gct ata gta tca tat act aaa agc gct agt gaa ata       192
Ser Glu Lys Glu Ala Ile Val Ser Tyr Thr Lys Ser Ala Ser Glu Ile
    50                  55                  60 aat gga aag cta aga caa aat aag gga gtt atc aat gga ttt cct tca       240
Asn Gly Lys Leu Arg Gln Asn Lys Gly Val Ile Asn Gly Phe Pro Ser
65                  70                  75                  80 aat tta ata aaa caa gtt gaa ctt tta gat aaa tct ttt aat aaa atg       288
Asn Leu Ile Lys Gln Val Glu Leu Leu Asp Lys Ser Phe Asn Lys Met
                85                  90                  95 aag acc cct gaa aat att atg tta ttt aga ggc gac gac cct gct tat       336
Lys Thr Pro Glu Asn Ile Met Leu Phe Arg Gly Asp Asp Pro Ala Tyr
            100                 105                 110 tta gga aca gaa ttt caa aac act ctt ctt aat tca aat ggt aca att       384
Leu Gly Thr Glu Phe Gln Asn Thr Leu Leu Asn Ser Asn Gly Thr Ile
        115                 120                 125 aat aaa acg gct ttt gaa aag gct aaa gct aag ttt tta aat aaa gat       432
Asn Lys Thr Ala Phe Glu Lys Ala Lys Ala Lys Phe Leu Asn Lys Asp
    130                 135                 140 aga ctt gaa tat gga tat att agt act tca tta atg aat gtc tct caa       480
Arg Leu Glu Tyr Gly Tyr Ile Ser Thr Ser Leu Met Asn Val Ser Gln
145                 150                 155                 160
```

```
ttt gca gga aga cca att att aca caa ttt aaa gta gca aaa ggc tca       528
Phe Ala Gly Arg Pro Ile Ile Thr Gln Phe Lys Val Ala Lys Gly Ser
                165                 170                 175 aag gca gga tat att gac cct att agt gct ttt cag gga caa ctt gaa       576
Lys Ala Gly Tyr Ile Asp Pro Ile Ser Ala Phe Gln Gly Gln Leu Glu
                180                 185                 190 atg ttg ctt cct aga cat agt act tat cat ata gac gat atg aga ttg       624
Met Leu Leu Pro Arg His Ser Thr Tyr His Ile Asp Asp Met Arg Leu
                195                 200                 205 tct tct gat ggt aaa caa ata ata att aca gca aca atg atg ggc aca       672
Ser Ser Asp Gly Lys Gln Ile Ile Ile Thr Ala Thr Met Met Gly Thr
        210                 215                 220 gct atc aat cct aaa gaa ttc tat ggt gct aaa aaa cgt cgt caa cgt       720
Ala Ile Asn Pro Lys Glu Phe Tyr Gly Ala Lys Lys Arg Arg Gln Arg
225                 230                 235                 240 cgt cgt gtc gac tcg agc ggc ccg cat cgt gac tga                       756
Arg Arg Val Asp Ser Ser Gly Pro His Arg Asp
                245                 250
```

<210> SEQ ID NO 18
<211> LENGTH: 251
<212> TYPE: PRT
<213> ORGANISM: Artificial Sequence
<220> FEATURE:
<223> OTHER INFORMATION: Sequence of C3-TS: Includes  ADP-ribosyl
      transferase C3 (Clostridium botulinum) and HIV-1 Tat sequence.

<400> SEQUENCE: 18

```
Gly Ser Ser Arg Val Asp Leu Gln Ala Cys Asn Ala Tyr Ser Ile Asn
1               5                   10                  15

Gln Lys Ala Tyr Ser Asn Thr Tyr Gln Glu Phe Thr Asn Ile Asp Gln
            20                  25                  30

Ala Lys Ala Trp Gly Asn Ala Gln Tyr Lys Lys Tyr Gly Leu Ser Lys
        35                  40                  45

Ser Glu Lys Glu Ala Ile Val Ser Tyr Thr Lys Ser Ala Ser Glu Ile
    50                  55                  60

Asn Gly Lys Leu Arg Gln Asn Lys Gly Val Ile Asn Gly Phe Pro Ser
65                  70                  75                  80

Asn Leu Ile Lys Gln Val Glu Leu Leu Asp Lys Ser Phe Asn Lys Met
                85                  90                  95

Lys Thr Pro Glu Asn Ile Met Leu Phe Arg Gly Asp Asp Pro Ala Tyr
            100                 105                 110

Leu Gly Thr Glu Phe Gln Asn Thr Leu Leu Asn Ser Asn Gly Thr Ile
        115                 120                 125

Asn Lys Thr Ala Phe Glu Lys Ala Lys Ala Lys Phe Leu Asn Lys Asp
    130                 135                 140

Arg Leu Glu Tyr Gly Tyr Ile Ser Thr Ser Leu Met Asn Val Ser Gln
145                 150                 155                 160

Phe Ala Gly Arg Pro Ile Ile Thr Gln Phe Lys Val Ala Lys Gly Ser
                165                 170                 175

Lys Ala Gly Tyr Ile Asp Pro Ile Ser Ala Phe Gln Gly Gln Leu Glu
            180                 185                 190

Met Leu Leu Pro Arg His Ser Thr Tyr His Ile Asp Asp Met Arg Leu
        195                 200                 205

Ser Ser Asp Gly Lys Gln Ile Ile Ile Thr Ala Thr Met Met Gly Thr
    210                 215                 220
```

```
Ala Ile Asn Pro Lys Glu Phe Tyr Gly Ala Lys Lys Arg Arg Gln Arg
225                 230                 235                 240

Arg Arg Val Asp Ser Ser Gly Pro His Arg Asp
            245                 250

<210> SEQ ID NO 19
<211> LENGTH: 1413
<212> TYPE: DNA
<213> ORGANISM: Artificial Sequence
<220> FEATURE:
<223> OTHER INFORMATION: Includes GST sequences, ADP-ribosyl
      transferase C3 (C. botulinum) sequence and a random basic
      amino acid sequence.
<220> FEATURE:
<221> NAME/KEY: CDS
<222> LOCATION: (1)..(1413)
<223> OTHER INFORMATION:

<400> SEQUENCE: 19 atg tcc cct ata cta ggt tat tgg aaa att aag ggc ctt gtg caa ccc      48
Met Ser Pro Ile Leu Gly Tyr Trp Lys Ile Lys Gly Leu Val Gln Pro
1               5                   10                  15 act cga ctt ctt ttg gaa tat ctt gaa gaa aaa tat gaa gag cat ttg      96
Thr Arg Leu Leu Leu Glu Tyr Leu Glu Glu Lys Tyr Glu Glu His Leu
            20                  25                  30 tat gag cgc gat gaa ggt gat aaa tgg cga aac aaa aag ttt gaa ttg     144
Tyr Glu Arg Asp Glu Gly Asp Lys Trp Arg Asn Lys Lys Phe Glu Leu
        35                  40                  45 ggt ttg gag ttt ccc aat ctt cct tat tat att gat ggt gat gtt aaa     192
Gly Leu Glu Phe Pro Asn Leu Pro Tyr Tyr Ile Asp Gly Asp Val Lys
    50                  55                  60 tta aca cag tct atg gcc atc ata cgt tat ata gct gac aag cac aac     240
Leu Thr Gln Ser Met Ala Ile Ile Arg Tyr Ile Ala Asp Lys His Asn
65                  70                  75                  80 atg ttg ggt ggt tgt cca aaa gag cgt gca gag att tca atg ctt gaa     288
Met Leu Gly Gly Cys Pro Lys Glu Arg Ala Glu Ile Ser Met Leu Glu
                85                  90                  95 gga gcg gtt ttg gat att aga tac ggt gtt tcg aga att gca tat agt     336
Gly Ala Val Leu Asp Ile Arg Tyr Gly Val Ser Arg Ile Ala Tyr Ser
            100                 105                 110 aaa gac ttt gaa act ctc aaa gtt gat ttt ctt agc aag cta cct gaa     384
Lys Asp Phe Glu Thr Leu Lys Val Asp Phe Leu Ser Lys Leu Pro Glu
        115                 120                 125 atg ctg aaa atg ttc gaa gat cgt tta tgt cat aaa aca tat tta aat     432
Met Leu Lys Met Phe Glu Asp Arg Leu Cys His Lys Thr Tyr Leu Asn
    130                 135                 140 ggt gat cat gta acc cat cct gac ttc atg ttg tat gac gct ctt gat     480
Gly Asp His Val Thr His Pro Asp Phe Met Leu Tyr Asp Ala Leu Asp
145                 150                 155                 160 gtt gtt tta tac atg gac cca atg tgc ctg gat gcg ttc cca aaa tta     528
Val Val Leu Tyr Met Asp Pro Met Cys Leu Asp Ala Phe Pro Lys Leu
                165                 170                 175 gtt tgt ttt aaa aaa cgt att gaa gct atc cca caa att gat aag tac     576
Val Cys Phe Lys Lys Arg Ile Glu Ala Ile Pro Gln Ile Asp Lys Tyr
            180                 185                 190 ttg aaa tcc agc aag tat ata gca tgg cct ttg cag ggc tgg caa gcc     624
Leu Lys Ser Ser Lys Tyr Ile Ala Trp Pro Leu Gln Gly Trp Gln Ala
        195                 200                 205 acg ttt ggt ggt ggc gac cat cct cca aaa tcg gat ctg gtt ccg cgt     672
Thr Phe Gly Gly Gly Asp His Pro Pro Lys Ser Asp Leu Val Pro Arg
    210                 215                 220
```

| | | | |
|---|---|---|---|
| gga tcc tct aga gtc gac ctg cag gca tgc aat gct tat tcc att aat<br>Gly Ser Ser Arg Val Asp Leu Gln Ala Cys Asn Ala Tyr Ser Ile Asn<br>225                230                   235              240 | 720 |

```
gga tcc tct aga gtc gac ctg cag gca tgc aat gct tat tcc att aat      720
Gly Ser Ser Arg Val Asp Leu Gln Ala Cys Asn Ala Tyr Ser Ile Asn
225                 230                 235                 240 caa aag gct tat tca aat act tac cag gag ttt act aat att gat caa      768
Gln Lys Ala Tyr Ser Asn Thr Tyr Gln Glu Phe Thr Asn Ile Asp Gln
                245                 250                 255 gca aaa gct tgg ggt aat gct cag tat aaa aag tat gga cta agc aaa      816
Ala Lys Ala Trp Gly Asn Ala Gln Tyr Lys Lys Tyr Gly Leu Ser Lys
            260                 265                 270 tca gaa aaa gaa gct ata gta tca tat act aaa agc gct agt gaa ata      864
Ser Glu Lys Glu Ala Ile Val Ser Tyr Thr Lys Ser Ala Ser Glu Ile
        275                 280                 285 aat gga aag cta aga caa aat aag gga gtt atc aat gga ttt cct tca      912
Asn Gly Lys Leu Arg Gln Asn Lys Gly Val Ile Asn Gly Phe Pro Ser
290                 295                 300 aat tta ata aaa caa gtt gaa ctt tta gat aaa tct ttt aat aaa atg      960
Asn Leu Ile Lys Gln Val Glu Leu Leu Asp Lys Ser Phe Asn Lys Met
305                 310                 315                 320 aag acc cct gaa aat att atg tta ttt aga ggc gac gac cct gct tat     1008
Lys Thr Pro Glu Asn Ile Met Leu Phe Arg Gly Asp Asp Pro Ala Tyr
                325                 330                 335 tta gga aca gaa ttt caa aac act ctt ctt aat tca aat ggt aca att     1056
Leu Gly Thr Glu Phe Gln Asn Thr Leu Leu Asn Ser Asn Gly Thr Ile
            340                 345                 350 aat aaa acg gct ttt gaa aag gct aaa gct aag ttt tta aat aaa gat     1104
Asn Lys Thr Ala Phe Glu Lys Ala Lys Ala Lys Phe Leu Asn Lys Asp
        355                 360                 365 aga ctt gaa tat gga tat att agt act tca tta atg aat gtt tct caa     1152
Arg Leu Glu Tyr Gly Tyr Ile Ser Thr Ser Leu Met Asn Val Ser Gln
370                 375                 380 ttt gca gga aga cca att att aca aaa ttt aaa gta gca aaa ggc tca     1200
Phe Ala Gly Arg Pro Ile Ile Thr Lys Phe Lys Val Ala Lys Gly Ser
385                 390                 395                 400 aag gca gga tat att gac cct att agt gct ttt cag gga caa ctt gaa     1248
Lys Ala Gly Tyr Ile Asp Pro Ile Ser Ala Phe Gln Gly Gln Leu Glu
                405                 410                 415 atg ttg ctt cct aga cat agt act tat cat ata gac gat atg aga ttg     1296
Met Leu Leu Pro Arg His Ser Thr Tyr His Ile Asp Asp Met Arg Leu
            420                 425                 430 tct tct gat ggt aaa caa ata ata att aca gca aca atg atg ggc aca     1344
Ser Ser Asp Gly Lys Gln Ile Ile Ile Thr Ala Thr Met Met Gly Thr
        435                 440                 445 gct atc aat cct aaa gaa ttc aga agg aaa caa aga aga aaa aga aga     1392
Ala Ile Asn Pro Lys Glu Phe Arg Arg Lys Gln Arg Arg Lys Arg Arg
450                 455                 460 ctg cag gcg gcc gca tcg tga                                         1413
Leu Gln Ala Ala Ala Ser
465                 470

<210> SEQ ID NO 20
<211> LENGTH: 470
<212> TYPE: PRT
<213> ORGANISM: Artificial Sequence
<220> FEATURE:
<223> OTHER INFORMATION: Includes GST sequences, ADP-ribosyl
      transferase C3 (C. botulinum) sequence and a random basic
      amino acid sequence.

<400> SEQUENCE: 20

Met Ser Pro Ile Leu Gly Tyr Trp Lys Ile Lys Gly Leu Val Gln Pro
1               5                   10                  15
```

-continued

```
Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
        50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Leu Val Pro Arg
        210                 215                 220

Gly Ser Ser Arg Val Asp Leu Gln Ala Cys Asn Ala Tyr Ser Ile Asn
225                 230                 235                 240

Gln Lys Ala Tyr Ser Asn Thr Tyr Gln Glu Phe Thr Asn Ile Asp Gln
                245                 250                 255

Ala Lys Ala Trp Gly Asn Ala Gln Tyr Lys Lys Tyr Gly Leu Ser Lys
                260                 265                 270

Ser Glu Lys Glu Ala Ile Val Ser Tyr Thr Lys Ser Ala Ser Glu Ile
            275                 280                 285

Asn Gly Lys Leu Arg Gln Asn Lys Gly Val Ile Asn Gly Phe Pro Ser
290                 295                 300

Asn Leu Ile Lys Gln Val Glu Leu Leu Asp Lys Ser Phe Asn Lys Met
305                 310                 315                 320

Lys Thr Pro Glu Asn Ile Met Leu Phe Arg Gly Asp Asp Pro Ala Tyr
                325                 330                 335

Leu Gly Thr Glu Phe Gln Asn Thr Leu Leu Asn Ser Asn Gly Thr Ile
                340                 345                 350

Asn Lys Thr Ala Phe Glu Lys Ala Lys Ala Lys Phe Leu Asn Lys Asp
            355                 360                 365

Arg Leu Glu Tyr Gly Tyr Ile Ser Thr Ser Leu Met Asn Val Ser Gln
370                 375                 380

Phe Ala Gly Arg Pro Ile Ile Thr Lys Phe Lys Val Ala Lys Gly Ser
385                 390                 395                 400

Lys Ala Gly Tyr Ile Asp Pro Ile Ser Ala Phe Gln Gly Gln Leu Glu
                405                 410                 415

Met Leu Leu Pro Arg His Ser Thr Tyr His Ile Asp Asp Met Arg Leu
                420                 425                 430
```

```
Ser Ser Asp Gly Lys Gln Ile Ile Thr Ala Thr Met Met Gly Thr
        435                 440                 445

Ala Ile Asn Pro Lys Glu Phe Arg Arg Lys Gln Arg Arg Lys Arg Arg
    450                 455                 460

Leu Gln Ala Ala Ala Ser
465                 470

<210> SEQ ID NO 21
<211> LENGTH: 16
<212> TYPE: PRT
<213> ORGANISM: Artificial Sequence
<220> FEATURE:
<223> OTHER INFORMATION: Random basic amino acid sequence of C3Basic1

<400> SEQUENCE: 21

Lys Arg Arg Arg Arg Arg Pro Lys Lys Arg Arg Arg Ala Lys Arg Arg
1               5                   10                  15

<210> SEQ ID NO 22
<211> LENGTH: 48
<212> TYPE: DNA
<213> ORGANISM: Artificial Sequence
<220> FEATURE:
<223> OTHER INFORMATION: Oligonucleotide used in the cloning of a
      random basic amino acid sequence in C3Basic1

<400> SEQUENCE: 22
aagagaaggc gaagaagacc taagaagaga cgaagggcga agaggaga                48

<210> SEQ ID NO 23
<211> LENGTH: 48
<212> TYPE: DNA
<213> ORGANISM: Artificial Sequence
<220> FEATURE:
<223> OTHER INFORMATION: Oligonucleotide used in the cloning of a
      random basic amino acid sequence in C3Basic1

<400> SEQUENCE: 23
ttctcttccg cttcttctgg attcttctct gcttcccgct tctcctct                48

<210> SEQ ID NO 24
<211> LENGTH: 792
<212> TYPE: DNA
<213> ORGANISM: Artificial Sequence
<220> FEATURE:
<223> OTHER INFORMATION: Sequence of C3Basic1: includes ADP-ribosyl
      transferase C3 (Clostridium botulinum) sequence and a sequence
      encoding a random basic amino acid sequence and a Histidine tag.
<220> FEATURE:
<221> NAME/KEY: CDS
<222> LOCATION: (1)..(792)
<223> OTHER INFORMATION:

<400> SEQUENCE: 24 gga tcc tct aga gtc gac ctg cag gca tgc aat gct tat tcc att aat      48
Gly Ser Ser Arg Val Asp Leu Gln Ala Cys Asn Ala Tyr Ser Ile Asn
1               5                   10                  15 caa aag gct tat tca aat act tac cag gag ttt act aat att gat caa     96
Gln Lys Ala Tyr Ser Asn Thr Tyr Gln Glu Phe Thr Asn Ile Asp Gln
                20                  25                  30 gca aaa gct tgg ggt aat gct cag tat aaa aag tat gga cta agc aaa    144
Ala Lys Ala Trp Gly Asn Ala Gln Tyr Lys Lys Tyr Gly Leu Ser Lys
            35                  40                  45 tca gaa aaa gaa gct ata gta tca tat act aaa agc gct agt gaa ata    192
Ser Glu Lys Glu Ala Ile Val Ser Tyr Thr Lys Ser Ala Ser Glu Ile
        50                  55                  60
```

```
aat gga aag cta aga caa aat aag gga gtt atc aat gga ttt cct tca    240
Asn Gly Lys Leu Arg Gln Asn Lys Gly Val Ile Asn Gly Phe Pro Ser
 65                  70                  75                  80 aat tta ata aaa caa gtt gaa ctt tta gat aaa tct ttt aat aaa atg    288
Asn Leu Ile Lys Gln Val Glu Leu Leu Asp Lys Ser Phe Asn Lys Met
                 85                  90                  95 aag acc cct gaa aat att atg tta ttt aga ggc gac gac cct gct tat    336
Lys Thr Pro Glu Asn Ile Met Leu Phe Arg Gly Asp Asp Pro Ala Tyr
            100                 105                 110 tta gga aca gaa ttt caa aac act ctt ctt aat tca aat ggt aca att    384
Leu Gly Thr Glu Phe Gln Asn Thr Leu Leu Asn Ser Asn Gly Thr Ile
        115                 120                 125 aat aaa acg gct ttt gaa aag gct aaa gct aag ttt tta aat aaa gat    432
Asn Lys Thr Ala Phe Glu Lys Ala Lys Ala Lys Phe Leu Asn Lys Asp
130                 135                 140 aga ctt gaa tat gga tat att agt act tca tta atg aat gtt tct caa    480
Arg Leu Glu Tyr Gly Tyr Ile Ser Thr Ser Leu Met Asn Val Ser Gln
145                 150                 155                 160 ttt gca gga aga cca att att aca aaa ttt aaa gta gca aaa ggc tca    528
Phe Ala Gly Arg Pro Ile Ile Thr Lys Phe Lys Val Ala Lys Gly Ser
                165                 170                 175 aag gca gga tat att gac cct att agt gct ttt cag gga caa ctt gaa    576
Lys Ala Gly Tyr Ile Asp Pro Ile Ser Ala Phe Gln Gly Gln Leu Glu
            180                 185                 190 atg ttg ctt cct aga cat agt act tat cat ata gac gat atg aga ttg    624
Met Leu Leu Pro Arg His Ser Thr Tyr His Ile Asp Asp Met Arg Leu
        195                 200                 205 tct tct gat ggt aaa caa ata ata att aca gca aca atg atg ggc aca    672
Ser Ser Asp Gly Lys Gln Ile Ile Ile Thr Ala Thr Met Met Gly Thr
210                 215                 220 gct atc aat cct aaa gaa ttc aag aga agg cga aga aga cct aag aag    720
Ala Ile Asn Pro Lys Glu Phe Lys Arg Arg Arg Arg Pro Lys Lys
225                 230                 235                 240 aga cga agg gcg aag agg aga cac cac cac cac cac cac gtc gac tcg    768
Arg Arg Arg Ala Lys Arg Arg His His His His His His Val Asp Ser
                245                 250                 255 agc ggc cgc atc gtg act gac tga                                    792
Ser Gly Arg Ile Val Thr Asp
            260
```

<210> SEQ ID NO 25
<211> LENGTH: 263
<212> TYPE: PRT
<213> ORGANISM: Artificial Sequence
<220> FEATURE:
<223> OTHER INFORMATION: Sequence of C3Basic1:  includes ADP-ribosyl
      transferase C3 (Clostridium botulinum) sequence and a sequence
      encoding a random basic amino acid sequence and a Histidine tag.

<400> SEQUENCE: 25

```
Gly Ser Ser Arg Val Asp Leu Gln Ala Cys Asn Ala Tyr Ser Ile Asn
  1               5                  10                  15

Gln Lys Ala Tyr Ser Asn Thr Tyr Gln Glu Phe Thr Asn Ile Asp Gln
             20                  25                  30

Ala Lys Ala Trp Gly Asn Ala Gln Tyr Lys Lys Tyr Gly Leu Ser Lys
         35                  40                  45

Ser Glu Lys Glu Ala Ile Val Ser Tyr Thr Lys Ser Ala Ser Glu Ile
     50                  55                  60

Asn Gly Lys Leu Arg Gln Asn Lys Gly Val Ile Asn Gly Phe Pro Ser
 65                  70                  75                  80
```

```
Asn Leu Ile Lys Gln Val Glu Leu Leu Asp Lys Ser Phe Asn Lys Met
                85                  90                  95

Lys Thr Pro Glu Asn Ile Met Leu Phe Arg Gly Asp Pro Ala Tyr
            100                 105                 110

Leu Gly Thr Glu Phe Gln Asn Thr Leu Leu Asn Ser Asn Gly Thr Ile
        115                 120                 125

Asn Lys Thr Ala Phe Glu Lys Ala Lys Ala Lys Phe Leu Asn Lys Asp
    130                 135                 140

Arg Leu Glu Tyr Gly Tyr Ile Ser Thr Ser Leu Met Asn Val Ser Gln
145                 150                 155                 160

Phe Ala Gly Arg Pro Ile Ile Thr Lys Phe Lys Val Ala Lys Gly Ser
                165                 170                 175

Lys Ala Gly Tyr Ile Asp Pro Ile Ser Ala Phe Gln Gly Gln Leu Glu
            180                 185                 190

Met Leu Leu Pro Arg His Ser Thr Tyr His Ile Asp Asp Met Arg Leu
        195                 200                 205

Ser Ser Asp Gly Lys Gln Ile Ile Ile Thr Ala Thr Met Met Gly Thr
    210                 215                 220

Ala Ile Asn Pro Lys Glu Phe Lys Arg Arg Arg Arg Pro Lys Lys
225                 230                 235                 240

Arg Arg Arg Ala Lys Arg Arg His His His His His Val Asp Ser
                245                 250                 255

Ser Gly Arg Ile Val Thr Asp
            260

<210> SEQ ID NO 26
<211> LENGTH: 13
<212> TYPE: PRT
<213> ORGANISM: Artificial Sequence
<220> FEATURE:
<223> OTHER INFORMATION: Random amino acid sequence of C3Basic2

<400> SEQUENCE: 26

Lys Arg Arg Arg Arg Lys Lys Arg Arg Gln Arg Arg Arg
1               5                   10

<210> SEQ ID NO 27
<211> LENGTH: 39
<212> TYPE: DNA
<213> ORGANISM: Artificial Sequence
<220> FEATURE:
<223> OTHER INFORMATION: Oligonucleotide used in the cloning of a
      random basic amino acid sequence in C3Basic2

<400> SEQUENCE: 27
aagcgtcgac gtagaaagaa acgtagacag cgtagacgt                          39

<210> SEQ ID NO 28
<211> LENGTH: 39
<212> TYPE: DNA
<213> ORGANISM: Artificial Sequence
<220> FEATURE:
<223> OTHER INFORMATION: Oligonucleotide used in the cloning of a
      random basic amino acid sequence in C3Basic2

<400> SEQUENCE: 28
ttcgcagctg catctttctt tgcatctgtc gcatctgca                          39
```

<210> SEQ ID NO 29
<211> LENGTH: 783
<212> TYPE: DNA
<213> ORGANISM: Artificial Sequence
<220> FEATURE:
<223> OTHER INFORMATION: Sequence of C3Basic2: includes sequences from ADP-ribosyl-transferase C3 (Clostridium botulinum) and a sequence encoding a random basic amino acid sequence and a histidine tag.
<220> FEATURE:
<221> NAME/KEY: CDS
<222> LOCATION: (1)..(783)
<223> OTHER INFORMATION:

<400> SEQUENCE: 29

```
gga tcc tct aga gtc gac ctg cag gca tgc aat gct tat tcc att aat      48
Gly Ser Ser Arg Val Asp Leu Gln Ala Cys Asn Ala Tyr Ser Ile Asn
1               5                   10                  15 caa aag gct tat tca aat act tac cag gag ttt act aat att gat caa      96
Gln Lys Ala Tyr Ser Asn Thr Tyr Gln Glu Phe Thr Asn Ile Asp Gln
            20                  25                  30 gca aaa gct tgg ggt aat gct cag tat aaa aag tat gga cta agc aaa     144
Ala Lys Ala Trp Gly Asn Ala Gln Tyr Lys Lys Tyr Gly Leu Ser Lys
        35                  40                  45 tca gaa aaa gaa gct ata gta tca tat act aaa agc gct agt gaa ata     192
Ser Glu Lys Glu Ala Ile Val Ser Tyr Thr Lys Ser Ala Ser Glu Ile
50                  55                  60 aat gga aag cta aga caa aat aag gga gtt atc aat gga ttt cct tca     240
Asn Gly Lys Leu Arg Gln Asn Lys Gly Val Ile Asn Gly Phe Pro Ser
65                  70                  75                  80 aat tta ata aaa caa gtt gaa ctt tta gat aaa tct ttt aat aaa atg     288
Asn Leu Ile Lys Gln Val Glu Leu Leu Asp Lys Ser Phe Asn Lys Met
                85                  90                  95 aag acc cct gaa aat att atg tta ttt aga ggc gac gac cct gct tat     336
Lys Thr Pro Glu Asn Ile Met Leu Phe Arg Gly Asp Asp Pro Ala Tyr
            100                 105                 110 tta gga aca gaa ttt caa aac act ctt ctt aat tca aat ggt aca att     384
Leu Gly Thr Glu Phe Gln Asn Thr Leu Leu Asn Ser Asn Gly Thr Ile
        115                 120                 125 aat aaa acg gct ttt gaa aag gct aaa gct aag ttt tta aat aaa gat     432
Asn Lys Thr Ala Phe Glu Lys Ala Lys Ala Lys Phe Leu Asn Lys Asp
    130                 135                 140 aga ctt gaa tat gga tat att agt act tca tta atg aat gtt tct caa     480
Arg Leu Glu Tyr Gly Tyr Ile Ser Thr Ser Leu Met Asn Val Ser Gln
145                 150                 155                 160 ttt gca gga aga cca att att aca aaa ttt aaa gta gca aaa ggc tca     528
Phe Ala Gly Arg Pro Ile Ile Thr Lys Phe Lys Val Ala Lys Gly Ser
                165                 170                 175 aag gca gga tat att gac cct att agt gct ttt cag gga caa ctt gaa     576
Lys Ala Gly Tyr Ile Asp Pro Ile Ser Ala Phe Gln Gly Gln Leu Glu
            180                 185                 190 atg ttg ctt cct aga cat agt act tat cat ata gac gat atg aga ttg     624
Met Leu Leu Pro Arg His Ser Thr Tyr His Ile Asp Asp Met Arg Leu
        195                 200                 205 tct tct gat ggt aaa caa ata ata att aca gca aca atg atg ggc aca     672
Ser Ser Asp Gly Lys Gln Ile Ile Ile Thr Ala Thr Met Met Gly Thr
    210                 215                 220 gct atc aat cct aaa gaa ttc aag cgt cga cgt aga aag aaa cgt aga     720
Ala Ile Asn Pro Lys Glu Phe Lys Arg Arg Arg Lys Lys Arg Arg
225                 230                 235                 240 cag cgt aga cgt cac cac cac cac cac cac gtc gac tcg agc ggc cgc     768
Gln Arg Arg Arg His His His His His His Val Asp Ser Ser Gly Arg
                245                 250                 255
```

```
            atc gtg act gac tga                                              783
            Ile Val Thr Asp
                    260

<210> SEQ ID NO 30
<211> LENGTH: 260
<212> TYPE: PRT
<213> ORGANISM: Artificial Sequence
<220> FEATURE:
<223> OTHER INFORMATION: Sequence of C3Basic2:  includes sequences from
      ADP-ribosyl-transferase C3 (Clostridium botulinum) and a sequence
      encoding a random basic amino acid sequence and a histidine tag.

<400> SEQUENCE: 30

Gly Ser Ser Arg Val Asp Leu Gln Ala Cys Asn Ala Tyr Ser Ile Asn
1               5                   10                  15

Gln Lys Ala Tyr Ser Asn Thr Tyr Gln Glu Phe Thr Asn Ile Asp Gln
            20                  25                  30

Ala Lys Ala Trp Gly Asn Ala Gln Tyr Lys Tyr Gly Leu Ser Lys
        35                  40                  45

Ser Glu Lys Glu Ala Ile Val Ser Tyr Thr Lys Ser Ala Ser Glu Ile
    50                  55                  60

Asn Gly Lys Leu Arg Gln Asn Lys Gly Val Ile Asn Gly Phe Pro Ser
65                  70                  75                  80

Asn Leu Ile Lys Gln Val Glu Leu Leu Asp Lys Ser Phe Asn Lys Met
                85                  90                  95

Lys Thr Pro Glu Asn Ile Met Leu Phe Arg Gly Asp Pro Ala Tyr
            100                 105                 110

Leu Gly Thr Glu Phe Gln Asn Thr Leu Leu Asn Ser Asn Gly Thr Ile
        115                 120                 125

Asn Lys Thr Ala Phe Glu Lys Ala Lys Ala Lys Phe Leu Asn Lys Asp
130                 135                 140

Arg Leu Glu Tyr Gly Tyr Ile Ser Thr Ser Leu Met Asn Val Ser Gln
145                 150                 155                 160

Phe Ala Gly Arg Pro Ile Ile Thr Lys Phe Lys Val Ala Lys Gly Ser
                165                 170                 175

Lys Ala Gly Tyr Ile Asp Pro Ile Ser Ala Phe Gln Gly Gln Leu Glu
            180                 185                 190

Met Leu Leu Pro Arg His Ser Thr Tyr His Ile Asp Asp Met Arg Leu
        195                 200                 205

Ser Ser Asp Gly Lys Gln Ile Ile Ile Thr Ala Thr Met Met Gly Thr
    210                 215                 220

Ala Ile Asn Pro Lys Glu Phe Lys Arg Arg Arg Lys Lys Arg Arg
225                 230                 235                 240

Gln Arg Arg Arg His His His His His Val Asp Ser Ser Gly Arg
                245                 250                 255

Ile Val Thr Asp
        260

<210> SEQ ID NO 31
<211> LENGTH: 9
<212> TYPE: PRT
<213> ORGANISM: Artificial Sequence
<220> FEATURE:
<223> OTHER INFORMATION: Reverse HIV-1 Tat amino acid sequence of
      C3Basic3
```

-continued

```
<400> SEQUENCE: 31

Arg Arg Lys Gln Arg Arg Lys Arg Arg
1               5

<210> SEQ ID NO 32
<211> LENGTH: 27
<212> TYPE: DNA
<213> ORGANISM: Artificial Sequence
<220> FEATURE:
<223> OTHER INFORMATION: Oligonucleotide used in the cloning of a
      reverse HIV Tat sequence in C3Basic3

<400> SEQUENCE: 32
agaaggaaac aaagaagaaa aagaaga                                      27

<210> SEQ ID NO 33
<211> LENGTH: 27
<212> TYPE: DNA
<213> ORGANISM: Artificial Sequence
<220> FEATURE:
<223> OTHER INFORMATION: Oligonucleotide used in the cloning of a
      reverse HIV Tat sequence in C3Basic3

<400> SEQUENCE: 33
tcttcctttg tttcttcttt ttcttct                                      27

<210> SEQ ID NO 34
<211> LENGTH: 771
<212> TYPE: DNA
<213> ORGANISM: Artificial Sequence
<220> FEATURE:
<223> OTHER INFORMATION: Sequence of C3Basic3: includes sequences from
      ADP-ribosyl tranferase C3 (C. botulinum) and a sequence encoding
      a reverse HIV-1 Tat amino acid sequence and a Histidine tag
<220> FEATURE:
<221> NAME/KEY: CDS
<222> LOCATION: (1)..(771)
<223> OTHER INFORMATION:

<400> SEQUENCE: 34 gga tcc tct aga gtc gac ctg cag gca tgc aat gct tat tcc att aat      48
Gly Ser Ser Arg Val Asp Leu Gln Ala Cys Asn Ala Tyr Ser Ile Asn
1               5                   10                  15 caa aag gct tat tca aat act tac cag gag ttt act aat att gat caa      96
Gln Lys Ala Tyr Ser Asn Thr Tyr Gln Glu Phe Thr Asn Ile Asp Gln
            20                  25                  30 gca aaa gct tgg ggt aat gct cag tat aaa aag tat gga cta agc aaa     144
Ala Lys Ala Trp Gly Asn Ala Gln Tyr Lys Lys Tyr Gly Leu Ser Lys
        35                  40                  45 tca gaa aaa gaa gct ata gta tca tat act aaa agc gct agt gaa ata     192
Ser Glu Lys Glu Ala Ile Val Ser Tyr Thr Lys Ser Ala Ser Glu Ile
    50                  55                  60 aat gga aag cta aga caa aat aag gga gtt atc aat gga ttt cct tca     240
Asn Gly Lys Leu Arg Gln Asn Lys Gly Val Ile Asn Gly Phe Pro Ser
65                  70                  75                  80 aat tta ata aaa caa gtt gaa ctt tta gat aaa tct ttt aat aaa atg     288
Asn Leu Ile Lys Gln Val Glu Leu Leu Asp Lys Ser Phe Asn Lys Met
                85                  90                  95 aag acc cct gaa aat att atg tta ttt aga ggc gac gac cct gct tat     336
Lys Thr Pro Glu Asn Ile Met Leu Phe Arg Gly Asp Asp Pro Ala Tyr
            100                 105                 110 tta gga aca gaa ttt caa aac act ctt ctt aat tca aat ggt aca att     384
Leu Gly Thr Glu Phe Gln Asn Thr Leu Leu Asn Ser Asn Gly Thr Ile
        115                 120                 125
```

```
aat aaa acg gct ttt gaa aag gct aaa gct aag ttt tta aat aaa gat    432
Asn Lys Thr Ala Phe Glu Lys Ala Lys Ala Lys Phe Leu Asn Lys Asp
    130                 135                 140 aga ctt gaa tat gga tat att agt act tca tta atg aat gtt tct caa    480
Arg Leu Glu Tyr Gly Tyr Ile Ser Thr Ser Leu Met Asn Val Ser Gln
145                 150                 155                 160 ttt gca gga aga cca att att aca aaa ttt aaa gta gca aaa ggc tca    528
Phe Ala Gly Arg Pro Ile Ile Thr Lys Phe Lys Val Ala Lys Gly Ser
                165                 170                 175 aag gca gga tat att gac cct att agt gct ttt cag gga caa ctt gaa    576
Lys Ala Gly Tyr Ile Asp Pro Ile Ser Ala Phe Gln Gly Gln Leu Glu
            180                 185                 190 atg ttg ctt cct aga cat agt act tat cat ata gac gat atg aga ttg    624
Met Leu Leu Pro Arg His Ser Thr Tyr His Ile Asp Asp Met Arg Leu
        195                 200                 205 tct tct gat ggt aaa caa ata ata att aca gca aca atg atg ggc aca    672
Ser Ser Asp Gly Lys Gln Ile Ile Ile Thr Ala Thr Met Met Gly Thr
    210                 215                 220 gct atc aat cct aaa gaa ttc aga agg aaa caa aga aga aaa aga aga    720
Ala Ile Asn Pro Lys Glu Phe Arg Arg Lys Gln Arg Arg Lys Arg Arg
225                 230                 235                 240 cac cac cac cac cac cac gtc gac tcg agc ggc cgc atc gtg act gac    768
His His His His His His Val Asp Ser Ser Gly Arg Ile Val Thr Asp
                245                 250                 255 tga                                                                771
```

<210> SEQ ID NO 35
<211> LENGTH: 256
<212> TYPE: PRT
<213> ORGANISM: Artificial Sequence
<220> FEATURE:
<223> OTHER INFORMATION: Sequence of C3Basic3: includes sequences from
      ADP-ribosyl tranferase C3 (C. botulinum) and a sequence encoding
      a reverse HIV-1 Tat amino acid sequence and a Histidine tag

<400> SEQUENCE: 35

```
Gly Ser Ser Arg Val Asp Leu Gln Ala Cys Asn Ala Tyr Ser Ile Asn
1               5                   10                  15

Gln Lys Ala Tyr Ser Asn Thr Tyr Gln Glu Phe Thr Asn Ile Asp Gln
            20                  25                  30

Ala Lys Ala Trp Gly Asn Ala Gln Tyr Lys Lys Tyr Gly Leu Ser Lys
        35                  40                  45

Ser Glu Lys Glu Ala Ile Val Ser Tyr Thr Lys Ser Ala Ser Glu Ile
    50                  55                  60

Asn Gly Lys Leu Arg Gln Asn Lys Gly Val Ile Asn Gly Phe Pro Ser
65                  70                  75                  80

Asn Leu Ile Lys Gln Val Glu Leu Leu Asp Lys Ser Phe Asn Lys Met
                85                  90                  95

Lys Thr Pro Glu Asn Ile Met Leu Phe Arg Gly Asp Asp Pro Ala Tyr
            100                 105                 110

Leu Gly Thr Glu Phe Gln Asn Thr Leu Leu Asn Ser Asn Gly Thr Ile
        115                 120                 125

Asn Lys Thr Ala Phe Glu Lys Ala Lys Ala Lys Phe Leu Asn Lys Asp
    130                 135                 140

Arg Leu Glu Tyr Gly Tyr Ile Ser Thr Ser Leu Met Asn Val Ser Gln
145                 150                 155                 160

Phe Ala Gly Arg Pro Ile Ile Thr Lys Phe Lys Val Ala Lys Gly Ser
                165                 170                 175
```

```
                Lys Ala Gly Tyr Ile Asp Pro Ile Ser Ala Phe Gln Gly Gln Leu Glu
                            180                 185                 190

Met Leu Leu Pro Arg His Ser Thr Tyr His Ile Asp Met Arg Leu
                        195                 200                 205

Ser Ser Asp Gly Lys Gln Ile Ile Ile Thr Ala Thr Met Met Gly Thr
                    210                 215                 220

Ala Ile Asn Pro Lys Glu Phe Arg Arg Lys Gln Arg Lys Arg Arg
                225                 230                 235                 240

His His His His His His Val Asp Ser Ser Gly Arg Ile Val Thr Asp
                                245                 250                 255

<210> SEQ ID NO 36
<211> LENGTH: 887
<212> TYPE: DNA
<213> ORGANISM: Artificial Sequence
<220> FEATURE:
<223> OTHER INFORMATION: Sequence of C3APLT:  includes sequences from
      ADP-ribosyl transferase C3 (Clostridium botulinum) and a sequence
      encoding a proline rich region.
<220> FEATURE:
<221> NAME/KEY: CDS
<222> LOCATION: (1)..(747)
<223> OTHER INFORMATION:

<400> SEQUENCE: 36 gga tcc tct aga gtc gac ctg cag gca tgc aat gct tat tcc att aat       48
Gly Ser Ser Arg Val Asp Leu Gln Ala Cys Asn Ala Tyr Ser Ile Asn
1               5                  10                  15 caa aag gct tat tca aat act tac cag gag ttt act aat att gat caa       96
Gln Lys Ala Tyr Ser Asn Thr Tyr Gln Glu Phe Thr Asn Ile Asp Gln
            20                  25                  30 gca aaa gct tgg ggt aat gct cag tat aaa aag tat gga cta agc aaa      144
Ala Lys Ala Trp Gly Asn Ala Gln Tyr Lys Lys Tyr Gly Leu Ser Lys
        35                  40                  45 tca gaa aaa gaa gct ata gta tca tat act aaa agc gct agt gaa ata      192
Ser Glu Lys Glu Ala Ile Val Ser Tyr Thr Lys Ser Ala Ser Glu Ile
    50                  55                  60 aat gga aag cta aga caa aat aag gga gtt atc aat gga ttt cct tca      240
Asn Gly Lys Leu Arg Gln Asn Lys Gly Val Ile Asn Gly Phe Pro Ser
65                  70                  75                  80 aat tta ata aaa caa gtt gaa ctt tta gat aaa tct ttt aat aaa atg      288
Asn Leu Ile Lys Gln Val Glu Leu Leu Asp Lys Ser Phe Asn Lys Met
                85                  90                  95 aag acc cct gaa aat att atg tta ttt aga ggc gac gac cct gct tat      336
Lys Thr Pro Glu Asn Ile Met Leu Phe Arg Gly Asp Asp Pro Ala Tyr
            100                 105                 110 tta gga aca gaa ttt caa aac act ctt ctt aat tca aat ggt aca att      384
Leu Gly Thr Glu Phe Gln Asn Thr Leu Leu Asn Ser Asn Gly Thr Ile
        115                 120                 125 aat aaa acg gct ttt gaa aag gct aaa gct aag ttt tta aat aaa gat      432
Asn Lys Thr Ala Phe Glu Lys Ala Lys Ala Lys Phe Leu Asn Lys Asp
    130                 135                 140 aga ctt gaa tat gga tat att agt act tca tta atg aat gtt tct caa      480
Arg Leu Glu Tyr Gly Tyr Ile Ser Thr Ser Leu Met Asn Val Ser Gln
145                 150                 155                 160 ttt gca gga aga cca att att aca aaa ttt aaa gta gca aaa ggc tca      528
Phe Ala Gly Arg Pro Ile Ile Thr Lys Phe Lys Val Ala Lys Gly Ser
                165                 170                 175 aag gca gga tat att gac cct att agt gct ttt gca gga caa ctt gaa      576
Lys Ala Gly Tyr Ile Asp Pro Ile Ser Ala Phe Ala Gly Gln Leu Glu
            180                 185                 190
```

```
atg ttg ctt cct aga cat agt act tat cat ata gac gat atg aga ttg      624
Met Leu Leu Pro Arg His Ser Thr Tyr His Ile Asp Asp Met Arg Leu
        195                 200                 205 tct tct gat ggt aaa caa ata ata att aca gca aca atg atg ggc aca      672
Ser Ser Asp Gly Lys Gln Ile Ile Ile Thr Ala Thr Met Met Gly Thr
    210                 215                 220 gct atc aat cct aaa gaa ttc gtg atg aat ccc gca aac gcg caa ggc      720
Ala Ile Asn Pro Lys Glu Phe Val Met Asn Pro Ala Asn Ala Gln Gly
225                 230                 235                 240 aga cat aca ccc ggt acc aga ctc tag agctagagaa ggagtttcac            767
Arg His Thr Pro Gly Thr Arg Leu
                245 ttcaatcgct acttgacccg tcggcgaagg atcgagatcg cccacgccct gtgcctcacg    827 gagcgccaga taaagatttg gttccagaat cggcgcatga agtggaagaa ggagaactga    887
```

<210> SEQ ID NO 37
<211> LENGTH: 248
<212> TYPE: PRT
<213> ORGANISM: Artificial Sequence
<220> FEATURE:
<223> OTHER INFORMATION: Sequence of C3APLT: includes sequences from
      ADP-ribosyl transferase C3 (Clostridium botulinum) and a sequence
      encoding a proline rich region.

<400> SEQUENCE: 37

```
Gly Ser Ser Arg Val Asp Leu Gln Ala Cys Asn Ala Tyr Ser Ile Asn
1               5                   10                  15

Gln Lys Ala Tyr Ser Asn Thr Tyr Gln Glu Phe Thr Asn Ile Asp Gln
            20                  25                  30

Ala Lys Ala Trp Gly Asn Ala Gln Tyr Lys Lys Tyr Gly Leu Ser Lys
        35                  40                  45

Ser Glu Lys Glu Ala Ile Val Ser Tyr Thr Lys Ser Ala Ser Glu Ile
    50                  55                  60

Asn Gly Lys Leu Arg Gln Asn Lys Gly Val Ile Asn Gly Phe Pro Ser
65                  70                  75                  80

Asn Leu Ile Lys Gln Val Glu Leu Leu Asp Lys Ser Phe Asn Lys Met
                85                  90                  95

Lys Thr Pro Glu Asn Ile Met Leu Phe Arg Gly Asp Pro Ala Tyr
            100                 105                 110

Leu Gly Thr Glu Phe Gln Asn Thr Leu Leu Asn Ser Asn Gly Thr Ile
        115                 120                 125

Asn Lys Thr Ala Phe Glu Lys Ala Lys Ala Lys Phe Leu Asn Lys Asp
    130                 135                 140

Arg Leu Glu Tyr Gly Tyr Ile Ser Thr Ser Leu Met Asn Val Ser Gln
145                 150                 155                 160

Phe Ala Gly Arg Pro Ile Ile Thr Lys Phe Lys Val Ala Lys Gly Ser
                165                 170                 175

Lys Ala Gly Tyr Ile Asp Pro Ile Ser Ala Phe Ala Gly Gln Leu Glu
            180                 185                 190

Met Leu Leu Pro Arg His Ser Thr Tyr His Ile Asp Asp Met Arg Leu
        195                 200                 205

Ser Ser Asp Gly Lys Gln Ile Ile Ile Thr Ala Thr Met Met Gly Thr
    210                 215                 220

Ala Ile Asn Pro Lys Glu Phe Val Met Asn Pro Ala Asn Ala Gln Gly
225                 230                 235                 240

Arg His Thr Pro Gly Thr Arg Leu
                245
```

<210> SEQ ID NO 38
<211> LENGTH: 37
<212> TYPE: DNA
<213> ORGANISM: Artificial Sequence
<220> FEATURE:
<223> OTHER INFORMATION: Oligonucleotide used in the cloning of
      C3APLT in pET vector

<400> SEQUENCE: 38
ggatctggtt ccgcgtcata tgtctagagt cgacctg                                37

<210> SEQ ID NO 39
<211> LENGTH: 32
<212> TYPE: DNA
<213> ORGANISM: Artificial Sequence
<220> FEATURE:
<223> OTHER INFORMATION: Oligonucleotide used in the cloning of
      C3APLT in pET vector

<400> SEQUENCE: 39
cgcggatcca ttagttctcc ttcttccact tc                                     32

<210> SEQ ID NO 40
<211> LENGTH: 24
<212> TYPE: DNA
<213> ORGANISM: Artificial Sequence
<220> FEATURE:
<223> OTHER INFORMATION: Oligonucleotide used in the sequencing of
      C3APLT

<400> SEQUENCE: 40
aaattaatac gactcactat aggg                                              24

<210> SEQ ID NO 41
<211> LENGTH: 19
<212> TYPE: DNA
<213> ORGANISM: Artificial Sequence
<220> FEATURE:
<223> OTHER INFORMATION: Oligonucleotide used in the sequencing of
      C3APLT

<400> SEQUENCE: 41
gctagttatt gctcagcgg                                                    19

<210> SEQ ID NO 42
<211> LENGTH: 888
<212> TYPE: DNA
<213> ORGANISM: Artificial Sequence
<220> FEATURE:
<223> OTHER INFORMATION: Sequence of C3APLT in a pET vector: includes
      sequences from ADP-ribosyl transferase C3 (Clostridium botulinum)
      and a sequence encoding a proline rich region.
<220> FEATURE:
<221> NAME/KEY: CDS
<222> LOCATION: (1)..(744)
<223> OTHER INFORMATION:

<400> SEQUENCE: 42 atg tct aga gtc gca ctg cag gca tgc aat gct tat tcc att aat caa         48
Met Ser Arg Val Ala Leu Gln Ala Cys Asn Ala Tyr Ser Ile Asn Gln
1               5                   10                  15 aag gct tat tca aat act tac cag gag ttt act aat att gat caa gca         96
Lys Ala Tyr Ser Asn Thr Tyr Gln Glu Phe Thr Asn Ile Asp Gln Ala
            20                  25                  30 aaa gct tgg ggt aat gct cag tat aaa aag tat gga cta agc aaa tca        144
Lys Ala Trp Gly Asn Ala Gln Tyr Lys Lys Tyr Gly Leu Ser Lys Ser
        35                  40                  45

-continued

```
gaa aaa gaa gct ata gta tca tat act aaa agc gct agt gaa ata aat      192
Glu Lys Glu Ala Ile Val Ser Tyr Thr Lys Ser Ala Ser Glu Ile Asn
 50                  55                  60 gga aag cta aga caa aat aag gga gtt atc aat gga ttt cct tca aat      240
Gly Lys Leu Arg Gln Asn Lys Gly Val Ile Asn Gly Phe Pro Ser Asn
 65                  70                  75                  80 tta ata aaa caa gtt gaa ctt tta gat aaa tct ttt aat aaa atg aag      288
Leu Ile Lys Gln Val Glu Leu Leu Asp Lys Ser Phe Asn Lys Met Lys
                 85                  90                  95 acc cct gaa aat att atg tta ttt aga ggc gac gac cct gct tat tta      336
Thr Pro Glu Asn Ile Met Leu Phe Arg Gly Asp Asp Pro Ala Tyr Leu
            100                 105                 110 gga aca gaa ttt caa aac act ctt ctt aat tca aat ggt aca att aat      384
Gly Thr Glu Phe Gln Asn Thr Leu Leu Asn Ser Asn Gly Thr Ile Asn
        115                 120                 125 aaa acg gct ttt gaa aag gct aaa gct aag ttt tta aat aaa gat aga      432
Lys Thr Ala Phe Glu Lys Ala Lys Ala Lys Phe Leu Asn Lys Asp Arg
    130                 135                 140 ctt gaa tat gga tat att agt act tca tta atg aat gtt tct caa ttt      480
Leu Glu Tyr Gly Tyr Ile Ser Thr Ser Leu Met Asn Val Ser Gln Phe
145                 150                 155                 160 gca gga aga cca att att aca aaa ttt aaa gta gca aaa ggc tca aag      528
Ala Gly Arg Pro Ile Ile Thr Lys Phe Lys Val Ala Lys Gly Ser Lys
                165                 170                 175 gca gga tat att gac cct att agt gct ttt gca gga caa ctt gaa atg      576
Ala Gly Tyr Ile Asp Pro Ile Ser Ala Phe Ala Gly Gln Leu Glu Met
            180                 185                 190 ttg ctt cct aga cat agt act tat cat ata gac gat atg aga ttg tct      624
Leu Leu Pro Arg His Ser Thr Tyr His Ile Asp Asp Met Arg Leu Ser
        195                 200                 205 tct gat ggt aaa caa ata ata att aca gca aca atg atg ggc aca gct      672
Ser Asp Gly Lys Gln Ile Ile Ile Thr Ala Thr Met Met Gly Thr Ala
    210                 215                 220 atc aat cct aaa gaa ttc gtg atg aat ccc gca aac gcg caa ggc aga      720
Ile Asn Pro Lys Glu Phe Val Met Asn Pro Ala Asn Ala Gln Gly Arg
225                 230                 235                 240 cat aca ccc ggt acc aga ctc tag agctagagaa ggagtttcac ttcaatcgct    774
His Thr Pro Gly Thr Arg Leu
                245 acttgacccg tcggcgaagg atcgagatcg cccacgccct gtgcctcacg gagcgccaga    834 taaagatttg gttccagaat cggcgcatga agtggaagaa ggaggactaa ctga          888
```

<210> SEQ ID NO 43
<211> LENGTH: 247
<212> TYPE: PRT
<213> ORGANISM: Artificial Sequence
<220> FEATURE:
<223> OTHER INFORMATION: Sequence of C3APLT in a pET vector: includes
      sequences from ADP-ribosyl transferase C3 (Clostridium botulinum)
      and a sequence encoding a proline rich region.

<400> SEQUENCE: 43

```
Met Ser Arg Val Ala Leu Gln Ala Cys Asn Ala Tyr Ser Ile Asn Gln
  1               5                  10                  15

Lys Ala Tyr Ser Asn Thr Tyr Gln Glu Phe Thr Asn Ile Asp Gln Ala
                 20                  25                  30

Lys Ala Trp Gly Asn Ala Gln Tyr Lys Lys Tyr Gly Leu Ser Lys Ser
             35                  40                  45

Glu Lys Glu Ala Ile Val Ser Tyr Thr Lys Ser Ala Ser Glu Ile Asn
 50                  55                  60
```

```
                        -continued

Gly Lys Leu Arg Gln Asn Lys Gly Val Ile Asn Gly Phe Pro Ser Asn
65                  70                  75                  80

Leu Ile Lys Gln Val Glu Leu Leu Asp Lys Ser Phe Asn Lys Met Lys
                85                  90                  95

Thr Pro Glu Asn Ile Met Leu Phe Arg Gly Asp Pro Ala Tyr Leu
            100                 105                 110

Gly Thr Glu Phe Gln Asn Thr Leu Leu Asn Ser Asn Gly Thr Ile Asn
                115                 120                 125

Lys Thr Ala Phe Glu Lys Ala Lys Ala Lys Phe Leu Asn Lys Asp Arg
130                 135                 140

Leu Glu Tyr Gly Tyr Ile Ser Thr Ser Leu Met Asn Val Ser Gln Phe
145                 150                 155                 160

Ala Gly Arg Pro Ile Ile Thr Lys Phe Lys Val Ala Lys Gly Ser Lys
                165                 170                 175

Ala Gly Tyr Ile Asp Pro Ile Ser Ala Phe Ala Gly Gln Leu Glu Met
                180                 185                 190

Leu Leu Pro Arg His Ser Thr Tyr His Ile Asp Asp Met Arg Leu Ser
                195                 200                 205

Ser Asp Gly Lys Gln Ile Ile Ile Thr Ala Thr Met Met Gly Thr Ala
210                 215                 220

Ile Asn Pro Lys Glu Phe Val Met Asn Pro Ala Asn Ala Gln Gly Arg
225                 230                 235                 240

His Thr Pro Gly Thr Arg Leu
                245

<210> SEQ ID NO 44
<211> LENGTH: 64
<212> TYPE: PRT
<213> ORGANISM: Artificial Sequence
<220> FEATURE:
<223> OTHER INFORMATION: Amino acid sequence of Antennapedia from C3APL

<400> SEQUENCE: 44

Val Met Glu Ser Arg Lys Arg Ala Arg Gln Thr Tyr Thr Arg Tyr Gln
1               5                   10                  15

Thr Leu Glu Leu Glu Lys Glu Phe His Phe Asn Arg Tyr Leu Thr Arg
                20                  25                  30

Arg Arg Arg Ile Glu Ile Ala His Ala Leu Cys Leu Thr Glu Arg Gln
            35                  40                  45

Ile Lys Ile Trp Phe Gln Asn Arg Arg Met Lys Trp Lys Lys Glu Asn
        50                  55                  60

<210> SEQ ID NO 45
<211> LENGTH: 19
<212> TYPE: PRT
<213> ORGANISM: Artificial Sequence
<220> FEATURE:
<223> OTHER INFORMATION: Amino acid sequence of Antennapedia from C3APS

<400> SEQUENCE: 45

Arg Gln Ile Lys Ile Trp Phe Gln Asn Arg Arg Met Lys Trp Lys Lys
1               5                   10                  15

Val Asp Ser
```

```
<210> SEQ ID NO 46
<211> LENGTH: 60
<212> TYPE: PRT
<213> ORGANISM: Artificial Sequence
<220> FEATURE:
<223> OTHER INFORMATION: Amino acid sequence of HIV-1 Tat from C3-TL

<400> SEQUENCE: 46

Lys His Pro Gly Ser Gln Pro Lys Thr Ala Cys Thr Asn Cys Tyr Cys
1               5                   10                  15

Lys Lys Cys Cys Phe His Cys Gln Val Cys Phe Ile Thr Lys Ala Leu
            20                  25                  30

Gly Ile Ser Tyr Gly Arg Lys Arg Arg Gln Arg Arg Ala His Gln
        35                  40                  45

Asn Ser Gln Thr His Gln Ala Ser Leu Ser Lys Gln
    50                  55                  60

<210> SEQ ID NO 47
<211> LENGTH: 20
<212> TYPE: PRT
<213> ORGANISM: Artificial Sequence
<220> FEATURE:
<223> OTHER INFORMATION: Amino acid sequence of HIV-1 Tat from C3-TS

<400> SEQUENCE: 47

Tyr Gly Ala Lys Lys Arg Arg Gln Arg Arg Val Asp Ser Ser Gly
1               5                   10                  15

Pro His Arg Asp
            20

<210> SEQ ID NO 48
<211> LENGTH: 17
<212> TYPE: PRT
<213> ORGANISM: Artificial Sequence
<220> FEATURE:
<223> OTHER INFORMATION: Amino acid sequence of the proline rich region
      of C3APLT

<400> SEQUENCE: 48

Val Met Asn Pro Ala Asn Ala Gln Gly Arg His Thr Pro Gly Thr Arg
1               5                   10                  15

Leu

<210> SEQ ID NO 49
<211> LENGTH: 10
<212> TYPE: PRT
<213> ORGANISM: Artificial Sequence
<220> FEATURE:
<223> OTHER INFORMATION: Amino acid sequence fused to C3 protein to
      created C3 Tat-short

<400> SEQUENCE: 49

Tyr Gly Arg Lys Arg Arg Gln Arg Arg Arg
1               5                   10

<210> SEQ ID NO 50
<211> LENGTH: 8
<212> TYPE: PRT
<213> ORGANISM: Artificial Sequence
<220> FEATURE:
<223> OTHER INFORMATION: Reverse sequence of Tat amino acids fused to
      C3 protein to created C3Basic3
```

-continued

```
<400> SEQUENCE: 50

Arg Arg Gln Arg Arg Lys Lys Arg
1               5

<210> SEQ ID NO 51
<211> LENGTH: 12
<212> TYPE: PRT
<213> ORGANISM: Artificial Sequence
<220> FEATURE:
<223> OTHER INFORMATION: transport peptide rich in Proline

<400> SEQUENCE: 51

Ala Ala Val Leu Leu Pro Val Leu Leu Ala Ala Pro
1               5                   10

<210> SEQ ID NO 52
<211> LENGTH: 24
<212> TYPE: PRT
<213> ORGANISM: Artificial Sequence
<220> FEATURE:
<223> OTHER INFORMATION: Sperm fertiline alpha peptide

<400> SEQUENCE: 52

His Pro Ile Gln Ile Ala Ala Phe Leu Ala Arg Ile Pro Pro Ile Ser
1               5                   10                  15

Ser Ile Gly Thr Cys Ile Leu Lys
            20

<210> SEQ ID NO 53
<211> LENGTH: 9
<212> TYPE: PRT
<213> ORGANISM: Artificial Sequence
<220> FEATURE:
<223> OTHER INFORMATION: Amino acid sequence from the C3Basic3

<400> SEQUENCE: 53

Arg Arg Lys Gln Arg Arg Lys Arg Arg
1               5
```